US008076458B2

(12) United States Patent
Ohta et al.

(10) Patent No.: US 8,076,458 B2
(45) Date of Patent: Dec. 13, 2011

(54) ANTI-CLAUDIN-4 ANTIBODY

(75) Inventors: So Ohta, Shizuoka (JP); Hiroshi Ando, Machida (JP); Masayo Suzuki, Machida (JP); Shinobu Kawamoto, Machida (JP); Mariko Nakano, Machida (JP); Kazuyasu Nakamura, Machida (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 513 days.

(21) Appl. No.: 12/049,581

(22) Filed: Mar. 17, 2008

(65) Prior Publication Data

US 2009/0202556 A1  Aug. 13, 2009

Related U.S. Application Data

(60) Provisional application No. 60/946,518, filed on Jun. 27, 2007, provisional application No. 60/969,269, filed on Aug. 31, 2007.

(30) Foreign Application Priority Data

Mar. 16, 2007  (JP) ................................. 2007-068064
Aug. 30, 2007  (JP) ................................. 2007-223803

(51) Int. Cl.
*C07K 16/00* (2006.01)
*G01N 33/53* (2006.01)
(52) U.S. Cl. ............... 530/387.1; 530/387.3; 530/387.9; 530/388.1; 530/388.15; 435/7.1
(58) Field of Classification Search .......................... None
See application file for complete search history.

(56) References Cited

U.S. PATENT DOCUMENTS 6,632,927 B2 * 10/2003 Adair et al. ................. 530/387.3
2005/0074798 A1   4/2005 Sukumar et al.
2006/0084594 A1 *  4/2006 Santin et al. ........................ 514/8

FOREIGN PATENT DOCUMENTS

EP          2103628 A1    9/2009
JP       2006-525351 A   11/2006
WO         00/26360 A1    5/2000

OTHER PUBLICATIONS

Offner, 2005, Cancer Immunology Immunotherapy, vol. 54, pp. 431-455.*
Amit et al., 1986, Science, vol. 233, No. 4765, pp. 747-753.*
Panka et al., 1988, Proc. Natl. Acad. Sci. USA, vol. 85, pp. 3080-3084.*
Rudikoff et al., 1982, Proc. Natl. Acad. Sci. USA, vol. 79, pp. 1979-1983.*
International Search Report (PCT/ISA/210) issued Apr. 15, 2008 in corresponding PCT/JP2008/054769.
Anonymous: "Mouse anti claudin-4 antibody", invitrogen catalogue, Mar. 1, 2005, pp. 1-2, XP002571024.
Communication dated Jan. 24, 2011, issued in corresponding European Application No. 08722165.1.

* cited by examiner

*Primary Examiner* — Robert Landsman
*Assistant Examiner* — Ian Dang
(74) *Attorney, Agent, or Firm* — Sughrue Mion, PLLC

(57) ABSTRACT

An object of the present invention is to provide a monoclonal antibody which is useful as a diagnostic agent or a therapeutic agent for a disease relating to a polypeptide encoded by Claudin-4 (hereinafter referred to as "CLDN4") gene or a polypeptide encoded by a Claudin-3 (hereinafter referred to as "CLDN3") gene, or a method for using the same. Accordingly, the present invention provides a monoclonal antibody or an antibody fragment thereof, which specifically recognizes three-dimensional structure of an extracellular region of CLDN4 and binds to the extracellular region; a monoclonal antibody or an antibody fragment thereof, which specifically recognizes three-dimensional structure of both of extracellular regions of CLDN3 and CLDN4 and binds to the extracellular regions; a hybridoma which produces the antibody; a DNA which encodes the antibody; a vector which comprises the DNA; a transformant obtained by transforming the vector; a process for producing an antibody or an antibody fragment thereof using the hybridoma or the transformant; and a diagnostic agent or a therapeutic agent for a disease relating to a polypeptide encoded by CLDN4 gene and/or CLDN3 gene using the antibody or the antibody fragment.

19 Claims, 23 Drawing Sheets

FIG. 1
CLDN3/CHO
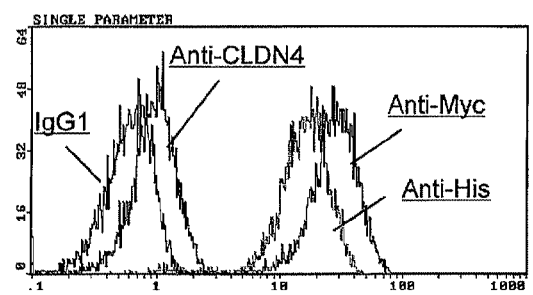
CLDN6/CHO
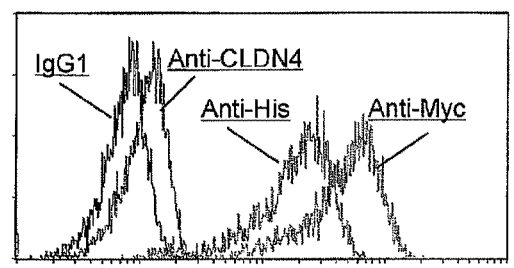
CLDN4/CHO
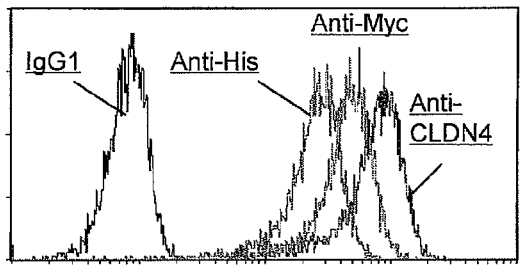
CLDN9/CHO
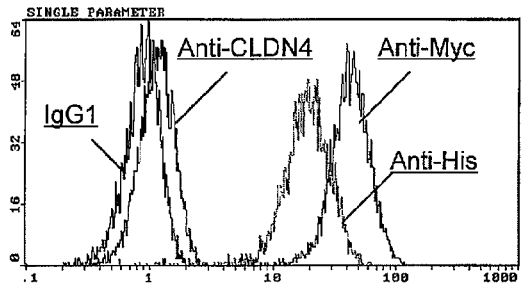
CLDN5/CHO
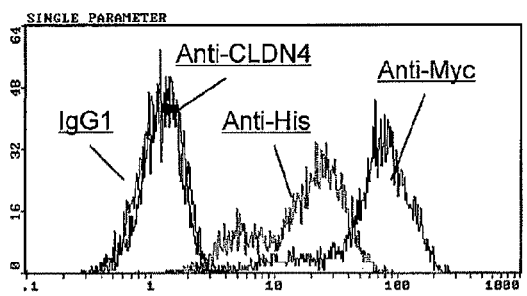

FIG. 7
Detected Antibody: Normal Rabbit Serum
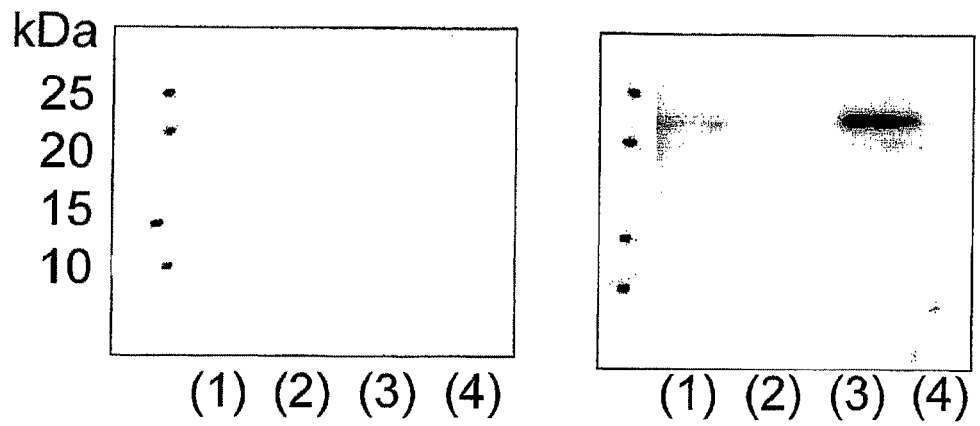
Detected Antibody: KM511
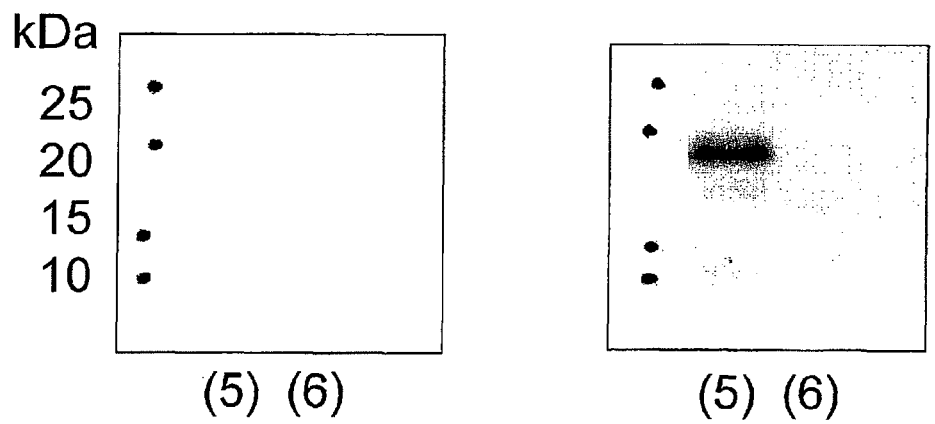
| | Immuno-precipitated antibody | Cell lysate |
|---|---|---|
| (1) | Anti-CLDN3 Polyclonal Antibody | CLDN3/CHO |
| (2) | Anti-CLDN3 Polyclonal Antibody | Vector/CHO |
| (3) | KM3907 | CLDN3/CHO |
| (4) | KM3907 | Vector/CHO |
| (5) | KM3907 | CLDN4/CHO |
| (6) | KM3907 | Vector/CHO |

FIG. 8
CLDN4/CHO
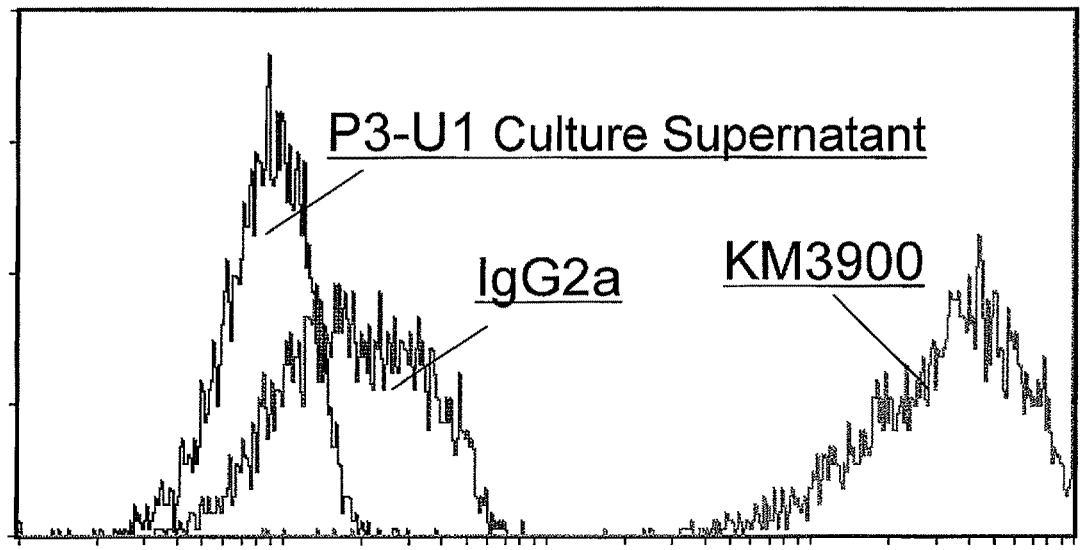
CLDN6/CHO
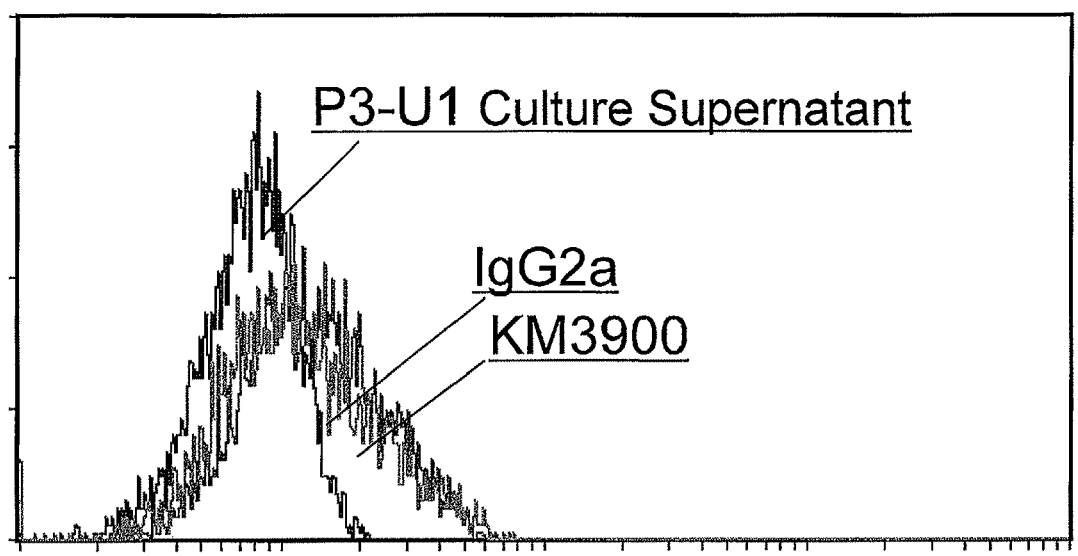

FIG. 9
Pancreatic Cancer
Capan-2
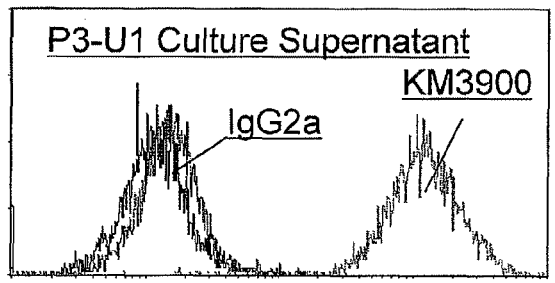
HPAF-II
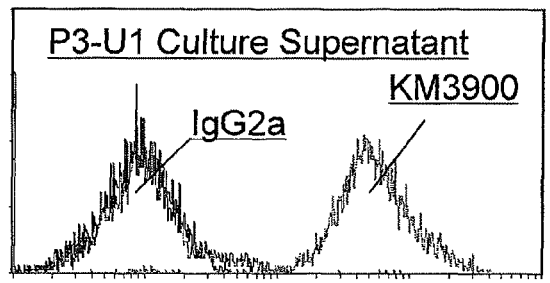
Lymphoma
Daudi
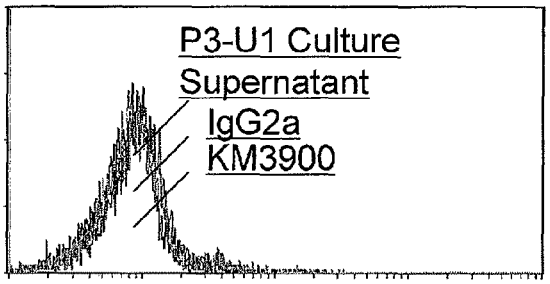

FIG. 11
KM511
0 h | 21 h
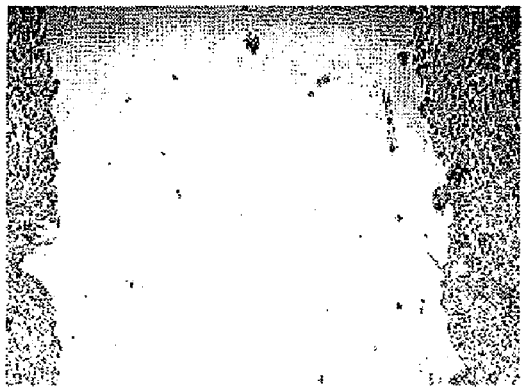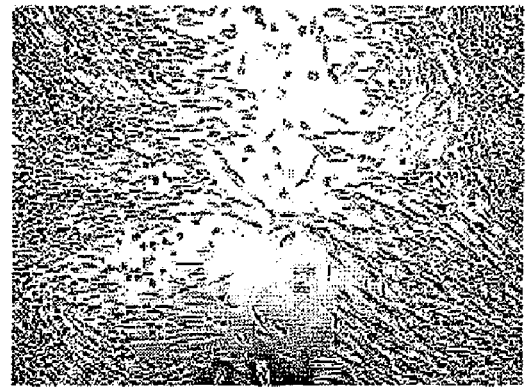
KM3900
0 h | 21 h
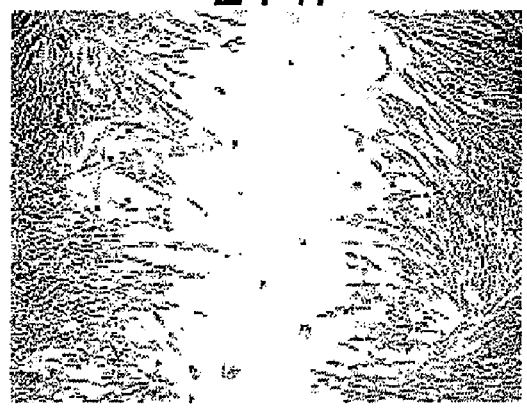

FIG. 16
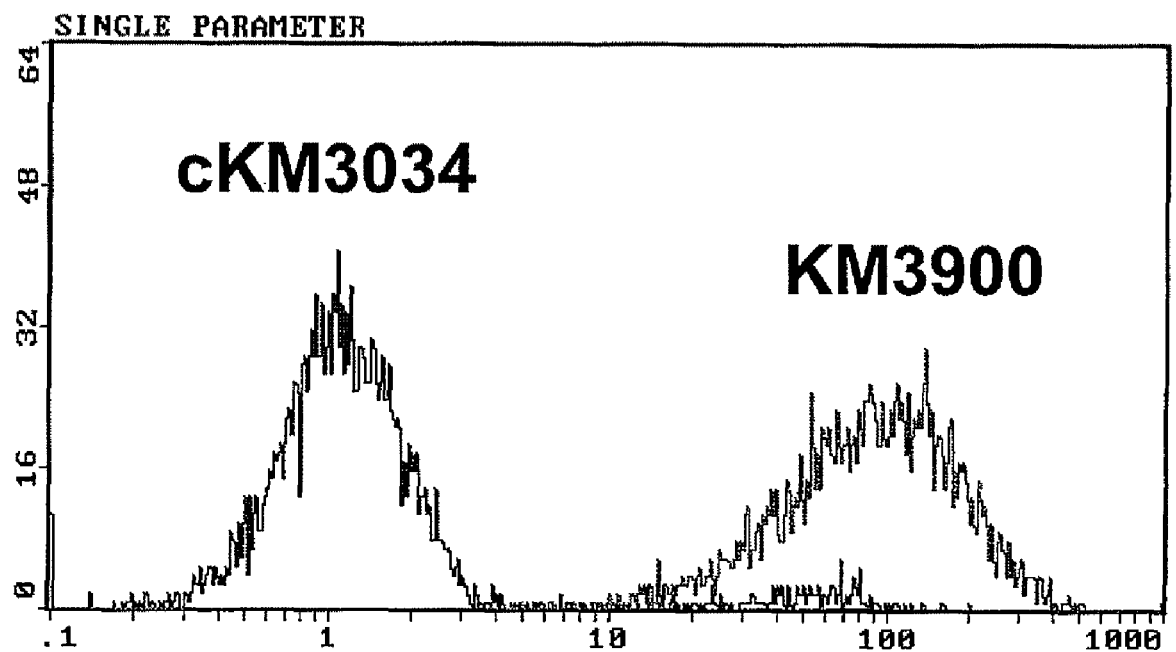
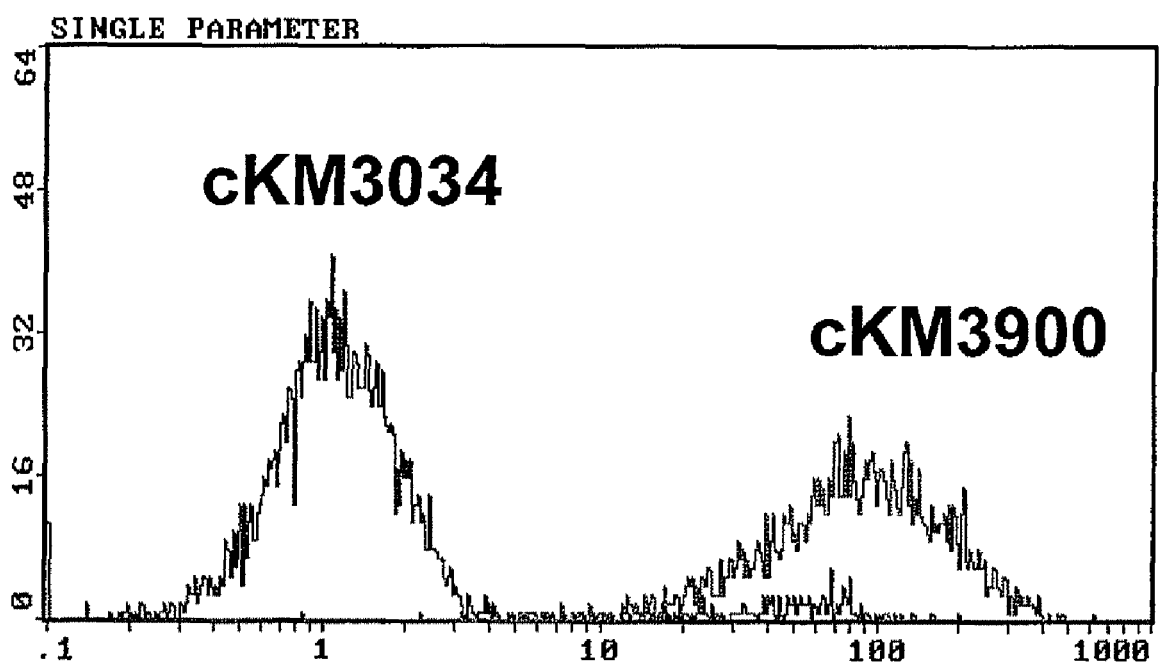

FIG. 18
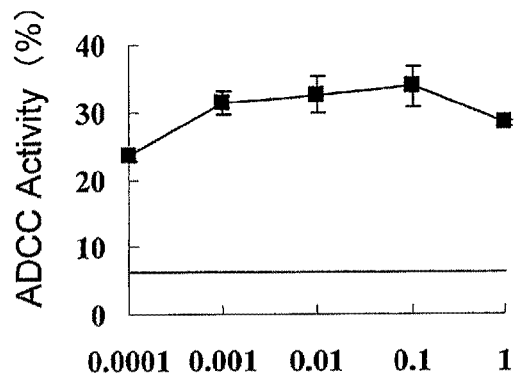
CLDN4/CHO
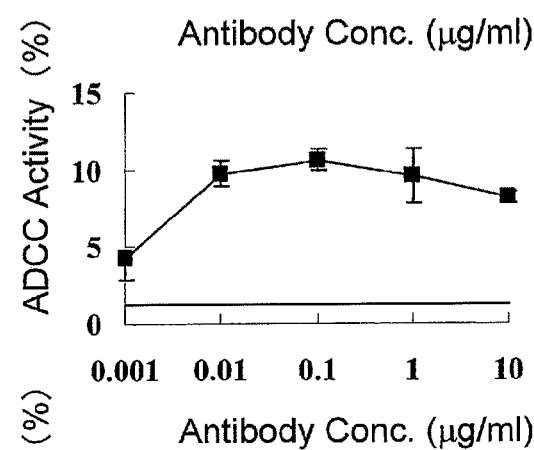
Capan-2
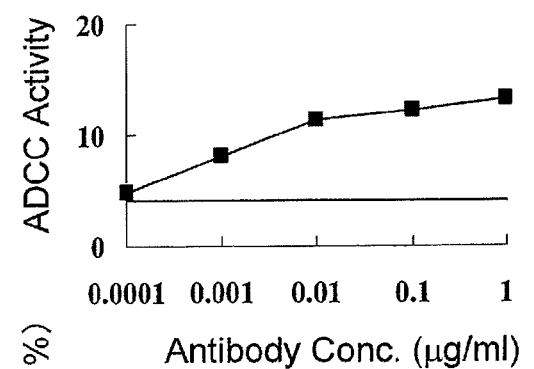
MCAS
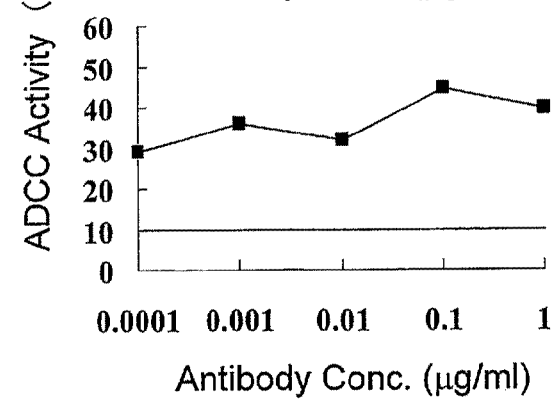
MCF7

FIG. 19
CLDN4/CHO
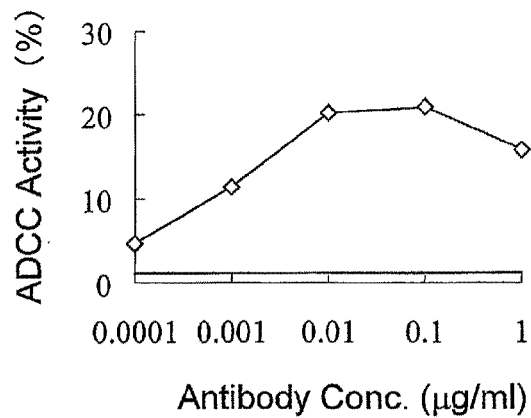
CLDN3/CHO
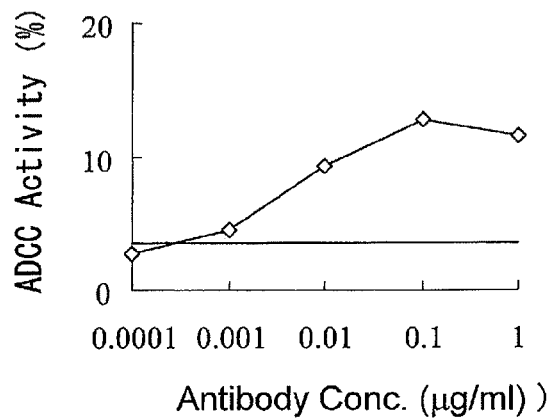
MCAS
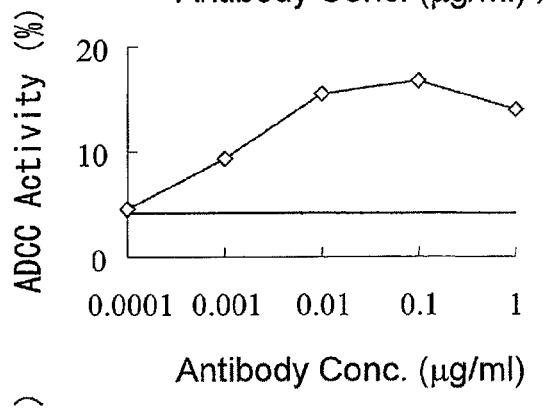
MCF7
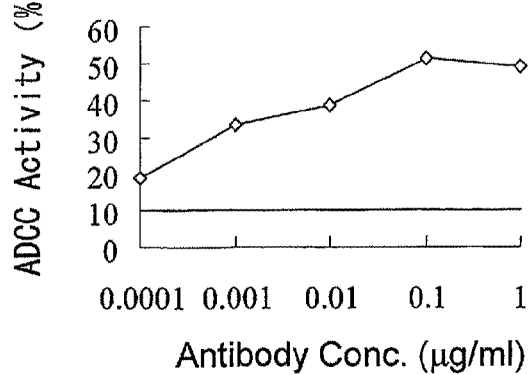

FIG. 21
CLDN4/CHO
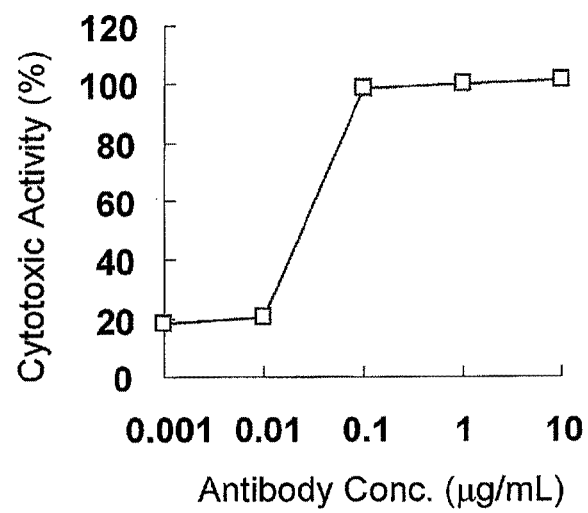
CLDN3/CHO
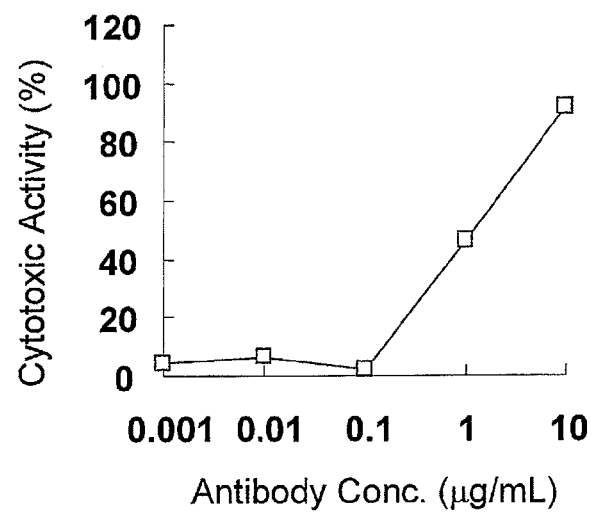
MCF7
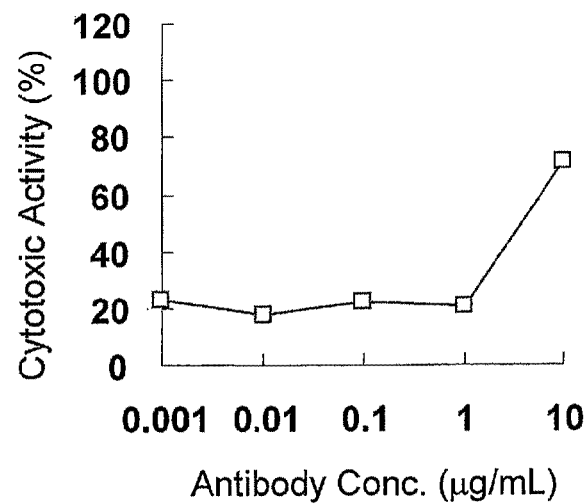

FIG. 22
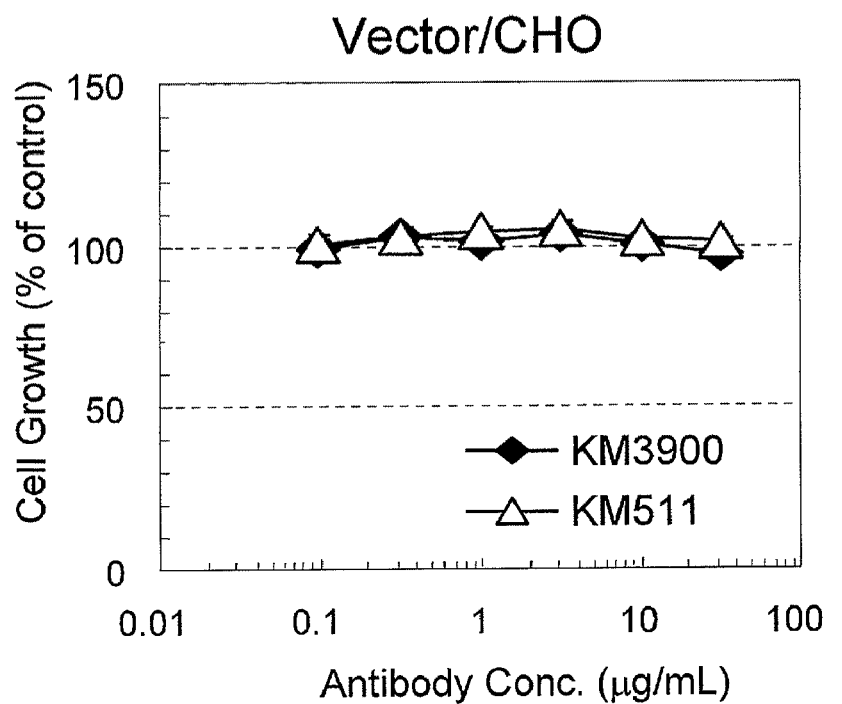
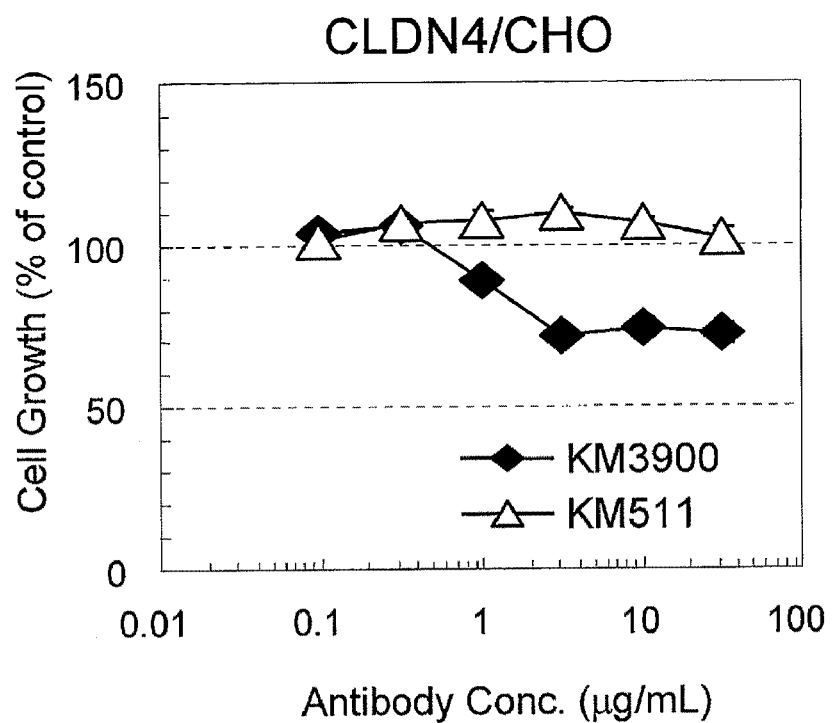

FIG. 23
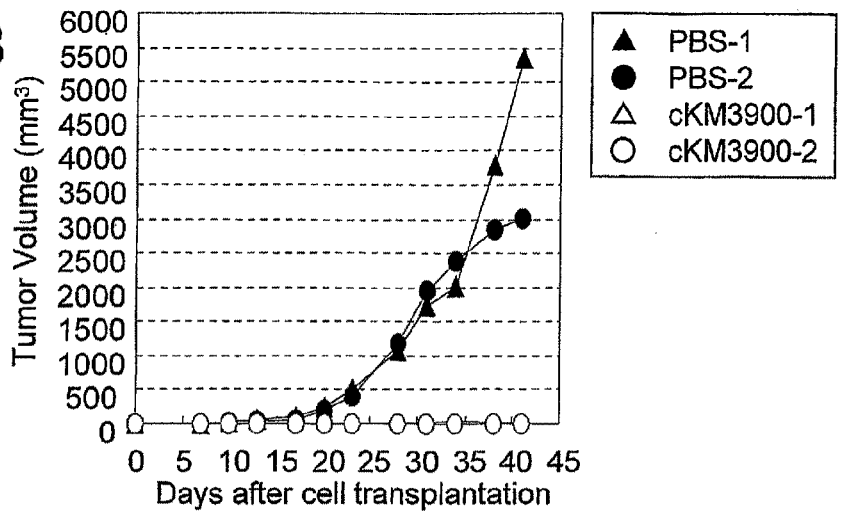
CLDN4/CHO
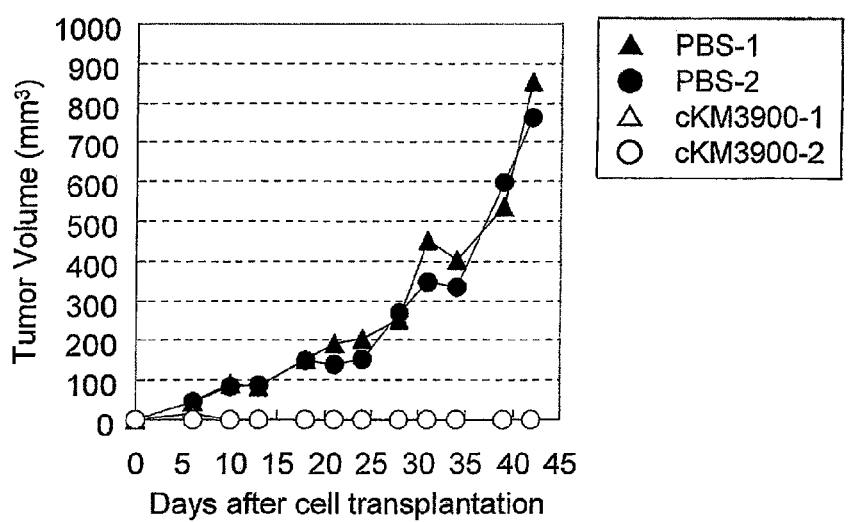
Capan-2
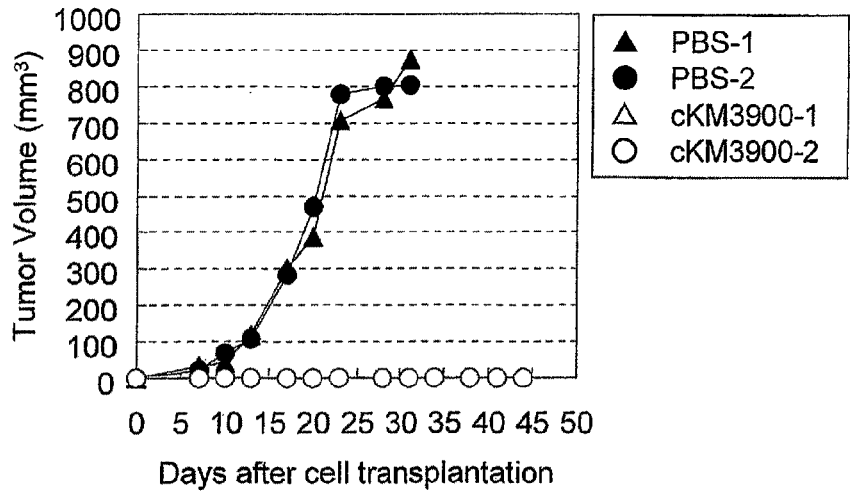
MCAS

ANTI-CLAUDIN-4 ANTIBODY

BACKGROUND OF THE INVENTION

1. Field of the Invention

The present invention relates to a monoclonal antibody or an antibody fragment thereof, which specifically recognizes three-dimensional structure of an extracellular region of a polypeptide encoded by Claudin-4 (hereinafter referred to as "CLDN4") gene and binds to the extracellular region; a monoclonal antibody or an antibody fragment thereof, which specifically recognizes three-dimensional structures of extracellular regions of a polypeptide encoded by a Claudin-3 (hereinafter referred to as "CLDN3") gene and a polypeptide encoded by a CLDN4 gene, and binds to both of the extracellular regions; a hybridoma which produces the antibody; a DNA which encodes the antibody; a vector which comprises the DNA; a transformant obtained by transforming the vector; a process for producing an antibody or an antibody fragment thereof using the hybridoma or the transformant; and a diagnostic agent or a therapeutic agent using the antibody or the antibody fragment thereof.

2. Brief Description of the Background Art

As the Claudin molecules (hereinafter Claudin is referred to as "CLDN"), 24 kinds of family molecules have so far been reported, and it is considered that CLDN molecules are homophilicly or heterophilicly bound to each other and function in intercellular adhesion (Non-patent Document 1). It is considered that a tight junction (hereinafter referred to as "TJ") formed by CLDN functions as a barrier for preventing free pass of water-soluble molecules through the gap between epithelial cells or vascular endothelial cells (Non-patent Documents 1 and 4). Also, it is considered that TJ also functions as a partition of membrane protein and lipid molecules between the apex and lateral base of cell membrane and as a fence to block their mutual diffusion (Non-patent Document 1).

CLDN4 is a four-transmembrane protein containing total 209 amino acids in length and is an adhesion molecule which constitutes TJ, cloned in 1997 by Katahira et al. as a receptor for Welch *bacillus* enterotoxin [*Clostridium perfringens* enterotoxin (hereinafter referred to as "CPE")] (Non-patent Documents 2 and 3).

Regarding expression of CLDN4 in cancer, its high level expression has been reported in various cancers such as pancreatic cancer (Non-patent Documents 5, 6 and 7), ovarian cancer (Non-patent Documents 8 and 9), breast cancer (Non-patent Document 10), uterine cancer (Non-patent Document 11), colorectal cancer (Non-patent Document 12), stomach cancer (Non-patent Documents 13 and 14), prostate cancer (Non-patent Document 15), esophageal carcinoma (Non-patent Document 16) and biliary cancer (Non-patent Document 17), and it has been reported that high expression of CLDN4 is a cause of poor prognosis in stomach cancer (Non-patent Document 13). Regarding the activity of CLDN4 in cancers, it has been reported that tumor forming ability and cell moving ability are accelerated in a CLDN4-expressed cancer cell and that the infiltrating ability of a cancer cell is reduced when expression of CLDN4 in the cell is suppressed using a small interfering RNA for CLDN4 (Non-patent Document 18).

On the other hand, similar to CLDN4, Claudin-3 (hereinafter referred to as "CLDN3") was cloned as a receptor for CPE by Katahira et al. in 1997 (Non-patent Documents 2 and 3). At the same time, it has been reported that the gene of CLDN3 has a high homology with that of rat ventral prostate.1 protein (RVP.1) reported as a gene in which expression increases in rat prostate atrophy after castration (Non-patent Document 3). CLDN3 is a four-transmembrane protein containing total 220 amino acids in length and is one of the CLDN family constituting TJ.

Regarding expression of CLDN4 in cancers, its high level expression has been reported in various cancers such as ovarian cancer (Non-patent Documents 19, 20 and 21), breast cancer (N4 on-patent Document 22), uterine cancer (Non-patent Document 23), prostate cancer (Non-patent Documents 24 and 25), esophageal carcinoma (Non-patent Document 26), stomach cancer (on-patent Document 27) and colorectal cancer (Non-patent Document 28). Regarding the activity of CLDN3 in cancers, it has been reported that tumor forming ability and cell moving ability are accelerated in a CLDN3-expressed cancer cell and that the infiltrating ability of a cancer cell is decreased when expression of CLDN3 in the cell is suppressed using a small interfering RNA for CLDN3 (Non-patent Document 18). On the other hand, there are a report stating that expression of CLDN3 is decreased in a breast cancer cell line having high infiltrating ability (Non-patent Document 29) and a report stating that prognosis of CLDN3-positive patients of stomach cancer (Non-patent Document 30), so that there are many points which are still unclear regarding its function in cancers.

As a molecule which binds to CLDN3 and CLDN4, there is a Welch *bacillus* enterotoxin (CPE) which is a pathogenic bacterium of food poisoning. CPE is a membrane void-forming toxin which forms a complex by binding to CLDN3 or CLDN4 and destroys cells by cutting holes through the cell membrane. It has been reported that CPE has a cell-killing activity upon cancer cells which express CLDN3 or CLDN4, and shows the effect to suppress tumor growth or to prolong life (Non-patent Documents 9 and 10). Also, it has been reported that a C-terminal partial peptide of CPE (hereinafter referred to as "C-CPE") from which the cell-killing activity of CPE was removed keeps its CLDN-binding activity, and inhibits the barrier activity of TJ by specifically suppressing expression of CLDN4 when it is added to a cell expressing CLDN4 (on-patent Document 4). Regarding C-CPE, activity of accelerating absorption via an intracellular space pathway (paracellular route) by inhibiting the barrier activity of TJ has also been reported (Non-patent Document 33).

As the antibody which binds to an extracellular region of CLDN4, a polyclonal antibody prepared by immunizing a domestic fowl with positions 141 to 158 in the amino acid sequence of CLDN4 represented by SEQ ID NO:2 and a monoclonal antibody prepared by immunizing a domestic fowl with positions 29 to 79 in the amino acid sequence of CLDN4 represented by SEQ ID NO:2 are known. It has been reported that the above-mentioned polyclonal antibody reacts with a cell expressing CLDN4 (Non-patent Document 34). In addition, as the above-mentioned monoclonal antibody, 4A4 (IgG3) is commercially available from Abnova. However, a monoclonal antibody which specifically recognizes three-dimensional structure of an extracellular region of CLDN4 and binds to the extracellar region and a monoclonal antibody which binds to an extraregion of CLDN4 and has neutralizing activity for CLDN4 have not so far been known.

As the antibody which binds to CLDN3, a rabbit polyclonal antibody which binds to mouse CLDN3 has been reported (Patent Document 1). In addition, regarding the antibody which recognizes an extracellular region of CLDN3 and binds thereto, it has been reported that a polyclonal antibody prepared by immunizing a domestic fowl with positions 56 to 69 and 139 to 156 in the amino acid sequence of CLDN3 represented by SEQ ID NO:26 react with a CLDN3-positive cancer cell (Non-patent Document 34). However, since the cancer cell to which the polyclonal antibodies has reactivity also expresses CLDN4, specificity of these antibodies has not been confirmed. Accordingly, a monoclonal antibody which specifically recognizes three-dimensional structure of an extracellular region of CLDN3 and binds thereto has not been known.

It is known that generally, when a non-human antibody such as a mouse antibody is administered to human, it is recognized as a foreign substance so that a human antibody for mouse antibody [human anti mouse antibody (HAMA)] is induced in the human body. It is known that HAMA reacts with the administered mouse antibody to thereby induce side effects (Non-patent Documents 35, 36, 37 and 38), quickens disappearance of the mouse antibody from the body (Non-patent Documents 36, 39 and 40) and decreases therapeutic effect of the mouse antibody (Non-patent Documents 41 and 42).

In order to solve these problems, attempts have been made to prepare a human chimeric antibody or a humanized antibody from a non-human antibody using gene recombination techniques.

A humanized antibody has various advantages in administration to human in comparison with a non-human antibody such as a mouse antibody. For example, it has been reported that its immunogenicity was decreased and its blood half-life was prolonged in a test using monkey, in comparison with a mouse antibody (Non-patent Documents 43 and 44). That is, since the humanized antibody causes fewer side effects in human than non-human antibodies, it is expected that its therapeutic effect is sustained for a prolonged time.

Also, since a humanized antibody is prepared using gene recombination techniques, it can be prepared as various forms of molecules. For example, when γ1 subclass is used as a heavy chain (hereinafter referred to as "H chain") constant region (hereinafter referred to as "C region") of a human antibody (H chain C region is referred to as "CH"), a humanized antibody having high effector functions such as antibody-dependent cellular cytotoxicity (hereinafter referred to as "ADCC activity") can be prepared (Non-patent Document 43), and prolongation of its blood half life in comparison with mouse antibodies can be expected (on-patent Document 44), Particularly, in the case of treatment for suppressing proliferation of CLDN-positive cells, cytotoxic activities such as complement-dependent cytotoxicity (hereinafter referred to as "CDC activity") via the Fc region (the region after the antibody heavy chain binge region) of an antibody and ADCC activity are important, in order to specifically damage the target cells by accumulating effector cells in a tumor tissue via the antibody. In the treatment of human, a human chimeric antibody, a humanized antibody or a human antibody is preferably used for exerting the cytotoxic activities (Non-patent Documents 45 and 46).

In addition, with recent advance in protein engineering and genetic engineering, the humanized antibody can also be prepared as an antibody fragment having small molecular weight, such as Fab, Fab', F(ab')$_2$, a single chain antibody (hereinafter referred to as "scFv") (Non-patent Document 47), a dimerized V region fragment Hereinafter referred to as "diabody") (Non-patent Document 48), a disulfide stabilized V region fragment (hereinafter referred to as "dsFv") (Non-patent Document 49), or a peptide comprising a complementarity determining region (hereinafter referred to as "CDR") (Non-patent Document 50), and these antibody fragments have more excellent moving ability to target tissues than complete antibody molecules (Non-patent Document 51).

Non-patent Document 1: *Nat. Rev Mol. Cell. Biol.*, 2, 285 (2001)
Non-patent Document 2: *J. Cell Biol.*, 136, 1239 (1997)
Non-patent Document 3: *J. Biol. Chem.*, 272, 26652 (1997)
Non-patent Document 4: *J. Cell Biol.*, 147, 195 (1999)
Non-patent Document 5: *Am, J. Clin. Pathol.*, 121, 226 (2004)
Non-patent Document 6: *Am. J. Pathol.*, 164, 903 (2004)
Non-patent Document 7: *Gastroenterology*, 121, 678 (2001)
Non-patent Document 8: *Clin. Cancer Res.*, 9, 2567 (2003)
Non-patent Document 9: *Cancer Res.*, 65, 4334 (2005)
Non-patent Document 10: *Am. J. Pathol*, 164, 1627 (2004)
Non-patent Document 11: *Br. J. Cancer*, 92, 1561 (2005)
Non-patent Document 12: *FEBS Lett.*, 579, 6179 (2005)
Non-patent Document 13: *Hum. Pathol.*, 36, 886 (2005)
Non-patent Document 14: *Cancer Epidemiol Biomarkers Prev.*, 15, 281 (2006)
Non-patent Document 15: *Cancer Res.*, 61, 7878 (2001)
Non-patent Document 16: *Appl. Immunohistochem. Mol. Morpho.*, 14, 24 (2006)
Non-patent Document 17: *Mod. Pathol*, 19, 460 (2006)
Non-patent Document 18: *Cancer Res.* 65, 7378 (2005)
Non-patent Document 19: *Clin. Cancer Res.*, 2, 2567 (2003)
Non-patent Document 20: *Clin. Cancer Res.*, 10, 4427 (2004)
Non-patent Document 21: *Clin. Cancer Res.*, 10, 3291 (2004)
Non-patent Document 22: *Am. J Pathol.*, 164, 1627 (2004)
Non-patent Document 23: *Br. J. Cancer*, 2, 1561 (2005)
Non-patent Document 24: *Cancer Res.* 61, 7878 (2001)
Non-patent Document 25: *Hum. Pathol.*, 3, 564 (2007)
Non-patent Document 26: *Hum. Pathol*, 36, 886 (2005)
Non-patent Document 27: *FEBS Let.*, 579, 6179 (2005)
Non-patent Document 28: *Cancer Res.*, 65, 7378 (2005)
Non-patent Document 29: *Oncogene*, 13, 2328 (2006)
Non-patent Document 30: *Virchows Arch.*, 448, 52 (2006)
Non-patent Document 31: *Cancer Res.*, 63, 6265 (2003)
Non-patent Document 32: *Cancer Res.*, 65, 1868 (2005)
Non-patent Document 33: *YAKUGAKU ZASSHI*, 126, 711 (2006)
Non-patent Document 34: *Cancer Immunol Immunother.*, 54, 431 (2005)
Non-patent Document 35: *J. Clin. Oncol*, 2, 881 (1984)
Non-patent Document 36: *Blood*, 65, 1349 (1985)
Non-patent Document 37: *J. Natl Cancer Inst.* 80, 932 (1988)
Non-patent Document 38: *Proc. Natl. Acad. Si. USA*, 82, 1242 (1985)
Non-patent Document 39: *J. Nucl. Med.*, 6, 1011 (1985)
Non-patent Document 40: *J. Natl. Cancer Inst.*, 80, 937 (1988)
Non-patent Document 41: *J. Immunol*, 135, 1530 (1985)
Non-patent Document 42: *Cancer Res.*, 46, 6489 (1986)
Non-patent Document 43: *Cancer Res.*, 56, 1118 (1996)
Non-patent Document 44: *Immunol.*, 85, 668 (1995)
Non-patent Document 45: *J. Immunol.*, 144, 1382 (1990)
Non-patent Document 46: *Nature*, 322, 323 (1988)
Non-patent Document 47: *Science*, 242, 423 (1938)
Non-patent Document 48: *Nature Biotechnol*, 15, 629 (1997)
Non-patent Document 49: *Molecular Immunol.*, 32, 249 (1995)
Non-patent Document 50: *J. Biol. Chem.*, 271, 2966 (1996)
Non-patent Document 51: *Cancer Res.*, 52, 3402 (1992)
Patent Document 1: Japanese Patent 3428441

SUMMARY OF THE INVENTION

An object of the present invention is to provide a monoclonal antibody which is useful as a diagnostic agent or a therapeutic agent for a disease relating to a polypeptide encoded by Claudin-4 (hereinafter referred to as "CLDN4") gene or a polypeptide encoded by a Claudin-3 (hereinafter referred to as "CLDN3") gene, or a method for using the same.

The present invention provides a monoclonal antibody which specifically recognizes three-dimensional structure of an extracellular region of a polypeptide encoded by a CLDN4 gene and binds to the extracellular region, and a monoclonal antibody which specifically recognizes three-dimensional structure of an extracellular region of each of a polypeptide encoded by CLDN3 gene and a polypeptide encoded by a CLDN4 gene, and binds to both of the polypeptides. Also, the present invention provides a diagnostic agent or a therapeutic agent for various diseases relating to a polypeptide encoded by a CLDN4 gene, and a diagnostic agent or a therapeutic agent for various diseases relating to both CLDN3 and CLDN4.

BRIEF DESCRIPTION OF THE DRAWINGS

FIG. 1 shows results in which the reactivity of a commercially available anti-CLDN4 monoclonal antibody 3E2C1, an anti-myc antibody and an anti-His antibody for immobilized CLDN-expressing cells, CLDN3/CHO, CLDN4/CHO, CLDN5/CHO, CLDN6/CHO and CLDN9/CHO was measured by a flow cytometry (hereinafter referred to as "FCM"). The ordinate shows the number of cells, and the abscissa shows fluorescence intensity.

FIG. 4 shows results when a negative control antibody KM511, a commercially available anti-CLDN4 monoclonal antibody 3E2C1 or an anti-CLDN4 monoclonal antibody KM3900 were allowed to react as the primary antibody.

FIG. 5 shows results when immunoprecipitation with the anti-CLDN4 monoclonal antibody KM3900 was carried out and then an anti-G-CSF derivative antibody KM511 as a negative control antibody or a commercially available anti-CLDN4 monoclonal antibody 3E2C1 was allowed to react as the primary antibody.

FIG. 7 shows results in which the reactivity of an anti-CLDN4 monoclonal antibody KM3907 for CLDN3 protein and CLDN4 protein was examined by immunoprecipitation. From the left side of the lane, (1) CLDN3/CHO immunoprecipitated with an anti-CLDN3 polyclonal antibody (manufactured by NOVUS), (2) Vector/CHO immunoprecipitated with the anti-CLDN3 polyclonal antibody, (3) CLDN3/CHO immunoprecipitated with KM3907, (4) Vector/CHO immunoprecipitated with KM3907, (5) CLDN4/CHO immunoprecipitated with KM3907 and (6) Vector/CHO immunoprecipitated with KM3907 are shown. A normal rabbit serum or KM511 was used as a negative control antibody to be detected, and a commercially available anti-CLDN3 polyclonal antibody or an anti-CLDN4 monoclonal antibody 3E2C1 was used as an antibody to be detected.

FIG. 8 shows results in which the reactivity of a P3-U1 culture supernatant (P3-U1 culture sup.), a negative control antibody IgG2a and an anti-CLDN4 monoclonal antibody KM3900 for CLDN4-myc/His gene-introduced CHO cell (CLDN4/CHO) and CLDN6-myc/His gene-introduced CHO cell (CLDN6/CHO) was measured by FCM. The ordinate shows the number of cells, and the abscissa shows fluorescence intensity.

FIG. 9 shows results in which the reactivity of a P3-U1 culture supernatant (P3-U1 culture sup.), a negative control antibody IgG2a and an anti-CLDN4 monoclonal antibody KM3900 for Capan-2, HPAF-II and Daudi was measured by FCM. The ordinate shows the number of cells, and the abscissa shows fluorescence intensity.

FIG. 11 shows typical photographic images of a cell peeling area before adding an anti-G-CSF derivative antibody KM511 as a negative control antibody and an anti-CLDN4 monoclonal antibody KM3900 at a concentration of 1 µg/ml to CLDN4-myc/His gene-introduced CHO cell (CLDN4/CHO) (0 h), or when culturing was carried out for 21 hours after the addition (21 h) by the wound healing method.

FIG. 16 shows results in which the reactivity of an anti-FGF-8 human chimeric antibody cKM3034 as a negative control antibody, an anti-CLDN4 human chimeric antibody cKM3900 and an anti-CLDN4 monoclonal antibody KM3900 for human pancreatic cancer cell line Capan-2 was measured by FCM. The ordinate shows the number of cells, and the abscissa shows fluorescence intensity.

FIG. 18 shows results in which the ADCC activity of an anti-CLDN4 human chimeric antibody cKM3900 for CLDN4-myc/His gene-introduced CHO cell (CLDN4/CHO), human pancreatic cancer cell line Capan-2, human ovarian cancer cell line MCAS and human breast cancer cell line MCF7 was measured. The ordinate shows ADCC activity (%), and the abscissa shows antibody concentration. The solid line shows cytotoxic activity at the time of the antibody non-addition.

FIG. 19 shows results in which the ADCC activity of an anti-CLDN4 human chimeric antibody cKM3907 for CLDN4-myc/His gene-introduced CHO cell (CLDN4/CHO), CLDN3-myc/His gene-introduced CHO cell (CLDN3/CHO), human ovarian cancer cell line MCAS and human breast cancer cell line MCF7 was measured. The ordinate shows ADCC activity (%), and the abscissa shows the antibody concentration. The solid line shows cytotoxic activity at the time of the antibody non-addition.

FIG. 21 shows results in which the CDC activity of an anti-CLDN4 human chimeric antibody cKM3907 for CLDN4-myc/His gene-introduced CHO cell (CLDN4/CHO), CLDN3-myc/His gene-introduced CHO cell (CLDN3/CHO) and human breast cancer cell line MCF7 was measured. The ordinate shows CDC activity (%), and the abscissa shows antibody concentration.

FIG. 22 shows results in which the cell growth inhibitory activity of an anti-CLDN4 monoclonal antibody KM3900 for CLDN4-myc/His gene-introduced CHO cell (CLDN4/CHO) and vector-introduced CHO cell (Vector/CHO) was measured. The ordinate shows the growth rate (%) when the antibody non-added sample was regarded as 100%, and the abscissa shows added antibody concentration.

FIG. 23 shows in viva antitumor activity of an anti-CLDN4 human chimeric antibody cKM3900 for CLDN4-myc/His gene-introduced CHO cell (CLDN4/CHO), human pancreatic cancer cell line Capan-2 and human ovarian cell line MCAS. The ordinate shows tumor volume (mm$^3$), and the abscissa shows the number of days after cell transplantation.

DETAILED DESCRIPTION OF THE INVENTION

Figure 2:
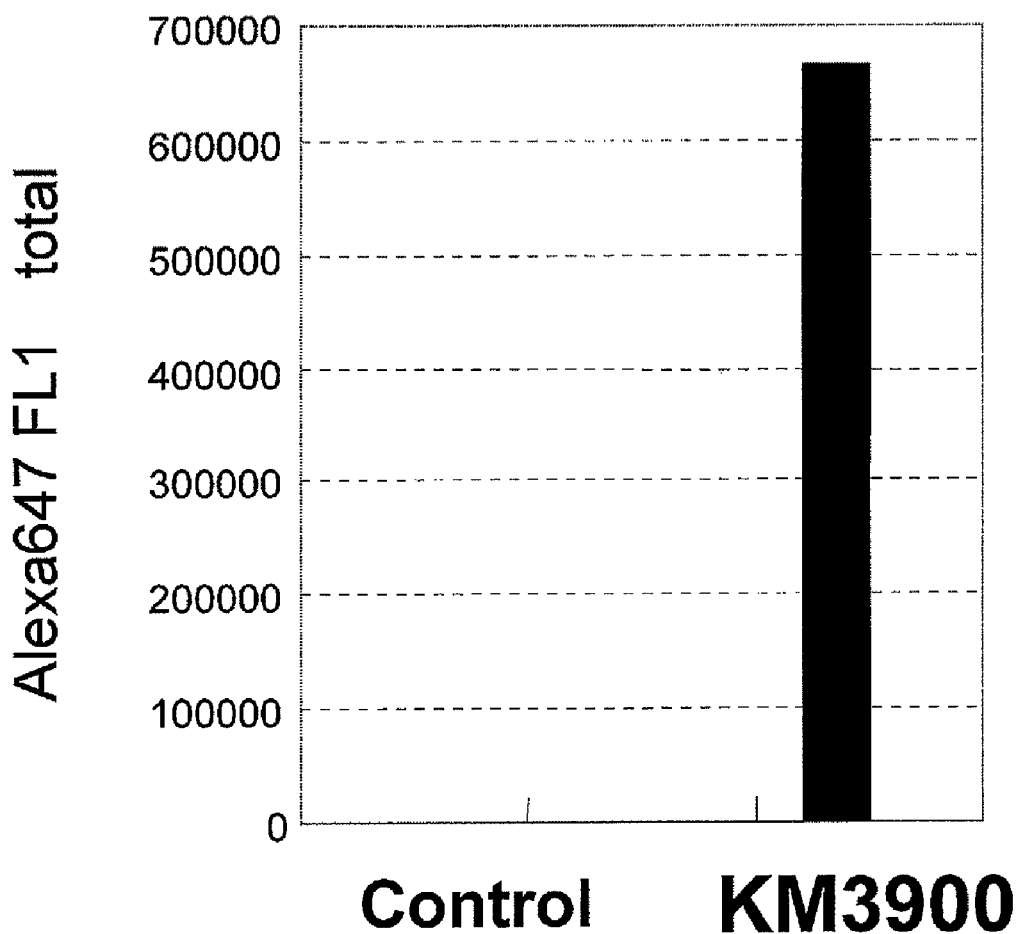
FIG. 2 shows results in which the reactivity of an anti-CLDN4 monoclonal antibody KM3900 for CLDN4-myc/His gene-introduced CHO cell (CLDN4/CHO) and vector-introduced CHO cell (Vector/CHO) was measured by ABI 8200. The ordinate shows fluorescence intensity.

Specifically, the present invention relates to the following (1) to (50):

(1) A monoclonal antibody or an antibody fragment thereof, which specifically recognizes three-dimensional structure of an extracellular region of a polypeptide encoded by Claudin-4 (hereinafter referred to as "CLDN4") gene and binds to the extracellular region.

(2) A monoclonal antibody or an antibody fragment thereof, which specifically binds to an extracellular region of a polypeptide encoded by a CLDN4 gene (hereinafter referred to as "extracellular region of CLDN4") and has neutralizing activity for CLDN4.

(3) The monoclonal antibody or the antibody fragment thereof according to (1) or (2), which recognizes three-dimensional structure comprising positions 28 to 76 or positions 141 to 159 in the amino acid sequence of the extracellular region of CLDN4 and specifically binds to die extracellular region.

(4) The monoclonal antibody or the antibody fragment thereof according to any one of (1) to (3), wherein the monoclonal antibody is a monoclonal antibody which competes with a monoclonal antibody produced by a hybridoma KM3900 (FERM BP-10751) in the binding to the extracellular region of CLDN4.

(5) The monoclonal antibody or the antibody fragment thereof according to any one of (1) to (4), wherein the monoclonal antibody is a monoclonal antibody which binds to an epitope in the extracellular region of CLDN4 to which a monoclonal antibody produced by a hybridoma KM3900 (FERM BP-10751) binds.

(6) The monoclonal antibody or the antibody fragment thereof according to any one of (1) to (5), wherein the monoclonal antibody is a monoclonal antibody produced by a hybridoma KM3900 (FERM BP-10751).

(7) The monoclonal antibody or the antibody fragment thereof according to any one of (1) to (6), wherein the monoclonal antibody is a recombinant antibody.

(8) The recombinant antibody or the antibody fragment thereof according to (7), wherein the recombinant antibody is a recombinant antibody selected from a human chimeric antibody, a humanized antibody and a human antibody.

(9) The recombinant antibody or the antibody fragment thereof according to (8), wherein CDR1, CDR2 and CDR3 of VH of the antibody comprise the amino acid sequences represented by SEQ ID NOs:19, 20 and 21, respectively.

(10) The recombinant antibody or the antibody fragment thereof according to (8), wherein CDR1, CDR2 and CDR3 of VL of the antibody comprise the amino acid sequences represented by SEQ ID NOs:22, 23 and 24, respectively.

(11) The recombinant antibody or the antibody fragment thereof according to (8), wherein CDR1, CDR2 and CDR3 of VH of the antibody comprise the amino acid sequences represented by SEQ ID NOs:19, 20 and 21, respectively, and CDR1, CDR2 and CDR3 of VL of the antibody comprise the amino acid sequences represented by SEQ ID NOs:22, 23 and 24, respectively.

(12) The human chimeric antibody or the antibody fragment thereof according to (8), which comprises VH and VL of the monoclonal antibody described in any one of (1) to (6).

(13) The human chimeric antibody or the antibody fragment thereof according to (8), wherein VH of the antibody comprises the amino acid sequence at positions 20 to 142 in the amino acid sequence represented by SEQ ID NO:16, and VL of the antibody comprises the amino acid sequence at positions 23 to 130 in the amino acid sequence represented by SEQ ID NO:18.

(14) The humanized antibody or the antibody fragment thereof according to (8), wherein VH of the humanized antibody comprises the amino acid sequence represented by SEQ ID NO:74 or an amino acid sequence in which at least one modification among amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val is introduced in the amino acid sequence represented by SEQ ID NO:74, and VL of the humanized antibody comprises the amino acid sequence represented by SEQ ID NO:76 or an amino acid sequence in which at least one modification among amino acid modifications for substituting Asp at position 1 with Gln, Ser at position 10 with Ile, Ile at position 21 with Met, Leu at position 48 with Trp, Asp at position 71 with Ser, Leu at position 79 with Met and Pro at position 81 with Ala is introduced in the amino acid sequence represented by SEQ ID NO:76.

(15) The humanized antibody or the antibody fragment thereof according to (8), wherein VH of the humanized antibody comprises an amino acid sequence in which at least one modification among amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val is introduced in the amino acid sequence represented by SEQ ID NO:74, and VL of the humanized antibody comprises an amino acid sequence in which at least one modification among amino acid modifications for substituting Asp at position 1 with Gln, Ser at position 10 with Ile, Ile at position 21 with Met, Leu at position 48 with Trp, Asp at position 71 with Ser, Leu at position 79 with Met and Pro at position 81 with Ala is introduced in the amino acid sequence represented by SEQ ID NO:76.

(16) The monoclonal antibody or the antibody fragment thereof according to any one of (1) to (4), which specifically recognizes three-dimensional structure of an extracellular region of a polypeptide encoded by Claudin-3 (hereinafter referred to as "CLDN3") gene and binds to the extracellular region.

(17) The monoclonal antibody or the antibody fragment thereof according to any one of (1) to (4) and (16), wherein the monoclonal antibody is a monoclonal antibody which competes with a monoclonal antibody produced by a hybridoma KM3907 (FERM BP-10885) in the binding to the extracellular region of CLDN4.

(18) The monoclonal antibody or the antibody fragment thereof according to (17), wherein the monoclonal antibody is a monoclonal antibody which binds to an epitope in the extracellular region of CLDN4 to which the monoclonal antibody produced by a hybridoma KM3907 (FERM BP-10885) binds.

(19) The antibody or the antibody fragment thereof according to (18), wherein the monoclonal antibody is a monoclonal antibody produced by a hybridoma KM3907 (FERM BP-10885).

(20) The antibody or the antibody fragment thereof according to any one of (16) to (18), wherein the monoclonal antibody is a recombinant antibody.

(21) The recombinant antibody or the antibody fragment thereof according to (20), wherein the recombinant antibody is a recombinant antibody selected from a human chimeric antibody, a humanized antibody and a human antibody.

(22) The recombinant antibody or the antibody fragment thereof according to (21), wherein CDR1, CDR2 and CDR3 of VH of the antibody comprise the amino acid sequences represented by SEQ ID NOs:59, 60 and 61, respectively.

(23) The recombinant antibody or the antibody fragment thereof according to (21), wherein CDR1, CDR2 and CDR3 of VL of the antibody comprise the amino acid sequences represented by SEQ ID NOs:62, 63 and 64, respectively.

(24) The recombinant antibody or the antibody fragment thereof according to (21), wherein CDR1, CDR2 and CDR3 of VH of die antibody comprise the amino acid sequences represented by SEQ ID NOs:59, 60 and 61, respectively, and CDR1, CDR2 and CDR3 of VL of the antibody comprise the amino acid sequences represented by SEQ ID NOs:62, 63 and 64, respectively.

(25) The human chimeric antibody or the antibody fragment thereof according to (21), which comprises VH and VL of the monoclonal antibody described in any one of (16) to (19).

(26) The human chimeric antibody or the antibody fragment thereof according to (21), wherein VH of the antibody comprises the amino acid sequence at positions 20 to 138 in the amino acid sequence represented by SEQ ID NO:56, and VL of the antibody comprises the amino acid sequence at positions 23 to 130 in the amino acid sequence represented by SEQ ID NO:58.

(27) The antibody fragment according to (1) to (26), wherein the antibody fragment is an antibody fragment selected from Fab, Fab', F(ab')$_2$, a single chain antibody (scFv), dimerized V region (diabody), disulfide stabilized V region (dsFv) and a peptide comprising CDRs.

(28) A hybridoma which produces the monoclonal antibody described in any one of (1) to (6) and (16) to (19).

(29) The hybridoma according to (28), wherein the hybridoma is a hybridoma KM3900 (FERM BP-10751).

(30) The hybridoma according to (28), wherein the hybridoma is a hybridoma KM3907 (FERM BP-10885).

(31) A DNA which encodes the antibody or the antibody fragment thereof described in any one of (1) to (27).

(32) A recombinant vector which comprises the DNA described in (31).

(33) A transformant obtainable by introducing the recombinant vector described in (32) into a host cell.

(34) A process for producing the antibody or the antibody fragment thereof described in any one of (1) to (27), which comprises culturing the hybridoma described in (28) to (30) or the transformant described in (33) in a medium to thereby form and accumulate the antibody or the antibody fragment thereof described in any one of (1) to (27) in culture, and recovering the antibody or the antibody fragment thereof from the culture.

(35) A method for immunologically detecting or measuring a polypeptide encoded by a CLDN4 gene, which comprises using the antibody or the antibody fragment thereof described in any one of (1) to (27).

(36) A reagent for detecting or measuring a polypeptide encoded by a CLDN4 gene, which comprises using the antibody or the antibody fragment thereof described in any one of (1) to (27).

(37) A diagnostic agent for a disease relating to a polypeptide encoded by a CLDN4 gene, which comprises using the antibody or the antibody fragment thereof described in any one of (1) to (27).
(38) The diagnostic agent according to (37), wherein the disease relating to a polypeptide encoded by a CLDN4 gene is a cancer.
(39) A therapeutic agent for a disease relating to a polypeptide encoded by a CLDN4 gene, which comprises the antibody or the antibody fragment thereof described in any one of (1) to (27) as an active ingredient.
(40) The therapeutic agent according to (39), wherein the disease relating to a polypeptide encoded by a CLDN4 gene is a cancer.
(41) A method for diagnosing a disease relating to a polypeptide encoded by a CLDN4 gene, which comprises using the antibody or the antibody fragment thereof described in any one of (1) to (27) to detect or measure a cell expressing a polypeptide encoded by a CLDN4 gene.
(42) A method for diagnosing a disease relating to a polypeptide encoded by a CLDN4 gene, which comprises using the antibody or the antibody fragment thereof described in any one of (1) to (27) to detect or measure a polypeptide encoded by a CLDN4 gene.
(43) The diagnosing method according to (41) or (42), wherein the disease relating to a polypeptide encoded by a CLDN4 gene is a cancer.
(44) Use of the antibody or the antibody fragment thereof described in any one of (1) to (27) for the manufacture of a diagnostic agent for a disease relating to a polypeptide encoded by a CLDN4 gene.
(45) Use of the antibody or the antibody fragment thereof described in any one of (1) to (27) for the manufacture of a therapeutic agent for a disease relating to a polypeptide encoded by a CLDN4 gene.
(46) The use of the antibody or the antibody fragment thereof described in (44) or (45), wherein the disease relating to a polypeptide encoded by a CLDN4 gene is a cancer.
(47) A diagnostic agent for a disease relating to a polypeptide encoded by a CLDN4 gene or a CLDN3 genes which comprises uses the antibody or the antibody fragment thereof described in any one of (16) to (27).
(48) The diagnostic agent according to (47), wherein the disease relating to a polypeptide encoded by a CLDN4 gene or a CLDN3 gene is a cancer.
(49) A therapeutic agent for a disease relating to a polypeptide encoded by a CLDN4 gene and/or a CLDN3 gene, which comprises the antibody or the antibody fragment thereof described in any one of (16) to (27) as an active ingredient.
(50) The therapeutic agent according to (49), wherein the disease relating to a polypeptide encoded by a CLDN4 gene and/or a CLDN3 gene is a cancer.

The present invention is described below in more detail.

The present invention relates to a monoclonal antibody which specifically recognizes three-dimensional structure of an extracellular region of a polypeptide encoded by Claudin-4 (hereinafter the polypeptide encoded by Claudin-4 is sometimes referred to as "CLDN4") gene and binds to the extracellular region.

The CLDN4 gene may be any gene, so long as it encodes CLDN4, and examples include a gene comprising die nucleotide sequence represented by SEQ ID NO:1. Also, the CLDN4 gene in the present invention includes a gene which hybridizes with the DNA consisting of the nucleotide sequence represented by SEQ ID NO:1 under stringent conditions and encodes a polypeptide having the activity of CLDN4; and the like.

In the present invention, the DNA which hybridizes under stringent conditions refers to a DNA which is obtained by colony hybridization, plaque hybridization, Southern hybridization or the like using, for example, a DNA consisting of the nucleotide sequence represented by SEQ ID NO:1 as a probe. A specific example of such DNA is a DNA which can be identified by performing hybridization at 65° C. in the presence of 0.7 to 10 mol/l sodium chloride using a filter with colony- or plaque-derived DNA immobilized thereon, and then washing the filter at 65° C. with a 0.1 to 2-fold concentration SSC solution (1-fold concentration SSC solution: 150 mmol/l sodium chloride and 15 mmol/l sodium citrate). Hybridization can be carried out according to the methods described in *Molecular Cloning, A Laboratory Manual*, Second Edition, Cold Spring Harbor Lab. Press (1989), *Current Protocols in Molecular Biology*, John Wiley & Sons (1987-1997); *DNA Cloning 1: Core Techniques, A Practical Approach*, Second Edition, Oxford University (1995); and the like. Specifically, the DNA capable of hybridization under stringent conditions includes DNA having at least 60% or more homology, preferably 80% or more homology, more preferably 90% or more homology, and most preferably 95% or more homology to the nucleotide sequence represented by SEQ ID NO:1.

In the nucleotide sequence of the gene encoding a protein of a eukaryote, genetic polymorphism is often recognized. The CLDN4 gene used in the present invention also includes a gene in which small modification is generated in the nucleotide sequence by such polymorphism as the gene used in the present invention.

CLDN4 includes a polypeptide comprising the amino acid sequence represented by SEQ ID NO:2; a polypeptide comprising an amino acid sequence in which at least one amino acid is deleted, substituted or added in the amino acid sequence represented by SEQ ID NO:2; a polypeptide comprising an amino acid sequence having at least 60% homology, preferably at least 80% homology, more preferably at least 90% homology, and most preferably at least 95% homology, with the amino acid sequence represented by SEQ ID NO:2, and having the activity of CLDN4; and the like.

The polypeptide comprising an amino acid sequence wherein one or more amino acid residue(s) is/are deleted, substituted and/or added in the amino acid sequence represented by SEQ ID NO:2 can be obtained, for example, by introducing a site-directed mutation into DNA encoding the polypeptide comprising the amino acid sequence represented by SEQ ID NO: 1 by site-directed mutagenesis described in *Molecular Cloning, A Laboratory Manual*, Second Edition (Cold Spring Harbor Laboratory Press, 1989), *Current Protocols in Molecular Biology* (John Wiley & Sons, 1987-1997), *Nucleic Acids Research*, 10, 6487 (1982), *Proc. Natl. Acad. Sci. USA*, 79, 6409 (1982), *Gene*, 34, 315 (1985), *Nucleic Acids Research*, 13, 4431 (1985), Proc. Natl. Acad. Sci. USA, 82, 488 (1985), or the like. The number of amino acid residues which are deleted, substituted or added is not particularly limited, and the number is preferably, 1 to dozens, such as 1 to 20, and more preferably 1 to several, such as 1 to 5.

The number of the homology described in the present invention may be a number calculated by using a homology search program known by the skilled person, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997); Genome Res., 7, 649 (1997);

see BLAST information guide at the National Center for Biotechnology Information web site] or the like.

As the default parameter, G (cost to open gap) is 5 for the nucleotide sequence and 11 for the amino acid sequence; -E (cost to extend gap) is 2 for the nucleotide sequence and 1 for the amino acid sequence; -q (penalty for nucleotide mismatch) is -3; -r (reward for nucleotide match) is; -e (expect value) is 10; -W (wordsize) is 11 residues for the nucleotide sequence and 3 residues for the amino acid sequence; -y (dropoff (X)) for blast extensions in bits) is 20 for blastn and 7 for a program other than blastn; -X (X dropoff value for gapped alignment in bits) is 15; and -Z (final X dropoff value for gapped alignment in bits) is 50 for blastn and 25 for a program other than blastn (see BLAST information guide at the National Center for Biotechnology Information web site).

The polypeptide comprising a partial sequence of the amino acid sequence represented by SEQ ID NO:2 can be prepared according to a method known by the skilled person. For example, it can be prepared by deleting a part of DNA encoding the amino acid sequence represented by SEQ ID NO:2 and culturing a transformant into which all expression vector containing the DNA is introduced. Also, based on the thus prepared polypeptide or DNA, a polypeptide comprising an amino acid sequence in which one or more amino acid(s) is/are deleted, substituted or added in a partial sequence of the amino acid sequence represented by SEQ ID NO:2 can be prepared in the same manner as described above.

The extracellular region of CLDN4 includes, for example, regions predicted by using the amino acid sequence of the polypeptide represented by SEQ ID NO:2 with conventionally known transmembrane region prediction program SOSUI sosui.proteome.bio.tuat.ac.jp/sosuiFRame0.html), prediction program TMHMM ver. 2 www.cbs.dtu.dk/services/TMHMM-2.0) or ExPASy Proteomics Server (Ca.expasy.org).

Examples of the extracellular region of CLDN4 in the present invention includes regions corresponding to positions 29 to 81 and 139 to 160 of the extracellular domain predicted by ExPASy Proteomics Server, regions corresponding to positions 28 to 76 and 141 to 159 of the extracellular domain predicted by a reference [*Cancer Immunol. Immunother.*, 54, 431-445 (2005)] and the like.

In the present invention, the three-dimensional structure of CLDN4 is not limited, so long as it has three-dimensional structure which can be formed by CLDN4 on the cell membrane or three-dimensional structure equivalent to the three-dimensional structure.

Binding of the antibody or antibody fragment of the present invention to the extracellular region of CLDN4 can be confirmed by a method in which the binding ability of a cell expressing a specified antigen and an antibody for the specific antigen is confirmed, for example, by a conventionally known immunological detection method, preferably a fluorescent cell staining method or die like. In addition, it can also be confirmed by a combination of conventionally known immunological detection methods [*Monoclonal Antibodies—Principles and Practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

In the present invention, the cell expressing CLDN4 may be any cell, so long as it expresses CLDN4, and examples include a cell which is naturally present in the human body, a cell line established from the cell which is naturally present in the human body, a cell obtained by gene recombination technique and the like.

The cell which is naturally present in the human body includes a cell expressing the polypeptide in the body of a cancer patient, such as a cell expressing the polypeptide among tumor cells obtained by biopsy or the like.

The cell line established from the cell which is naturally present in the human body includes a cell line expressing the polypeptide among the cell lines obtained by establishing die above-described cells expressing the polypeptide obtained from a cancer patient, such as a pancreatic cancer cell line Capan-2 (ATCC IITB-80) or HPAF-II (ATCC CRL-1997).

The cell obtained by gene recombination technique includes, for example, a cell expressing die polypeptide, which is prepared by introducing an expression vector comprising cDNA encoding the polypeptide into an insect cell, an animal cell, etc., and the like.

Also, the present invention relates to a monoclonal antibody which binds to an extracellular region of CLDN4 and has neutralizing activity for CLDN4.

The neutralizing activity for CLDN4 in the present invention means the activity of inhibiting activity of CLDN4. The activity of CLDN4 includes intracellular adhesion activity by forming TJ, activity as a barrier for inhibiting free pass of water-soluble molecules through the gaps between epithelial cells and vascular endothelial cells [*Natl. Rev. Mol. Cell. Biol.*, 2, 285 (2001), *J. Cell Biol.*, 147, 195 (1999)], activity relating to canceration and malignant alteration of cancer, and the like. The activity relating to canceration and malignant alteration of cancer includes activity for accelerating activity of cancer cells such as tumor forming ability, infiltration ability and metastasis causing ability, and the like [*Cancer Res.*, 65, 7378 (2005)].

The antibody of the present invention may be any antibody, so long as it is an antibody or an antibody fragment thereof, which specifically recognizes three-dimensional structure of an extracellular region of CLDN4 and binds to the extracellular region or an antibody or an antibody fragment thereof, which binds to an extracellular region of CLDN4 and has neutralizing activity for CLDN4. Examples include an antibody which recognizes three-dimensional structure of either amino acid sequence of the amino acid sequences at positions 28 to 76 and positions 141 to 159 in the amino acid sequence represented by SEQ ID NO:2.

The antibody which recognizes the three-dimensional structure of the amino acid sequence at positions 28 to 76 in the amino acid sequence represented by SEQ ID NO:2 includes a monoclonal antibody KM3907 produced by a hybridoma KM3907 (FERM BP-10885), an antibody which competes with the monoclonal antibody KM3907 in the binding to the extracellular region of CLDN4, an antibody which binds to an epitope in the extracellular region of CLDN4 to which the monoclonal antibody KM3907 binds, and the like.

The antibody which recognizes the three-dimensional structure of the amino acid sequence at positions 141 to 159 in the amino acid sequence represented by SEQ ID NO:2 includes a monoclonal antibody KM3900 produced by a hybridoma KM3900 (FERM BP-10751), an antibody which competes with the monoclonal antibody KM3907 in the binding to the extracellular region of CLDN4, an antibody which binds to an epitope in the extracellular region of CLDN4 to which the monoclonal antibody KM3900 binds, and the like.

The monoclonal antibody of the present invention includes an antibody produced by a hybridoma and a recombinant antibody produced by a transformant transformed with an expression vector containing a gene encoding an antibody.

A hybridoma is a cell producing a monoclonal antibody having desired immunospecificity which is obtained by cell fusion of a B cell obtained by immunizing a non-human mammal with an antigen, with a myeloma cell.

The hybridoma can be prepared, for example, by preparing the above cell expressing CLDN4 as an antigen, inducing an antibody-producing cell having antigen specificity from an animal immunized with the antigen, and fusing the antigen-producing cell with a myeloma cell. The anti-CLDN4 antibody can be obtained by culturing the hybridoma or administering the hybridoma cell into an animal to cause ascites tumor in the animal and separating and purifying the culture or the ascites.

The animal immunized with an antigen may be any animals so long as a hybridoma can be prepared, and mouse, rat, hamster, rabbit or the like is suitably used. Also, the cell having antibody-producing activity can be obtained from such an animal, and the antibody of the present invention includes an antibody produced by a hybridoma obtained by fusion of the cell after in vitro immunization with a myeloma cell.

The monoclonal antibody is an antibody secreted by a single clone antibody-producing cell, and recognizes only one epitope (also called antigen determinant) and has uniform amino acid sequence (primary structure).

Examples of the monoclonal antibody of the present invention include a monoclonal antibody KM3900 produced by a hybridoma KM3900, a monoclonal antibody which binds to the cellular extraregion of CLDN4 by competing with the monoclonal antibody KM3900, a monoclonal antibody which binds to an epitope in the extracellular region of CLDN4 bound to the monoclonal antibody KM3900, and the like.

Furthermore, examples of the monoclonal antibody of the present invention include a monoclonal antibody KM3907 produced by a hybridoma KM3907, a monoclonal antibody which binds to the cellular extraregion of CLDN4 by competing with the monoclonal antibody KM3907, a monoclonal antibody which binds to an epitope in the extracellular region of CLDN4 bound to the monoclonal antibody KM3907, and the like.

The hybridoma KM3900 has been deposited to International Patent Organism Depositary, National Institute of Advanced Industrial Science and Technology under the Budapest Treaty as FERM BP-10751 on Dec. 21, 2006. Also, the hybridoma KM3907 has been deposited to International Patent Organism Depositary, National Institute of Advanced Industrial Science and Technology under the Budapest Treaty as FERM BP-10885 on Jul. 31, 2007.

The recombinant antibody includes an antibody produced by gene recombination, such as a human chimeric antibody, a humanized antibody, a human antibody and an antibody fragment thereof. Among the recombinant antibodies, one having antigen binding activity, low immunogenecity and prolonged half-life in blood is preferable as a therapeutic agent.

Examples of the recombinant antibody of the present invention include a recombinant antibody in which CDR1, CDR2 and CDR3 of VH of the antibody comprise the amino acid sequences represented by SEQ ID NOs:19, 20 and 21, respectively; a recombinant antibody in which CDR1, CDR2 and CDR3 of VL of the antibody comprise the amino acid sequences represented by SEQ ID NOs:22, 23 and 24, respectively, and a recombinant antibody in which CDR1, CDR2 and CDR3 of VH of the antibody comprise the amino acid sequences represented by SEQ ID Nos:19, 20 and 21, respectively, and CDR1, CDR2 and CDR3 of VL of the antibody comprise the amino acid sequences represented by SEQ ID NOs:22, 23 and 24, respectively; and the like.

Also, examples of the recombinant antibody of the present invention include a recombinant antibody in which CDR1, CDR2 and CDR3 of VH of the antibody comprise the amino acid sequences represented by SEQ ID NOs:59, 60 and 61, respectively; a recombinant antibody in which CDR1, CDR2 and CDR3 of VL of the antibody comprise the amino acid sequences represented by SEQ ID NOs:62, 63 and 64, respectively, and a recombinant antibody in which CDR1, CDR2 and CDR3 of VH of the antibody comprise the amino acid sequences represented by SEQ ID NOs:59, 60 and 61 respectively, and CDR1, CDR2 and CDR3 of VL of the antibody comprise the amino acid sequences represented by SEQ ID NOs:62, 63 and 64, respectively; and the like.

Furthermore, examples of the recombinant antibody of the present invention include a recombinant antibody which competes with a monoclonal antibody KM3900 in the binding to the extracellular region of CLDN4, a recombinant antibody which competes with a monoclonal antibody KM3907 in the binding to the extracellular region of CLDN4, a recombinant antibody which binds to an epitope in the extracellular region of CLDN4 recognized by a monoclonal antibody KM3900, and a recombinant antibody which binds to an epitope in the extracellular region of CLDN4 recognized by a monoclonal antibody KM3907.

The human chimeric antibody is an antibody comprising a heavy chain variable region (hereinafter referred to as "VH") and a light chain variable region (hereinafter referred to as "VL") of an antibody of a non-human animal and a heavy chain constant region (hereinafter referred to as "CH") and a light chain constant region (hereinafter referred to as "CL") of a human antibody.

The human chimeric antibody of the present invention can be produced as follows. Specifically, the human chimeric antibody can be produced by obtaining cDNAs encoding VH and VL from a hybridoma which produces a monoclonal antibody which specifically recognizes three-dimensional structure of CLDN4 and binds to the extracellular region or a monoclonal antibody which specifically recognizes three-dimensional structure of CLDN4 and has neutralizing activity for CLDN4, inserting each of them into an expression vector for animal cell comprising DNAs encoding CH and CL of human antibody to thereby construct a vector for expression of human chimeric antibody, and then introducing die vector into an animal cell to express the antibody.

As the CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of the human chimeric antibody, any CL can be used, so long as it belongs to the hIg class, and those belonging to κ class or λ class can be used.

Examples of the human chimeric antibody of the present invention includes a human chimeric antibody in which CDR1, CDR2 and CDR3 of VH of the antibody comprise the amino acid sequences represented, by SEQ ID NOs:19, 20 and 21, respectively, and CDR1, CDR2 and CDR3 of VL of the antibody comprise the amino acid sequences represented by SEQ ID NOs:22, 23 and 24, respectively; a human chimeric antibody in which VH of the antibody comprises the amino acid sequence at positions 20 to 142 in the amino acid sequence represented by SEQ ID NO:16, and VL of the antibody comprises the amino acid sequence at positions 23 to 130 in the amino acid sequence represented by SEQ ID NO:18; and the like.

Also, examples of the human chimeric antibody of the present invention includes a human chimeric antibody in which CDR1, CDR2 and CDR3 of VH of the antibody comprise the amino acid sequences represented by SEQ ID NOs: 59, 60 and 61, respectively, and CDR1, CDR2 and CDR3 of VL of the antibody comprise the amino acid sequences represented by SEQ ID NOs:62, 63 and 64, respectively; and a human chimeric antibody in which VH of the antibody comprises the amino acid sequence at positions 20 to 138 in the amino acid sequence represented by SEQ ID NO:56, and VL of the antibody comprises the amino acid sequence at positions 23 to 130 in the amino acid sequence represented by SEQ ID NO:58.

A humanized antibody is an antibody in which amino acid sequences of CDRs of VH and VL of an antibody derived from a nonhuman animal are grafted into appropriate positions of VH and VL of a human antibody, and is also called a human CDR-grafted antibody or a reshaped-antibody.

The humanized antibody of the present invention can be produced by constructing cDNAs encoding an antibody variable region (hereinafter referred to as "V region") in which the amino acid sequences of CDRs of VH and VL of an antibody derived from a non-human animal produced by a hybridoma which produces a monoclonal antibody which specifically recognizes three-dimensional structure of CLDN4 and binds to the extracellular region or a monoclonal antibody which binds to an extracellular region of CLDN4 and has neutralizing activity for CLDN4 in the present invention are grafted into frameworks (hereinafter referred to as "FR") of VH and VL of any human antibody, inserting each of them into a vector for expression of animal cell comprising genes encoding CH and CL of a human antibody to thereby construct a vector for expression of humanized antibody, and introducing it into an animal cell to thereby express and produce the humanized antibody.

As the amino acid sequences of FRs of VH and VL of a human antibody, any amino acid sequences can be used, so long as they are amino acid sequences of VH and VL, respectively, derived from a human antibody. Examples include amino acid sequences of VH and VL of human antibodies registered in database such as Protein Data Bank, common amino acid sequences of each sub group of FRs of VH and VL of human antibodies described in, for example, *Sequences of Proteins of Immunological Interest*; US Dept. Health and Human Services (1991), and the like.

As the CH of the humanized antibody, any CH can be used, so long as it belongs to the hIg class, and those of the hIgG class are preferred and any one of the subclasses belonging to the hIgG class, such as hIgG1, hIgG2, hIgG3 and hIgG4 can be used. As the CL of the humanized antibody, any CL can be used, so long as it belongs to the hIg class, and those belonging to the κ class or λ class can be used.

Examples of the humanized antibody of the present invention include a humanized antibody or an antibody fragment thereof wherein CDR1, CDR2 and CDR3 of VH of the antibody comprise die amino acid sequences represented by SEQ ID NOs:19, 20 and 21 respectively, and/or CDR1, CDR1(2 and CDR3 of VL of the antibody comprise the amino acid sequences represented by SEQ ID NOs:22, 23 and 24, respectively, a humanized antibody or an antibody fragment thereof wherein CDR1, CDR2 and CDR3 of VH of the antibody comprise the amino acid sequences represented by SEQ ID NOs:59, 60 and 61 respectively, and/or CDR1, CDR2 and CDR3 of VL of the antibody comprise the amino acid sequences represented by SEQ ID NOs:62, 63 and 64, respectively, and the like.

Specific examples of the humanized antibody include a humanized antibody wherein VH of the antibody comprises the amino acid sequence represented by SEQ ID NO:74 or an amino acid sequence in which at least one modification among amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val is introduced in the amino acid sequence represented by SEQ ID NO:74, and VL of the antibody comprises the amino acid sequence represented by SEQ ID NO:76 or an amino acid sequence in which at least one modification among amino acid modifications for substituting Asp at position 1 with Gln, Ser at position 10 with Ile, Ile at position 21 with Met, Lea at position 48 with Trp, Asp at position 71 with Ser, Leu at position 79 with Met and Pro at position 81 with Ala is introduced in the amino acid sequence represented by SEQ ID NO:76; and the like.

For example, the following humanized antibodies are included:

regarding the amino acid sequence of VH of the antibody, a humanized antibody wherein VH of the antibody comprises an amino acid sequence in which Pro at position 41, Sly at position 44, Met at position 48, Arg at position 67, Val at position 68, Ile at position 70 and Ala at position 72 in the amino acid sequence represented by SEQ ID NO:74 are substituted with other amino acid residues, preferably, a humanized antibody wherein VH of the antibody comprises an amino acid sequence in which Met at position 48, Arg at position 67, Val at position 68, Ile at position 70 and Ala at position 72 in the amino acid sequence represented by SEQ ID NO:74 are substituted with other amino acid residues, preferably, a humanized antibody wherein VH of the antibody comprises an amino acid sequence in which Met at position 48, Val at position 68, Ile at position 70 and Ala at position 72 in the amino acid sequence represented by SEQ ID NO:74 are substituted with other amino acid residues, preferably, a humanized antibody wherein VH of the antibody comprises an amino acid sequence in which Val at position 68, Ile at position 70 and Ala at position 72 in the amino acid sequence represented by SEQ ID NO:74 are substituted with other amino acid residues, preferably, a humanized antibody wherein VH of Me antibody comprises an amino acid sequence in which Met at position 48, Val at position 68 and Ile at position 70 in the amino acid sequence represented by SEQ ID NO:74 are substituted with other amino acid residues, preferably, a humanized antibody wherein VH of the antibody comprises an amino acid sequence in which Val at position 68 and Ile at position 70 in the amino acid sequence represented by SEQ ID NO:74 are substituted with other amino acid residues, and the like.

The amino acid sequence of VH of the antibody obtained by the above amino acid modifications includes an amino acid sequence in which at least one modification among amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val is introduced in the amino acid sequence represented by SEQ ID NO:74.

Examples of the amino acid sequence of VH in which eight modifications are introduced include an amino acid sequence in which substitutions of Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val are introduced in the amino acid sequence represented by SEQ ID NO:74.

Examples of the amino acid sequence of VH in which seven modifications are introduced include an amino acid sequence in which substitutions of Pro at position 41 with His, Gly at position 44 with Ser, Met at position 48 with Ile, Arg at position 67 with Lys, Val at position 68 with Ala, Ile at position 70 with Leu and Ala at position 72 with Val are introduced in the amino acid sequence represented by SEQ ID NO:74, and the like.

Examples of the amino acid sequence of VH in which six modifications are introduced include an amino acid sequence in which substitutions of Gly at position 44 with Ser, Met at position 48 with Ile, Arg at position 67 with Lys, Val at position 68 with Ala, Ile at position 70 with Leu and Ala at position 72 with Val are introduced, an amino acid sequence in which substitutions of Pro at position 41 with His, Met at position 48 with Ile, Val at position 68 with Ala, Ile at position 70 with Leu and Ala at position 72 with Val are introduced, and an amino acid sequence in which substitutions of Pro at position 41 with His, Gly at position 44 with Ser, Met at position 48 with Ile, Val at position 68 with Ala, Ile at position 70 with Leu and Ala at position 72 with Val are introduced in the amino acid sequence represented by SEQ ID NO:74, and the like.

Examples of the amino acid sequence of VH in which five modifications are introduced include an amino acid sequence in which substitutions of Met at position 48 with Ile, Arg at position 67 with Lys, Val at position 68 with Ala, Ile at position 70 with Leu and Ala at position 72 with Val are introduced, an amino acid sequence in which substitutions of Pro at position 41 with His, Met at position 48 with Ile, Arg at position 67 with Lys, Val at position 68 with Ala, Ile at position 70 with Leu and Ala at position 72 with Val are introduced, and an amino acid sequence in which substitutions of Gly at position 44 with Ser, Met at position 48 with Ile, Val at position 68 with Ala, Ile at position 70 with Leu and Ala at position 72 with Val are introduced in the amino acid sequence represented by SEQ ID NO:74, and the like.

Examples of the amino acid sequence of VH in which four modifications are introduced include an amino acid sequence in which substitutions of Met at position 48 with Ile, Val at position 68 with Ala, Ile at position 70 with Leu and Ala at position 72 with Val are introduced in the amino acid sequence represented by SEQ ID NO:74, and the like.

Examples of the amino acid sequence of VH in which three modifications are introduced include an amino acid sequence in which substitutions of Val at position 68 with Ala, Ile at position 70 with Leu and Ala at position 72 with Val are introduced, an amino acid sequence in which substitutions of Met at position 48 with Ile, Ile at position 70 with Leu and Ala at position 72 with Val are introduced, an amino acid sequence in which substitutions of Met at position 48 with Ile, Val at position 68 with Ala and Ala at position 72 with Val are introduced, and an amino acid sequence in which substitutions of Met at position 48 with Ile, Val at position 68 with Ala and Ile at position 70 with Leu are introduced in the amino acid sequence represented by SEQ ID NO:74, and the like.

Examples of the amino acid sequence of VH in which two modifications are introduced include an amino acid sequence in which substitutions of Ile at position 70 with Leu and Ala at position 72 with Val are introduced, an amino acid sequence in which substitutions of Met at position 48 with Ile and Ala at position 72 with Val are introduced, an amino acid sequence in which substitutions of Met at position 48 with Ile and Val at position 68 with Ala are introduced, and an amino acid sequence in which substitutions of Val at position 68 with Ala and Ile at position 70 with Leu are introduced in the amino acid sequence represented by SEQ ID NO:74, and the like.

Examples of the amino acid sequence of VH in which one modification is introduced include an amino acid sequence in which Pro at position 41 is substituted with His, an amino acid sequence in which Gln at position 43 is substituted with Lys, an amino acid sequence in which Gly at position 44 is substituted with Ser, an amino acid sequence in which Met at position 48 is substituted with Ile, an amino acid sequence in which Arg at position 67 is substituted with Lys, an amino acid sequence in which Val at position 68 is substituted with Ala, an amino acid sequence in which Ile at position 70 is substituted with Lea and an amino acid sequence in which Ala at position 72 is substituted with Val, in the amino acid sequence represented by SEQ ID NO:74.

Regarding VL of the antibody, examples include a humanized antibody wherein VL of the antibody comprises an amino acid sequence in which Asp at position 1, Ile at position 21, Leu at position 48, Asp at position 71, Leu at position 79 and Pro at position 81 in the amino acid sequence represented by SEQ ID NO:76 are substituted with other amino acid residues, preferably, a humanized antibody wherein VL of the antibody comprises an amino acid sequence in which Asp at position 1, Ile at position 21, Leu at position 43, Lea at position 79 and Pro at position 81 in the amino acid sequence represented by SEQ ID NO:76 are substituted with other amino acid residues, preferably, a humanized antibody wherein VL of the antibody comprises an amino acid sequence in which Asp at position 1, Ile at position 21, Leu at position 48 and Leu at position 79 in the amino acid sequence represented by SEQ ID NO:76 are substituted with other amino acid residues, preferably, a humanized antibody wherein VL of the antibody comprises an amino acid sequence in which Ile at position 21, Leu at position 48 and Leu at position 79 in the amino acid sequence represented by SEQ ID NO:76 are substituted with other amino acid residues, preferably, a humanized antibody wherein VL of the antibody comprises an amino acid sequence in which Ile at position 21 and Leu at position 48 in the amino acid sequence represented by SEQ ID NO:76 are substituted with other amino acid residues, preferably, a humanized antibody wherein VL of the antibody comprises an amino acid sequence in which Leu at position 48 and Leu at position 79 in the amino acid sequence represented by SEQ ID NO:76 are substituted with other amino acid residues, and the like.

The amino acid sequence of VL of the antibody obtained by the above amino acid modifications includes an amino acid sequence in which at least one modification among amino acid modifications for substituting Asp at position 1 with Gln, Ser at position 10 with Ile, Ile at position 21 with Met, Leu at position 48 with Trp, Asp at position 71 with Ser, Leu at position 79 with Met and Pro at position 81 with Ala is introduced in the amino acid sequence represented by SEQ ID NO:76.

Examples of the amino acid sequence of VL in which seven modifications are introduced include an amino acid sequence in which substitutions of Asp at position 1 with Gln, Ser at position 10 with Ile, Ile at position 21 with Met, Leu at position 48 with Trp, Asp at position 71 with Ser, Leu at position 79 with Met and Pro at position 81 with Ala are introduced in the amino acid sequence represented by SEQ ID NO:76.

Examples of the amino acid sequence of VL in which six modifications are introduced include an amino acid sequence in which substitutions of Asp at position 1 with Gln, Ile at position 21 with Met, Leu at position 48 with Trp, Asp at position 71 with Ser, Leu at position 79 with Met and Pro at position 81 with Ala are introduced, an amino acid sequence in which substitutions of Asp at position 1 with Gln, Ser at position 10 with Ile, Ile at position 21 with Met, Leu at position 48 with Trp, Leu at position 79 with Met and Pro at position 81 with Ala are introduced, and an amino acid sequence in which substitutions of Asp at position 1 with Gln, Ser at position 10 with Ile, Ile at position 21 with Met, Leu at position 48 with Tip, Asp at position 71 with Ser and Leu at position 79 with Met are introduced in the amino acid sequence represented by SEQ ID NO:76, and the like.

Examples of the amino acid sequence of VL in which five modifications are introduced include an amino acid sequence in which substitutions of Asp at position 1 with Gln, Ile at position 21 with Met, Leu at position 48 with Trp, Leu at position 79 with Met and Pro at position 81 with Ala are introduced, an amino acid sequence in which substitutions of Asp at position 1 with Gln, Ile at position 21 with Met, Leu at position 48 with Trp, Asp at position 71 with Ser and Leu at position 79 with Met are introduced, and an amino acid sequence in which substitutions of Asp at position 1 with Gln, Ser at position 10 with Ile, Ile at position 21 with Met, Leu at position 48 with Tip and Leu at position 79 with Met are introduced in the amino acid sequence represented by SEQ ID NO:76, and the like.

Examples of the amino acid sequence of VL in which four modifications are introduced include an amino acid sequence in which substitutions of Asp at position 1 with Gln, Ile at position 21 with Met, Leu at position 48 with Trp and Leu at position 79 with Met are introduced in the amino acid sequence represented by SEQ ID NO:76, and the like.

Examples of the amino acid sequence of VL in which three modifications are introduced include an amino acid sequence in which substitutions of Ile at position 21 with Met, Leu at position 48 with Trp and Leu at position 79 with Met are introduced in the amino acid sequence represented by SEQ ID NO:76, and the like.

Examples of the amino acid sequence of VL in which two modifications are introduced include an amino acid sequence in which substitutions of Leu at position 48 with Trp and Leu at position 79 with Met are introduced, an amino acid sequence in which substitutions of Ile at position 21 with Met and Leu at position 79 with Met are introduced, an amino acid sequence in which substitutions of Ile at position 21 with Met and Leu at position 48 with Trp are introduced in the amino acid sequence represented by SEQ ID NO:76, and the like.

Examples of the amino acid sequence of VL in which one modification is introduced include an amino acid sequence in which Asp at position 1 is substituted with Gln, an amino acid sequence in which Ser at position 10 is substituted with Ile, an amino acid sequence in which Ile at position 21 is substituted with Met, an amino acid sequence in which Leu at position 48 is substituted with Trp, an amino acid sequence in which Asp at position 71 is substituted with Ser, an amino acid sequence in which Leu at position 79 is substituted with Met and an amino acid sequence in which Pro at position 81 is substituted with Ala in the amino acid sequence represented by SEQ ID NO:76.

A human antibody is originally an antibody naturally existing in the human body, and it also includes antibodies obtained from a human antibody phage library or a human antibody-producing transgenic animal, which is prepared based on the recent advance in genetic engineering, cell engineering and developmental engineering techniques.

The antibody existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the supernatant of the culture.

In the amino acid sequence constituting the above antibody or antibody fragment, an antibody or antibody fragment thereof in which one or more amino acids are deleted, substituted, inserted or added, having activity similar to the above antibody or antibody fragment is also included in the antibody or antibody fragment of the present invention.

The number of amino acids which are deleted, substituted, inserted and/or added is one or more, and is not specifically limited, but it is within the range where deletion, substitution or addition is possible by known methods such as the site-directed mutagenesis described in *Molecular Cloning*, Second Edition; *Current Protocols in Molecular Biology; Nucleic Acids Research*, 10, 6487 (1982), *Proc. Natl. Acad. Sci. USA*, 79, 6409 (1982); Gene, 34, 315 (1985), *Nucleic Acids Research*, 13, 4431 (1985); *Proc. Natl. Acad. Sci. USA*, 82, 488 (1985) or the like. For example, the number is 1 to dozens, preferably 1 to 20, more preferably 1 to 10, and most preferably 1 to 5.

The expression "one or more amino acids are deleted, substituted, inserted or added" in the amino acid sequence of the above antibody means the followings. That is, it means there is deletion, substitution, insertion or addition of one or plural amino acids at optional positions in the same sequence and one or plural amino acid sequences. Also, the deletion, substitution, insertion or addition may occur at the same time and the amino acid which is substituted, inserted or added may be either a natural type or a non-natural type. The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine
Group B: aspartic acid, glutamic acid, isoaspartic acid, isoglutamic acid, 2-aminoadipic acid, 2-aminosuberic acid
Group C: asparagine, glutamine
Group D: lysine, arginine, ornithine, 2,4-diaminobutanoic acid, 2,3-diaminopropionic acid
Group E: proline, 3-hydroxyproline, 4-hydroxyproline
Group F: serine, threonine, homoserine
Group G: phenylalanine, tyrosine The antibody fragment of the present invention includes Fab, Fab', F(ab')$_2$, scFv, diabody, dsFv and the like.

The antibody fragment of the present invention includes Fab, Fab', F(ab')$_2$, scFv, diabody, dsFv, a peptide comprising CDR and the like.

An Fab is an antibody fragment having a molecular weight of about 50,000 and having antigen binding activity, in which about a half of the N-terminal side of H chain and the entire L chain, among fragments obtained by treating an IgG antibody molecule with a protease, papain (cleaved at an amino acid residue at position 224 of the H chain), are bound together through a disulfide bond.

The Fab of the present invention can be produced by treating a monoclonal antibody which specifically recognizes three-dimensional structure of an extracellular region of CLDN4 and binds to the extracellular region or a monoclonal antibody which binds to an extracellular region of CLDN4 and has neutralizing activity for CLDN4 with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is all antibody fragment having a molecular weight of about 100,000 and antigen binding activity and comprising two Fab regions which are bound in the hinge position obtained by digesting the lower part of two disulfide bonds in the hinge region of IgG, with an enzyme, pepsin.

The F(ab')$_2$ of the present invention can be produced by treating a monoclonal antibody which specifically recognizes three-dimensional structure of an extracellular region of CLDN4 and binds to the extracellular region or a monoclonal antibody which binds to an extracellular region of CLDN4 and has neutralizing activity for CLDN4 with a protease, pepsin. Also, the F(ab')$_2$ can be produced by binding Fab' described below via a thioether bond or a disulfide bond.

An Fab' is an antibody fragment having a molecular weight of about 50,000 and antigen binding activity, which is obtained by cleaving a disulfide bond at the hinge region of the above F(ab')$_2$.

The Fab' of the present invention can be produced by F(ab')$_2$ which specifically recognizes three-dimensional structure of an extracellular region of CLDN4 and binds to the extracellular region or F(ab')$_2$ which binds to an extracellular region of CLDN4 and has neutralizing activity for CLDN4, with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity.

The scFv of the present invention can be produced by obtaining cDNAs encoding VH and VL of a monoclonal antibody which specifically recognizes three-dimensional structure of an extracellular region of CLDN4 and binds to the extracellular region or a monoclonal antibody which binds to an extracellular region of CLDN4 and has neutralizing activity for CLDN4, constructing DNA encoding scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, and has divalent antigen binding activity. In the divalent antigen binding activity, two antigens may be the same or different.

The diabody of the present invention can be produced by obtaining cDNAs encoding VH and VL of a monoclonal antibody which specifically recognizes three-dimensional structure of an extracellular region of CLDN4 and binds to the extracellular region or a monoclonal antibody which binds to an extracellular region of CLDN4 and has neutralizing activity for CLDN4, constructing DNA encoding scFv so that the length of the amino acid sequence of P is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. [*Protein Engineering*, 7, 697 (1994)].

The dsFv of the present invention can be produced by obtaining cDNAs encoding VH and VL of a monoclonal antibody which specifically recognizes three-dimensional structure of an extracellular region of CLDN4 and binds to the extracellular region or a monoclonal antibody which binds to an extracellular region of CLDN4 and has neutralizing activity for CLDN4, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one region or more of CDRs of VH or VL. Peptide comprising plural CDRs can be bound directly or via an appropriate peptide linker.

The peptide comprising CDR of the present invention can be produced by constructing DNA encoding CDRs of VH and VL of a monoclonal antibody which specifically recognizes three-dimensional structure of an extracellular region of CLDN4 and binds to the extracellular region or a monoclonal antibody which binds to an extracellular region of CLDN4 and has neutralizing activity for CLDN4, inserting the DNA into an expression vector for prokaryote or an expression vector for eukaryote, and then introducing the expression vector into a prokaryote or eukaryote to express the peptide.

The peptide comprising CDR can also be produced by a chemical synthesis method such as Fmoc method (fluorenylmethoxycarbonyl method) or tBoc method (t-butyloxycarbonyl method).

The antibody of the present invention includes an antibody conjugate in which a monoclonal antibody or an antibody fragment thereof which specifically recognizes three-dimensional structure of an extracellular region of CLDN4 and binds to the extracellular region or a monoclonal antibody or an antibody fragment thereof which binds to an extracellular region of CLDN4 and has neutralizing activity for CLDN4 is chemically or genetically bound to an agent, a proteins a radioisotope or the like.

The conjugate of the present invention can be produced by chemically conjugating an agent, a protein, a radioisotope or the like to the N-terminal side or C-terminal side of an H chain or an L chain of the monoclonal antibody or the antibody fragment thereof which specifically recognizes three-dimensional structure of an extracellular region of CLDN4 and binds to the extracellular region or the monoclonal antibody or the antibody fragment thereof which binds to an extracellular region of CLDN4 and has neutralizing activity for CLDN4 in the present invention, an appropriate substituent or side chain of the antibody or the antibody fragment, a sugar chain in the antibody or the antibody fragment or the like [*Antibody Engineering Handbook*, edited by Osamu Kanemitsu, published by Chijin Shokan (1994)].

Also, the conjugate can be genetically produced by linking a DNA encoding the monoclonal antibody or the antibody fragment thereof which specifically recognizes three-dimensional structure of an extracellular region of CLDN4 and binds to the extracellular region or the monoclonal antibody or the antibody fragment thereof which binds to an extracellular region of CLDN4 and has neutralizing activity for CLDN4 in the present invention to other DNA encoding a protein to be conjugated, inserting the DNA into a vector for expression, and introducing the expression vector into a host cell of a prokaryote or eukaryote.

The agent includes a chemotherapeutic agent, a therapeutic antibody, an immunostimulator, an agent having high molecular weight, and the like.

The protein includes cytokine, a growth factor, a toxic protein, and the like.

Furthermore, the agent to be conjugated to the antibody or the antibody fragment thereof may be in a form of a prodrug. The prodrug in the present invention is an agent which is subjected to chemical modification by an enzyme existing in the tumor environment and is converted to a substance having an activity of damaging the tumor cells.

The chemotherapeutic agent includes any chemotherapeutic agents such as an alkylating agent, a nitrosourea agent, a metabolism antagonist, an anticancer antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor. Examples of the chemotherapeutic agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), doxorubicin lipo (Doxyl), epirubicin, gemcitabine (Gemsal), daunorubicin, daunorubicin lipo (Daunozome), procarbazine, mitomycin, cytarabine, etoposide, methotrexate, 5-fluorouracil, fluorouracil, vinblastine, vincristine, bicomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, CPT-11, 10-hydroxy-7-ethylcamptothecin (SN38), floxuridine, fludarabine, hydroxyurea, iphosphamide, idarubicin, mesna, irinotecan, nogitecan, mitoxantrone, topotecan, leuprolide, rnegestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, Flt3 inhibitor, VEGFR inhibitor, FGFR inhibitor, radicicol, 17-allylamino-17-demethoxygeldanamycin, rapamycin, amsacrine, all-trans-retinoic acid, thalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexainethasone, progestin substances, estrogen substances, anastrozole (Arimidex), Leuplin, aspirin, indometbacin, celecoxib, azathioprine, penicillamine, gold thiomalate, chlorpheniramine maleate, chlorpheniramine, clemastine, tretinoin, bexarotene, arsenic, voltezomib, allopurinol, gemtuzumab, ibritumomab tiuxetan, 131 tositumomab, Targretin, ONTAK, ozogamine, clarithromycin, leucovorin, ifosfamide, ketoconazole, aminoglutethimide, suramin, methotrexate, maytansinoid and derivatives thereof.

The method for conjugating the chemotherapeutic agent with the antibody includes a method in which the chemotherapeutic agent and an amino group of the antibody are conjugated via glutaraldehyde, a method in which an amino group of the chemotherapeutic agent and a carboxyl group of the antibody are bound via water-soluble carbodiimide, and the like.

The therapeutic antibody includes an antibody against an antigen in which apoptosis is induced by binding of the antibody, an antibody against an antigen participating in formation of morbid state of tumor, an antibody which regulates immunological function and an antibody relating to angiogenesis in the morbid part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, EGFR and the like.

The antigen for the antibody which regulates immunological function includes CD4, CD40, CD40 ligand, B7 family molecule (CD80, CD86, CD274, B7-DC, B7-H2, B7-H3, B7-H4), ligand of B7 family molecule (CD28, CTLA-4, ICOS, PD-1, BTLA), OX-40, OX-40 ligand, CD137, tumor necrosis factor (TNF) receptor family molecule (DR4, DR5, TNFR1, TNFR2), TNF-related apoptosis-inducing ligand receptor (TRAIL) family molecule, receptor family of TRAIL family molecule (TRAIL-R1, TRAIL-R2, TRAIL-R3, TRAIL-R4), receptor activator of nuclear factor kappa B ligand (RANK), RANK ligand, CD25, folic acid receptor 4, cytokine [interleukin-1α (hereinafter interleukin is referred to as "IL"), IL-1β, IL-4, IL-5, IL-6, IL-10, IL-13, transforming growth factor (TGF) β, TNFα, etc.], receptors of these cytokines, chemokine (SLC, ELC, I-309, TARC, MDC, CTACK, etc.) and receptors of these chemokines.

The antigen for the antibody which inhibits angiogenesis in the morbid part includes vascular endothelial growth factor (VEGF), angiopoietin, fibroblast growth factor (FGF), EGF platelet-derived growth factor (PDGF), insulin-like growth factor (IGF), erythropoictin (EPO), TGFβ, IL-8, ephilin, SDF-1 and the like.

The immunostimulator may be any natural products known as immunoadjuvants. Examples of an agent enhancing immunogen include β(1→3)glucan (lentinan, schizophyllan), α-galactosylceramide (KRN7000), fangus powder (picibanil, BCG) and fungus extract (krestin).

The agent having high molecular weight includes polyethylene glycol (hereinafter referred to as "PEG"), albumin, dextran, polyoxyethlylene, styrene-maleic acid copolymer, polyvinylpyrrolidone, pyran copolymer, hydroxypropylmethacrylamide, and the like. By binding these compounds having high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [*Bioconjugate Drug*, Hirokawa Shoten (1993)]. For example, the method for binding PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No, 23587/81), a modifying agent of a guanidino group of arginine (Japanese Published Unexamined Patent Application No. 117920/90) and the like.

The cytokine or the growth factor may be any cytokine or growth factor, so long as it enhances cells such as NK cells, macrophages and neutrophils. Examples include interferon (hereinafter referred to as "INF")-α, INF-β, INF-γ, IL-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like.

The toxic protein includes ricin, diphtheria toxin, ONTAK and the like, and also includes a toxic protein wherein mutation is introduced into a protein in order to control the toxicity.

The radioisotope includes $^{131}$I, $^{125}$I, $^{90}$Y, $^{64}$Cu, $^{199}$Tc, $^{77}$Lu, $^{211}$At and the like. The radioisotope can directly be conjugated with the antibody by Chloramine-T method. Also, a substance chelating the radioisotope can be conjugated with the antibody. The chelating agent includes methylbenzyldiethylene-triaminepentaacetic acid (MX-DTPA) and the like.

In the present invention, the antibody used in the present invention can be administered in combination with one or more of other agents, and radiation irradiation can be also used in combination. The other agent includes the above-described chemotherapeutic agent, therapeutic antibody, immunostimulator such as cytokine, and the like.

The radiation irradiation includes photon (electromagnetic) irradiation such as X-ray or γ-ray, particle irradiation such as electron beam, proton beam or heavy particle beam, and the like In the method for combined administration, the agent may be simultaneously administered with the antibody used in the present invention, or the agent may be administered before or after the administration of the antibody used in the present invention.

The detection method, determination method, detection reagent determination reagent or diagnostic agent in the present invention include a method in which a specified label is used by labeling the antibody of the present invention. The label includes a label which is used in the general immunological detection or measuring method, and examples include enzymes such as alkaline phosphatase, peroxidase and luciferase, luminescent materials such as acridinium ester and lophine, fluorescent materials such as fluorescein isothiocyanate (FITC) and RITC, and the like.

The monoclonal antibody which specifically recognizes three-dimensional structure of an extracellular region of CLDN4 and binds to the extracellular region and the monoclonal antibody which binds to an extracellular region of CLDN4 and has neutralizing activity for CLDN4 in the present invention includes a monoclonal antibody which specifically recognizes three-dimensional structure of an extracellular region of CLDN4 and binds to the extracellular region of CLDN4, wherein the monoclonal antibody specifically recognizes three-dimensional structure of an extracellular region of a polypeptide encoded by CLDN3 gene (hereinafter the polypeptide encoded by CLDN3 is also referred to as "CLDN3") and binds to the extracellular region of CLDN3, and a monoclonal antibody which specifically binds to an extracellular region of CLDN4 and has neutralizing activity for CLDN4, wherein the monoclonal antibody specifically recognizes three-dimensional structure of an extracellular region of CLDN3 and binds to the extracellular region of CLDN3.

The extracellular region of CLDN3 includes, for example, regions predicted from the amino acid sequence of the polypeptide represented by SEQ ID NO:26 by using conventionally known transmembrane region deducing program SOSUI, predicting program TMHMM ver. 2 ExPASy Proteomics Server or the like.

Examples of the extracellular region of the polypeptide encoded by CLDN3 gene in the present invention include regions corresponding to positions 30 to 80 and 137 to 159 in the extracellular domain predicted by ExPASy Proteomics Server or positions 27 to 75 and 140 to 158 in the extracellular domain predicted in a reference [*Cancer Immunol. Immunother.*, 54, 431-445 (2005)].

The monoclonal antibody which specifically recognizes three-dimensional structure of an extracellular region of CLDN4 and binds to the extracellular region of CLDN4, wherein the monoclonal antibody specifically recognizes three-dimensional structure of an extracellular region of CLDN3 and binds to the extracellular region of CLDN3 in the present invention is not limited, so long as it specifically recognizes three-dimensional structures of extracellular regions of both of CLDN3 and CLDN4 and binds to both of the extracellular regions, and includes, for example, an anti-CLDN4 monoclonal antibody KM3907 produced by a hybridoma KM3907.

Also, the monoclonal antibody which specifically binds to an extracellular region of CLDN4 and has neutralizing activity for CLDN4, wherein the monoclonal antibody specifically recognizes three-dimensional structure of an extracellular region of CLDN3 and binds to the extracellular region of CLDN3 in the present invention is not limited, so long as it specifically recognizes three-dimensional structure of an extracellular region of CLDN3, binds to the extracellular regions of both of CLDN3 and CLDN4 and has neutralizing activity for CLDN4, and includes an anti-CLDN4 monoclonal antibody KM3907 produced by a hybridoma KM3907. The hybridoma KM3907 has been deposited to International Patent Organism Depositary, National Institute of Advanced Industrial Science and Technology under the Budapest Treaty as FERM BPs 10885 on Jul. 31, 2007.

The monoclonal antibody which specifically recognizes three-dimensional structure of an extracellular region of CLDN4 and binds to the extracellular region of CLDN4, wherein the monoclonal antibody specifically recognizes three-dimensional structure of an extracellular region of CLDN3 and binds to the extracellular region of CLDN3 in the present invention, can be prepared by selecting a monoclonal antibody which further recognizes three-dimensional structure of an extracellular region of CLDN3 and binds to the extracellular region of CLDN3 from the above-described monoclonal antibodies which specifically recognize three-dimensional structure of an extracellular region of CLDN4 and bind to the extracellular region of CLDN4.

The monoclonal antibody which specifically binds to an extracellular region of CLDN4 and has neutralizing activity for CLDN4, wherein the monoclonal antibody specifically recognizes three-dimensional structure of an extracellular region of CLDN3 and binds to the extracellular region of CLDN3 in the present invention, can be prepared by selecting a monoclonal antibody which further recognizes three-dimensional structure of an extracellular region of CLDN3 and binds to the extracellular region of CLDN3 from the above-described monoclonal antibodies which specifically recognize three-dimensional structure of an extracellular region of CLDN4 and has neutralizing activity for CLDN4.

The monoclonal antibody which specifically recognizes three-dimensional structure of an extracellular region of CLDN4 and binds to the extracellular region of CLDN4, wherein the monoclonal antibody specifically recognizes three-dimensional structure of an extracellular region of CLDN3 and binds to the extracellular region of CLDN3 and the monoclonal antibody which specifically binds to an extracellular region of CLDN4 and has neutralizing activity for CLDN4, wherein the monoclonal antibody specifically recognizes three-dimensional structure of an extracellular region of CLDN3 and binds to the extracellular region of CLDN3 can be prepared in the same manner as the recombinant antibody which specifically recognizes three-dimensional structure of an extracellular region of CLDN4 and binds to an extracellular region of CLDN4 or the recombinant antibody which specifically binds to an extracellular region of CLDN4 and has neutralizing activity for CLDN4 described above.

Examples of the recombinant antibody specifically recognizes three-dimensional structure of an extracellular region of CLDN4 and binds to the extracellular region of CLDN4, wherein the recombinant antibody specifically recognizes three-dimensional structure of an extracellular region of CLDN3 and binds to the extracellular region of CLDN3 in the present invention include a recombinant antibody in which CDR1, CDR2 and CDR3 of VH of the antibody comprise the amino acid sequences represented by SEQ ID NOs:59, 60 and 61, respectively; a recombinant antibody in which CDR1, CDR2 and CDR3 of VL of the antibody comprise the amino acid sequences represented by SEQ ID NOs:62, 63 and 64, respectively; a recombinant antibody in which CDR1, CDR2 and CDR3 of VH of the antibody comprise the amino acid sequences represented by SEQ ID NOs:59, 60 and 61, respectively, and CDR1, CDR2 and CDR3 of VL of the antibody comprise the amino acid sequences represented by SEQ ID NOs:62, 63 and 64, respectively; a recombinant antibody which competes with anti-CLDN4 monoclonal antibody KM3907 in the binding to the extracellular region of CLDN4; a recombinant antibody which binds to an epitope in the extracellular region of CLDN4 which is recognized by the monoclonal antibody KM3907; and a recombinant antibody in which VH of the antibody comprises the amino acid sequence at positions 20 to 138 in the amino acid sequence represented by SEQ ID NO:56, and/or VL of the antibody comprises the amino acid sequence at positions 23 to 130 in the amino acid sequence represented by SEQ ID NO:58.

The production process of the antibody of the present invention is described below in detail.

1. Preparation of Monoclonal Antibody (1) Preparation of Antigen

An expression vector comprising cDNA encoding a full length of CLDN4 or a partial length thereof is introduced into *Escherichia coli*, yeast, an insect cell, an animal cell or the like for expression to obtain CLDN4 or a cell expressing CLDN4 as an antigen. Also, CLDN4 can be purified from various human tumor culturing cells, human tissue and the like which express a large amount of CLDN4, and they themselves can be used as antigens. Furthermore, a synthetic peptide having a partial sequence of the CLDN4 can be prepared and used as an antigen.

The polypeptide used in the present invention can be produced, for example, by expressing a DNA encoding the polypeptide in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like according to the following method.

Firstly, a recombinant vector is prepared by introducing a full length cDNA into downstream of a promoter of an appropriate expression vector. At this time, if necessary, a DNA fragment having an appropriate length containing a region encoding the polypeptide based on the full length cDNA, and the DNA fragment may be used instead of the above full length cDNA. Next, a transformant producing the polypeptide can be obtained by introducing the recombinant vector into a host cell suitable for the expression vector.

The host cell may be any one, so long as it can express the gene of interest, and includes *Escherichia coli*, an animal cell and the like.

The expression vector includes vectors which can replicate autonomously in the host cell to be used or vectors which can be integrated into a chromosome comprising an appropriate promoter at such a position that the DNA encoding the polypeptide can be transcribed.

When a prokaryote such as *Escherichia coli* is used as the host cell, it is preferred that the recombinant vector is autonomously replicable in the prokaryote and contains a promoter, a ribosome binding sequence, the DNA used in the present invention and a transcription termination sequence. The recombinant vector may further comprise a gene regulating the promoter.

The expression vector includes, for example, pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. Nos. 4,686,191, 4,939,094, 5,160,735), pSupex, pUB110, pTP5, pC194, pEG400 [*J.*

*Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides). In the nucleotide sequence of DNA encoding the polypeptide used in the present invention, nucleotides can be arranged so as to obtain a suitable codon for expression in die host so that the producing ratio of the polypeptide of interest can be improved. Furthermore, the transcription termination sequence is not essential to express a gene in the above recombinant vector, it is preferred to arrange a transcription terminating sequence immediately downstream of the structural gene.

The host cell includes microorganisms belonging to the genera *Escherichia*, and examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α and the like.

Any introduction method of the recombinant vector can be used, so long as it is a method for introducing DNA into the above-described host cell, and examples include a method using a calcium ion described in *Proc. Natl. Acad. Sci. USA*, 69, 2110 (1972), methods described in *Gene*, 17, 107 (1982) and *Molecular & General Genetics*, 168, 111 (1979) and the like.

When an animal cell is used as the host cell, an expression vector includes, for example, pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDMS [*Nature*, 329, 840, (1987)], pcDNAI/Amp (manufactured by Invitrogen), pREP4 (manufactured by Invitrogen), pAGE103 [*J. Biochemistry*, 101, 1307 (1987)], pAGE210, pME18SFL3, pKANTEX93 (WO 97/10354) and the like.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter and the like. Also, the enhancer of the IE gene of human CMV can be used together with the promoter.

The host cell includes human Namalwa cell, monkey COS cell, Chinese hamster ovary (CHO) cell, HST5637 (Japanese Published Unexamined Patent Application No. 299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

As the expression method of the gene, in addition to direct expression, secretory production, fusion protein expression and the like in accordance with the method described in *Molecular Cloning, A Laboratory Manual*, Second Edition, Cold Spring Harbor Laboratory Press (1989) can be carried out. When expression is carried out in a cell derived from eukaryote, a polypeptide to which a sugar or a sugar chain is added can be obtained.

The polypeptide used in the present invention can be produced by culturing the thus obtained transformant in a medium to form and accumulate the polypeptide in the culture, and recovering it from the culture. The method for culturing the transformant in the medium is carried out according to the usual method used in culturing of hosts.

When a microorganism transformed with a recombinant vector containing an inducible promoter as a promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using tip promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for the Biological Medicine*, 73, 1 (1950)], the media to which fetal calf serum, etc. is added, and the like. The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Thus, the polypeptide used in the present invention can be produced by culturing a transformant derived from a microorganism, an animal cell or the like which comprises a recombinant vector into which a DNA encoding the polypeptide used in the present invention is inserted, in accordance with a general culturing method, to thereby form and accumulate the polypeptide, and then recovering the polypeptide from the culture.

Regarding the expression method of gene, in addition to direct expression, secretory production, fusion protein expression and the like can be carried out according to the method described in *Molecular Cloning, A Laboratory Manual*, Second Edition, Cold Spring Harbor Laboratory Press (1989).

The process for producing the polypeptide includes a method of intracellular expression in a host cell, a method of extracellular secretion from a host cell, a method of producing on a host cell membrane outer envelope, and the like. The appropriate method can be selected by changing the host cell used and the structure of the polypeptide produced.

When the polypeptide is produced in a host cell or on a host cell membrane outer envelope, the gene product can be positively secreted extracellularly in accordance with the method of Paulson et al. [*J. Biol. Chem.*, 264, 17619 (1989)], the method of Lowe et al. [*Proc. Natl. Acad. Sci, USA*, 86, 8227 (1989), *Genes Develop.*, 4, 1288 (1990)], the methods described in Japanese Published Unexamined Patent Application No. 336963/93 and WO 94/23021, and the like.

Also, the production amount can be increased in accordance with the method described in Japanese Published Unexamined Patent Application No. 227075/90 utilizing a gene amplification system using a dihydrofolate reductase gene.

The polypeptide can be isolated and purified from the above culture, for example, as follows.

When the polypeptide is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When the polypeptide is expressed intracellularly by forming an inclusion body, the cells are recovered, disrupted and centrifuged in the same manner, and the inclusion body of the polypeptide are recovered as a precipitation fraction. The recovered inclusion body of the protein is solubilized with a protein denaturing agent. The protein is made into a normal three-dimensional structure by diluting or dialyzing the solubilized solution, and then a purified product of the polypeptide is obtained by the same isolation purification method as above.

When the polypeptide or the derivative such as a glycosylated product is secreted extracellularly, the polypeptide or the derivative such as a glycosylated product can be recovered from the culture supernatant. That is, the culture is treated by a method such as centrifugation in the same manner as above to obtain a culture supernatant from which solids are removed, a purified product of the polypeptide can be obtained from the culture supernatant by the same isolation purification method as above.

Also, the polypeptide used in die present invention can be produced by a chemical synthesis method, such as Fmoc (fluorenylmethyloxycarbonyl) method or tBoc (t-butyloxycarbonyl) method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(2) Immunization of Animal and Preparation of Antibody-Producing Cell

A mouse, rat or hamster 3 to 20 weeks old is immunized with the antigen prepared above, and antibody-producing cells are collected from the spleen, lymph node or peripheral blood of the animal. Also, when the increase of a sufficient titer in the above animal is recognized due to low immunogenecity, a CLDN4 knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual* (Cold Spring Harbor Laboratory (1988)] or the like. A mouse, rat or hamster showing a sufficient antibody titer in their sera against the antigen used for the immunization is used as the supply source of antibody-producing cells.

In fusion of the antibody-producing cells and myeloma cells, on the 3rd to 7th days after final administration of the antigen, tissue containing the antibody-producing cells such as the spleen from the immunized mouse, rat or hamster is excised to collect the antibody-producing cell. When the spleen cells are used, the spleen is cut out in an MEM medium Nissui Pharmaceutical) and loosened by tweezers and centrifuged (at 1200 rpm, for 5 minutes). Then, the supernatant is discarded and a Tris-ammonium chloride buffer (pH. 7.65) is applied for 1 to 2 minutes to remove erythrocytes. After washing 3 times with the MEM medium, antibody-producing cells for fusion is provided.

(3) Preparation of Myeloma Cell

An established cell line obtained from mouse is used as myeloma cells, Examples include 8-azaguanine-resistant mouse (derived from BALB/c mouse) myeloma cell line P3-X63Ag8-U1 (P3-U1) [*Current Topics in Microbiology and Immunology*, 18, 1-7 (1978)], P3-NS1/1-Ag41 (NS-1) [*European J. Immunology*, 6, 511-519 (1976)], SP2/0-Ag14 (SP-2) [*Nature*, 276, 269-270 (1978)], P3-X63-Ag8653 (653) [*J. Immunology*, 123, 1548-1550 (1979)], P3-X63-Ag8 (X63) [*Nature*, 256, 495-497 (1975)] and the like. These cell lines are subcultured in an 8-azaguanine medium [a medium in which glutamine (1.5 mM), 2-mercaptoethanol ($5\times10^{-5}$ M), gentamicin (10 µg/ml) and fetal calf serum (FCS) are added to RPMI-1640 medium (hereinafter referred to as "normal medium") and 8-azaguanine (15 µg/ml) is further added] and they are subcultured in the normal medium 3 or 4 days before cell fusion to ensure the cell number of $2\times10^7$ or more on the day for fusion.

(4) Cell Fusion

The above-described antibody-producing cells and myeloma cells were sufficiently washed with an MEM medium or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells: the myeloma cells=5 to 10:1, followed by centrifugation (1200 rpm, 5 minutes). Then, the supernatant is discarded, and precipitated cell group is sufficiently loosen. To $10^8$ of the antibody-producing cells, 0.2 to 1 mL of a mixture solution of 2 g of polyethylene glycol-1000 (PEG-1000), 2 mL of MEM and 0.7 mL of dimethylsulfoxide is added under stirring at 37° C., and 1 to 2 mL of MEM medium is added several times every one or two minutes, and MEM medium is added to give a total amount of 50 mL. After centrifugation (900 rpm, 5 minutes), the supernatant is discarded, the cells are gently loosen, and the cells are gently suspended in 100 mL of HAT medium [a medium in which hypoxanthine ($10^{-4}$ mol/l), thymidine ($1.5\times10^{-5}$ mol/l) and aminopterin ($4\times10^{-7}$ mol/l) is added to the normal medium] by suction and sucking out using a measuring pipette. The suspension is dispensed at 100 µl/well onto a 96-well culturing plate and cultured in a 5% $CO_2$ incubator at 37° C. for 7 to 14 days.

After the culturing, a portion of the culture supernatant is sampled and a hybridoma which is reactive to an antigen containing the polypeptide used in the present invention and is not reactive to an antigen which does not contain the polypeptide is selected by binding assay as described below.

Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Monoclonal Antibody

The hybridoma cells producing an anti-CLDN4 monoclonal antibody obtained in (4) are administered by intraperitoneal injection into 8- to 10-week-old mice or nude mice treated with pristane (0.5 ml of 2,6,10,14-tetramethylpentadecane (pristane) is intraperitoneally administered, followed by feeding for 2 weeks) at a dose of $2 \times 10^6$ to $5 \times 10^7$ cells/animal. The hybridoma develops ascites tumor in 10 to 21 days. The ascitic fluid is collected from the mice, centrifuged (at 3,000 rpm, for 5 minutes) to remove solids, subjected to salting out with 40 to 50% saturated ammonium sulfate and then precipitated by caprylic acid, passed through a DEAE-Sepharose column, a protein A column or a gel filtration column to collect an IgG or IgM fraction as a purified monoclonal antibody.

The subclass of the antibody can be determined using a subclass typing kit by enzyme immunoassay. The amount of the protein can be determined by the Lowry method or from the absorbance at 280 nm.

(6) Binding Assay

As the antigen, a gene-introduced cell or a recombinant protein obtained by introducing an expression vector containing a cDNA encoding CLDN4 polypeptide used in the present invention into *Escherichia coli*, yeast, an insect cells an animal cell or the like, or a purified polypeptide or partial peptide obtained from a human tissue is used. When the antigen is a partial peptide, a conjugate is prepared with USA (bovine serum albumin), KLH (keyhole limpet hemocyanin) or the like and is used.

After making these antigens into a solid layer by dispensing in a 96-well plate, a serum of an animal to be immunized, a culture supernatant of a monoclonal antibody-producing hybridoma or a purified antibody is dispensed therein as the primary antibody and allowed to react. After thoroughly washing with PBS or PBS-0.05% Tween, an anti-immunoglobulin antibody labeled with biotin, an enzyme, a chemiluminescent material, a radiation compound or the like is dispensed therein as the secondary antibody and allowed to react. After thoroughly washing with PES-Tween, the reaction is carried out in response to the label of the secondary antibody.

The antibody which competes with the thus obtained monoclonal antibody for its binding to the extracellular region of CLDN4 can be prepared by adding an antibody to be tested to the above-mentioned binding assay system and carrying out reaction. That is, a monoclonal antibody which competes with the thus obtained monoclonal antibody for its binding to the extracellular region of CLDN4 can be prepared by carrying out a screening of an antibody by which the binding of the monoclonal antibody is inhibited when the antibody to be tested is added.

(7) Inhibition Assay for Activity of CLDN4

A gene-introduced cell obtained by introducing an expression vector containing a cDNA encoding CLDN4 polypeptide used in the present invention into an animal cell or the like by the method described in (1), or a normal cell or cancer cell expressing CLDN4, is used as the evaluation cell.

Examples the method for evaluating the activity of the antibody or antibody fragment of the present invention to inhibit formation of TJ which is activity of CLDN4 include a method in which the antibody or antibody fragment of the present invention is allowed to react with a normal cell or cancer cell expressing CLDN4, and inhibition of the formation of TJ formed between cells is observed using an electron microscope or the like, a method in which suppression of CLDN4 expression in the intercellular adhesion region is evaluated by immunostaining, Western blotting or the like [*J. Cell. Biol.*, 147, 195 (1999)], and the like.

Examples of the method for evaluating the activity of the antibody or antibody fragment of the present invention to inhibit epithelial barrier activity which is activity of CLDN4 include a method in which the antibody or antibody fragment is allowed to react with a normal cell or cancer cell expressing CLDN4, and reduction of transepithelial electric resistance is measured, a method in which acceleration of permeability of a substance via intercellular space is measured using an appropriate tracer (e.g., FITC-Dextran, etc.) [*J. Cell. Biol.*, 147, 195 (1999)], and the like.

Examples of the assay method for evaluating the activity of the antibody or antibody fragment of the present invention to inhibit the activity, such as tumor forming ability, infiltration ability or metastasis causing ability, in cancer cells, which is activity of CLDN4, include a method in which the antibody or antibody fragment is allowed to react with these cells, and the activity is measured using a wound healing method [*Methods. Mol. Biol.*, 26, 177 (1999)], a soft agar colony formation method [*Proc. Natl. Acad. Sci. USA*, 72, 4435 (1975)], an invasion assay, migration assay or the like trans-well method [J. Exp. Med., 115, 453 (1962)] and the like.

According to the above methods, the neutralizing activity for CLDN4 of the antibody or antibody fragment of the present invention can be evaluated.

(8) Preparation of Monoclonal Antibody with Reacts with Both of CLDN3 and CLDN4

A monoclonal antibody which specifically recognizes three-dimensional structure of an extracellular region of CLDN4 and binds to an extracellular region of CLDN4, wherein the monoclonal antibody specifically recognizes three-dimensional structure of an extracellular region of CLDN3 and binds to the extracellular region of CLDN3, and a monoclonal antibody which specifically binds to an extracellular region of CLDN4 and has neutralizing activity for CLDN4, wherein the monoclonal antibody specifically recognizes three-dimensional structure of an extracellular region of CLDN3 and binds to the extracellular region of CLDN3 can be prepared in the same manner as in 1-(6) described above by selecting monoclonal antibodies which react with a cell expressing CLDN4, a CLDN4 recombinant protein, a purified CLDN4 polypeptide or CLDN4 partial peptide prepared from a human tissue or the like, and, from the monoclonal antibodies, selecting a monoclonal antibody which reacts with a CLDN3-expressing cell, a CLDN3 recombinant protein, a purified CLDN3 polypeptide or CLDN3 partial peptide prepared from a human tissue or the like.

2. Preparation of Recombinant Antibody

As production examples of recombinant antibodies, processes for producing a human chimeric antibody and a humanized antibody are shown below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to K class, and the like. As the DNAs encoding CH and CL of a human antibody, a chromosomal DNA comprising an exon and an intron or cDNA can be used. As the expression vector for animal cell, any expression vector can be used, so long as a gene encoding the C region of a human antibody can be inserted thereinto and expressed therein, Examples include pAGE107 [*Cytotechnol.*, 3, 133 (1990)], pAGE103 [*J. Biochem.*, 101, 1307 (1987)], pHSG274 [*Gene*, 27, 223 (1984)], pKCR [*Proc. Natl, Acad. Sci. USA*, 78, 1527 (1981)], pSG1bd2-4 [*Cytotechnol.*, 4, 173 (1990)], pSE1UK1Sed1-3 [*Cytotechnol.*, 13, 79 (1993)] and the like. Examples of a promoter and enhancer used for an expression vector for animal cell include an SV40 early promoter [*J. Biochem.*, 101, 1307 (1987)], a Moloney mouse leukemia virus LTR [*Biochem, Biophys. Res. Commun.*, 149, 960 (1987)], an immunoglobulin H chain promoter [*Cell, it*, 479 (1985)] and enhancer [*Cell*, 33, 717 (1983)] and the like.

The vector for expression of recombinant antibody may be either of a type in which a gene encoding an antibody H chain and a gene encoding an antibody L chain exist on separate vectors or of a type in which both genes exist on the same vector (tandem type). In respect of easiness of construction of a vector for expression of recombinant antibody, easiness of introduction into animal cells, and balance between the expression amounts of antibody H and L chains in animal cells, a tandem type of the vector for expression of recombinant antibody is more preferred [*J. Immunol. Methods*, 167, 271 (1994)]. Examples of the tandem type of the vector for expression of recombinant antibody include pKANTEX93 (WO 97/10354), pEE18 [*Hybridoma*, 17, 559 (1998)], and the like.

(2) Obtaining of cDNA Encoding V Region of Antibody Derived from Non-Human Animal and Analysis of Amino Acid Sequence cDNAs encoding VH and VL of an antibody derived from a non-human animal are obtained as follows.

mRNA is extracted from hybridoma cells producing an antibody derived from a non-human animal to synthesize cDNA. The synthesized cDNA is cloned into a vector such as a phage or a plasmid, to prepare a cDNA library. Each of a recombinant phage or recombinant plasmid containing cDNA encoding VH or VL is isolated from the library using DNA encoding a part of the C region or V region of an antibody derived from a non-human animal as the probe. The full length of the nucleotide sequences of VH and VL of the antibody derived from a non human animal of interest on the recombinant phage or recombinant plasmid are determined, and the full length of the amino acid sequences of VH and VL are deduced from the nucleotide sequences.

The non-human animal may be any animal such as mouse, rat, hamster or rabbit, so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)] and the like. Examples of the method for preparing mRNA from total RNA include an oligo (dT) immobilized cellulose column method [*Molecular Cloning, A Laboratory Manual*, Second Edition, Cold Spring Harbor Laboratory Press (1989)] and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods [*Molecular Cloning, A Laboratory Manual*, Cold Spring Harbor Lab. Press (1989); *Current Protocols in Molecular Biology*, Supplement 1-34]; a method using a commercially available kit such as Super Script™ Plasmid System for cDNA Synthesis and Plasmid Cloning (manufactured by GIBCO BRL), ZAP-cDNA Kit (manufactured by Stratagene), etc.; and the like.

The vector into which the synthesized cDNA using miRNA extracted from a hybridoma cell as the template is inserted for preparing a cDNA library may be any vector, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning: A Practical Approach*, I, 49 (1985)], Lambda BlueMid (manufactured by Clontech), λExCell and pT7T3 18U (manufactured by Pharmacia), pcD2 [*Mol Cell, Biol.*, 3, 280 (1983)], pUC18 [*Gene*, 33, 103 (1985)], and the like.

Any *Escherichia coli* for introducing the cDNA library constructed by a phage or plasmid vector may be used, so long as the cDNA library call be introduced, expressed and maintained, Examples include XL1-Blue MRF' [*Strategies*, 5, 81 (1992)], C600 [*Genetics*, 39, 440 (1954)], Y1088 and Y1090 [*Science*, 222: 778 (1983)], NM522 [*J. Mol. Biol.*, 166, 1 (1983)], K802 [*J. Mol. Biol.*, 16, 118 (1966)], JM105 [*Gene*, 38, 275 (1985)], and the like.

A colony hybridization or plaque hybridization method using an isotope- or fluorescence-labeled probe may be used for selecting cDNA clones encoding VH and VL of an antibody derived from a non-human animal from the cDNA library [*Molecular Cloning, A Laboratory Manual*, Second Edition, Cold Spring Harbor Laboratory Press (1989)]. Also, the cDNAs encoding VH and VL can be prepared through polymerase chain reaction (hereinafter referred to as "PCR"; *Molecular Cloning, A Laboratory Manual*, Second Edition, Cold Spring Harbor Laboratory Press (1989); *Current Protocols in Molecular Biology*, Supplement 1-34) by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(−) (manufactured by Stratagene), carrying out the reaction by a usually used nucleotide analyzing method such as the dideoxy method of Sanger, F. et al. [*Proc. Natl. Acad. Sci. USA*, 74, 5463 (1977)], and then analyzing the sequence using an automatic nucleotide sequence analyzer such as A.L.F. DNA sequencer (manufactured by Pharmacia).

Whether the obtained cDNAs encode the full amino acid sequences of VL and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies

[*Sequences of Proteins of Immunological Interest*, US Dept. Health and Human Services (1991)], and the subgroup to which they belong can also be known. Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

Moreover, the novelty of the sequence can be examined by carrying out a homology search with sequences in any database, for example, SWISS-PROT, PIR-Protein or the like using the full length of the amino acid sequences of VH and VL, for example, according to the BLAST method [*J. Mol. Biol.*, 215, 403 (1990)] or the like.

(3) Construction of Vector for Expression of Human Chimeric Antibody cDNAs encoding VH and VL of antibody of non-human animal are cloned in the upstream of genes encoding CH or CL of human antibody of vector for expression of recombinant antibody mentioned in the above 2(1) to thereby construct a vector for expression of human chimeric antibody. For example, each cDNA encoding VH and VL of antibody of non-human animal is ligated to synthetic DNA comprising a nucleotide sequence of 3'-terminal of VH or VL of antibody of non-human animal and a nucleotide sequence of 5'-terminal of CH or CL of human antibody and having recognition sequence of an appropriate restriction enzyme at both ends, and cloned so that each of them is expressed in an appropriate form in the upstream of gene encoding CH or CL of human antibody of the vector for expression of humanized antibody mentioned in the above 2(1) to construct a vector for expression of human chimeric antibody. In addition, cDNA encoding VH or VL or nonhuman animal is amplified by PCR using a synthetic DNA having a recognition sequence of an appropriate restriction enzyme at both terminals and each of them is cloned to the vector for expression of recombinant antibody mentioned in the above 2(1).

(4) Construction of cDNA Encoding V Region of Humanized Antibody cDNAs encoding VH or VL of a humanized antibody can be obtained as follows. First, amino acid sequences of framework region (hereinafter referred to as "FR") in VH or VL of a human antibody to which amino acid sequences of CDRs in VH or VL of an antibody derived from a non-human animal antibody are transplanted are selected. Any amino acid sequences of FR in VH or VL of a human antibody can be used, so long as they are from human. Examples include amino acid sequences of FRs in VH or VL of human antibodies registered in database such as Protein Data Bank or the like, and amino acid sequences common to subgroups of FRs in VH or VL of human antibodies [*Sequences of Proteins of Immunological Interest*, US Dept. Health and Human Services (1991)], and the like. In order to inhibit the binding activity of the antibody, amino acid sequences having high homology (at least 60% or more) with die amino acid sequence of FR in VH or VL of the original antibody is selected. Then, amino acid sequences of CDRs of VH or VL of the original antibody are grafted to the selected amino acid sequence of FR in VH or VL of the human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed. Based on the designed nucleotide sequences, several synthetic DNAs having a length of about 100 nucleotides are synthesized, and PCR is carried out using them. In this case, it is preferred in each of the H chain and die L chain that 6 synthetic DNAs are designed in view of the reaction efficiency of PCR and the lengths of DNAs which can be synthesized.

Furthermore, the cDNA encoding VH or VL of a humanized antibody can be easily cloned into the vector for expression of humanized antibody constructed in the (1) of this item 2 by introducing the recognition sequence of an appropriate restriction enzyme to the 5' terminal of the synthetic DNAs existing on the both ends. After the PCR, an amplified product is cloned into a plasmid such as pBluescript SK (−) (manufactured by Stratagene) or the like, and die nucleotide sequence is determined according to the method described in (2) of this item 2 to obtain a plasmid having a DNA sequence encoding the amino acid sequence of VH or VL of a desired humanized antibody.

(5) Modification of Amino Acid Sequence of V Region of Humanized Antibody

It is known that when a humanized antibody is produced by simply grafting only CDRs in VH and VL of an antibody derived from a non-human animal into FRs of VH and VL of a human antibody, its antigen binding activity is lower than that of the original antibody derived from a non-human animal [*BIO/TECHNOLOGY*, 9, 266 (1991)]. As the reason, it is considered that several amino acid residues in not only CDRs but also FRs directly or indirectly relate to antigen binding activity in VH and VL of the original antibody derived from a non-human animal, and as a result of grafting of CDRs, such amino acid residues are changed to different amino acid residues of FRs in VH and VL of a human antibody. In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original antibody derived from a non-human animal to thereby increase the antigen binding activity which has been decreased [*BIO/TECHNOLOGY*, 9, 266 (1991)]. In the production of a humanized antibody, how to efficiently identify the amino acid residues relating to the antigen binding activity in FR is most important, so that the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. Although the information of the three-dimensional structure of antibodies has been useful in the production of a humanized antibody, no method for producing a humanized antibody which can be applied to any antibodies has been established yet. Therefore, various attempts must be currently be necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in (4) of this item 2, With regard to the amplified product obtained by the PCR, the nucleotide sequence is determined according to the method as described in (2) of this item 2 so that whether die objective modification has been carried out is confirmed.

(6) Construction of Vector for Expression of Humanized Antibody

A vector for expression of humanized antibody can be constructed by cloning each cDNA encoding VH or VL of a constructed recombinant antibody into upstream of each gene encoding CH or CL of the human antibody in the vector for expression of humanized antibody as described in (1) of this item 2.

For example, when recognizing sequences of an appropriate restriction enzymes are introduced to the 5'-terminal of synthetic DNAs positioned at both ends among synthetic DNAs used in the construction of VH or VL of the humanized antibody in (4) and (5) of this item 2, cloning can be carried out so that they are expressed in an appropriate form in the upstream of each gene encoding CH or CL of the human antibody in the vector for expression of humanized antibody as described in (1) of this item 2, (7) Transient Expression of Recombinant Antibody In order to efficiently evaluate the antigen binding activity of various humanized antibodies produced, the recombinant antibodies can be expressed transiently using the vector for expression of humanized antibody as described in (3) and (6) of this item 2 or the modified expression vector thereof. Any cell can be used as a host cell, so long as the host cell can express a recombinant antibody. Generally, COS-7 cell (ATCC CRL1651) is used in view of its high expression amount [*Methods in Nucleic Acids Res.*, CRC Press, 283 (1991)]. Examples of the method for introducing the expression vector into COS-7 cell include a DEAE-dextran method [*Methods in Nucleic Acids Res.*, CRC Press, 283 (1991)], a lipofection method [*Proc. Natl. Acad. Sci. USA*, 84, 7413 (1987)], and the like.

After introduction of the expression vector, the expression amount and antigen binding activity of the recombinant antibody in the culture supernatant can be determined by the enzyme immunoassay [hereinafter referred to as "ELISA"; *Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

(8) Stable Expression of Recombinant Antibody

A transformant which stably expresses a recombinant antibody can be obtained by introducing the vector for expression of recombinant antibody described in (3) and (6) of this item 2 into an appropriate host cell.

Examples of the method for introducing the expression vector into a host cell include electroporation [Japanese Published Unexamined Patent Application No. 257891/90, *Cytotechnology*, 3, 133 (1990)] and the like.

As the animal cell into which a vector for expression of recombinant is introduced, any cell can be used, so long as it is an animal cell which can produce the recombinant antibody. Examples include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR") is defective [*Proc. Natl. Acad. Sci. U.S.A.,* 77, 4216 (1980)], lection resistance-acquired Lec13 [*Somatic Cell and Molecular genetics,* 12, 55 (1986)], CHO cell in which α1,6-fucosyltransaferse gene is defected (WO 05/35586), rat YB2/3HL.P2.G11.16Ag.20 cell (ATCC CRL1662), and the like.

In addition to the above host cells, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetyl-glucosamine in the reducing end through α-bond in a complex type N-glycoside-linked sugar chain, or a protein relating to transport of an intracellular sugar nucleotide, GDP-fucose, to the Golgi body are introduced is decreased or deleted, preferably CHO cell in which α1,6-fucosyltransferase gene is defected as described in WO 05/35586, WO 02/31140 or the like, can also be used.

After introduction of the expression vector, transformants which express a recombinant antibody stably are selected in accordance with die method disclosed in Japanese Published Unexamined Patent Application No. 257891/90, by culturing in a medium for animal cell culture containing an agent such as G418 sulfate (hereinafter referred to as "G418", manufactured by Sigma) or the like. Examples of the medium for animal cell culture include RPMI1640 medium (manufactured by Invitrogen), GIT medium (manufactured by Nissui Pharmaceutical), EX-CELL301 medium (manufactured by JRH), IMDM medium (manufactured by Invitrogen), Hybridoma-SFM medium (manufactured by Invitrogen), media obtained by adding various additives such as fetal calf serum (hereinafter referred to as "FCS") to these media, and the like. The recombinant antibody can be produced and accumulated in a culture supernatant by culturing the selected transformants in a medium. The expression amount and antigen binding activity of the recombinant antibody in the culture supernatant can be measured by ELISA or the like. Also, in the transformant, the expression amount of the recombinant antibody can be increased by using dhfr amplification system or the like according to the method disclosed in Japanese Published Unexamined Patent Application No. 257891/90.

The recombinant antibody can be purified from the culture supernatant of the transformant by using a protein A column [*Monoclonal Antibodies—Principles and practice*, Third edition, Academic Press (1996), *Antibodies—A Laboratory Manual*, Cold Spring Harbor Laboratory (1988)]. Any other conventional methods for protein purification can be used. For example, the recombinant antibody can be purified by a combination of gel filtration, ion-exchange chromatography, ultrafiltration and the like. The molecular weight of the H chain or the L chain of the purified recombinant antibody or the antibody molecule as a whole is determined by polyacrylamide gel electrophoresis (hereinafter referred to as "SDS-PAGE") [*Nature,* 227, 680 (1970)] ,Western blotting [*Monoclonal Antibodies—Principles and practice*, Third edition, Academic Press (1996), *Antibodies—A Laboratory Manual*, Cold Spring Harbor Laboratory (1988)] , and the like.

3. Activity Evaluation of the Antibody or Antibody Fragment of the Present Invention Reaction specificity of the purified antibody or antibody fragment of the present invention can be evaluated in the following manner.

CLDN3 gene (SEQ ID NO:25), CLDN4 gene (SEQ ID NO:1), CLDN5 gene (SEQ ID NO:29), CLDN6 gene (SEQ ID NO:5) and CLDN9 gene (SEQ ID NO:33) are cloned and CLDN-expressing cells which express respective genes are prepared. Next, reactivity of the cell which expresses CLDN3 (SEQ ID NO:26), CLDN4 (SEQ ID NO:2), CLDN5 (SEQ ID NO:30), CLDN6 (SEQ ID NO:6) or CLDN9 (SEQ ID NO:34) with the purified antibody is measured by ELISA, fluorescent antibody technique [*Cancer Immunol, Immunother.,* 36, 373 (1993)] or the like. Also, each of CLDN3 (SEQ ID NO:26), CLDN4 (SEQ ID NO:2), CLDN5 (SEQ ID NO:30), CLDN6 (SEQ ID NO:6) and CLDN9 (SEQ ID NO:34) proteins having three-dimensional structure may be prepared by extracting membrane fractions or membrane proteins of the CLDN-expressing cells under appropriate conditions, and the reactivity of the extracted CLDN protein with the purified antibody can be measured by the surface plasmon resonance (SPR)-aided BIAcore™, ELISA or the like method. The cytotoxic activities upon the antigen-expressing ell lines can be evaluated by measuring CDC activity, ADCC activity or the like according to a known method [*Cancer Immunol. Immunother.* 36, 373 (1993)].

In addition, die inhibitory activity for the activity of CLDN4 in the purified antibody or antibody fragment of the present invention can be evaluated by the method described in the above-described 1-(7) using a cell expressing CLDN4.

4. Method for Diagnosing Disease Using the Anti-CLDN4 Monoclonal Antibody or Antibody Fragment of the Present Invention A disease relating to CLDN4 can be diagnosed by detecting or determining CLDN4 or a cell expressing the polypeptide using the antibody or antibody fragment of the present invention.

The disease relating to CLDN4 is not limited, so long as it is a disease relating to a cell expressing the polypeptide, and includes, for example, cancer. The cancer includes cancer derived from epidermis, such as breast cancer, uterine cancer, colorectal cancer, stomach cancer, ovarian cancer, lung cancer, renal cancer, rectal cancer, thyroid cancer, uterine cervix cancer, small intestinal cancer, prostate cancer and pancreatic cancer.

The living body sample to be used for the detection or measurement of CLDN4 in the present invention is not particularly limited, so long as it has a possibility of containing the polypeptide, such as tissue cells, blood, blood plasma, serum, pancreatic juice, urine, fecal matter, tissue fluid or culture medium.

Among diseases relating to CLDN4, for example, diagnosis of a cancer can be carried out in the following manner.

On the living body samples collected from two or more of the living bodies of healthy parsons, the expressed amount of the polypeptide in the living body samples of healthy parsons is confirmed by carrying out detection or measurement of CLDN4 by the following immunological means using the antibody or antibody fragment of the present invention or derivatives thereof. By examining the expressed amount of the polypeptide also in the living body samples of the parson to be tested in the same manner, the expressed amount is compared with the expressed amount in healthy parsons, when the expressed amount of the polypeptide in the person to be tested is increased in comparison with the healthy persons, it can be diagnosed that cancer is positive.

The diagnostic agent containing the antibody or antibody fragment of the present invention or derivatives thereof may further contain a reagent for carrying out an antigen-antibody reaction or a reagent for detection of the reaction depending on the desired diagnostic method. The reagent for carrying out the antigen-antibody reaction includes a buffer, a salt, and the like. The reagent for detection includes a reagent used for common immunological detection or immunoassay such as antibody or antibody fragment thereof derivatives thereof, labeled secondary antibody for recognizing die antibody, antibody fragment or derivatives thereof and substrate corresponding to the labeling.

As a method for detection or determination of the amount of CLDN4 in the present invention, any known method may be included. For example, an immunological detection method or immunoassay may be exemplified.

An immunological detection or immunoassay is a method in which an antibody amount or an antigen amount is detected or determined using a labeled antigen or antibody. Examples of the immunological detection or immunoassay are radioactive substance-labeled immunoantibody method (RIA), enzyme immunoassay (EIA or ELISA), fluorescent immunoassay (FIA), luminescent immunoassay, Western blotting method, physico-chemical means (TIA, LAPIA and PCIA) and the like.

Examples of the radioactive substance-labeled immunoantibody method (RIA) include a method, in which the antibody or antibody fragment of the present invention is allowed to react with an antigen or a cell expressing an antigen, then anti-immunoglobulin antibody subjected to radioactive labeling or a binding fragment thereof is allowed to react therewith, followed by determination using a scintillation counter or the like.

Examples of the enzyme immunoassay (EIA or ELISA) include a method, in which the antibody or antibody fragment of the present invention is allowed to react with an antigen or a cell expressing an antigen, then an anti-immunoglobulin antibody or an binding fragment thereof subjected to antibody labeling is allowed to react therewith and the colored pigment is measured by a spectrophotometer, and, for example, sandwich ELISA may be used. As a label used in the enzyme immunoassay, any known enzyme label (*Enzyme Immunoassay* edited by Eiji Ishikawa, et al., published by Igaku Shoin) can be used as described already. Examples include alkaline phosphatase labeling, peroxidase labeling, luciferase labeling, biotin labeling and the like.

Sandwich ELISA is a method in which an antibody is bound to a solid phase, antigen to be detected or measured is trapped and another antibody is allowed to react with the trapped antigen. In the ELISA, 2 kinds of antibody which recognizes the antigen to be detected or measured or the antibody fragment thereof in which antigen recognizing site is different are prepared and one antibody or antibody fragments is previously adsorbed on a plate (such as a 96-well plate) and another antibody or antibody fragment is labeled with a fluorescent substance such as FITC, an enzyme such as peroxidase, or biotin. The plate to which the above antibody is adsorbed is allowed to react with the cell separated from living body or disrupted cell suspension thereof tissue or disintegrated solution thereof, cultured cells, serum, pleural effusion, ascites, eye solution or the like, then allowed to react with labeled monoclonal antibody or antibody fragment and a detection reaction corresponding to the labeled substance is carried out. When an antigen concentration in the sample to be tested is measured by the method, antigen concentration in the sample to be tested can be calculated from a calibration curve prepared by a stepwise dilution of antigen of known concentration. As antibody used for sandwich ELISA, any of polyclonal antibody and monoclonal antibody may be used or antibody fragments such as Fab, Fab' and $F(ab)_2$ may be used. As a combination of 2 kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay (FIA) includes a method described in the literatures [*Monoclonal Antibodies—Principles and practice*, Third Edition, Academic Press (1996); *Manual for Monoclonal Antibody Experiments*, Kodansha Scientific (1987)] and the like. As a label for the fluorescent immunoassay, any of known fluorescent labels (*Fluorescent Immunoassay*, by Aldra Kawao, Soft Science) may be used as described already. Examples include FITC labeling, RITC labeling and the like.

The luminescent immunoassay can be carried out using the methods described in *Monoclonal Antibodies—Principles and practice*, Third Edition, Academic Press (1996); *Manual for Monoclonal Antibody Experiments*, Kodansha Scientific (1987) and the like. As a label used for luminescent immunoassay, any of known luminescent labels [*Bioluminescence and Chemical Luminescence*, Hirokawa Shoten; *Rinsho Kensa*, 42 (1998)] can be included as described above. Examples include acridinium ester labeling, lophine labeling or the like may be used.

Western blotting is a method in which an antigen or a cell expressing an antigen is fractionated by SDS-polyacrylamide gel electrophoresis [*Antibodies—A Laboratory Manual* (Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example of Western blotting is described below.

Cells or tissues in which a polypeptide having the amino acid sequence represented by SEQ ID NO:2 is expressed are dissolved in a solution and, under reducing conditions, 0.1 to 30 μg as a protein amount per lane is electrophoresed by an SDS-PAGE method. The electrophoresed protein is transferred to a PVDF membrane and allowed to react with PBS containing 1% of BSA (hereinafter referred to as "BSA-PBS") at room temperature for 30 minutes for blocking. Here, the monoclonal antibody of the present invention is allowed to react therewith, washed with PBS containing 0.05% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL™ Western Blotting Detection Reagents (manufactured by Amersham) or the like to thereby detect a polypeptide having the amino acid sequence represented by SEQ ID NO:2. As an antibody used for the detection in Western blotting, an antibody which can be bound to a polypeptide having no three-dimensional structure of a natural type is used.

The physicochemical method is specifically carried out using the antibody or antibody fragment of the present invention by reacting CLDN4 as the antigen with the antibody or antibody fragment of the present invention to form an aggregate, and detecting this aggregate. Other examples of the physicochemical methods include a capillary method, a one-dimensional immunodiffusion method, an immunoturbidimetry and a latex immunoturbidimetry [*Handbook of Clinical Test Methods*, Kanehara Shuppan, 499 (1988)].

For example, in a latex immunodiffusion method, a carrier such as polystyrene latex having a particle size of about of 0.1 to 1 μm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is now possible to measure antigen concentration, etc. in the sample to be tested.

Since the antibody or antibody fragment of the present invention is capable of binding to an extracellular region of CLDN4, it is preferably used for detecting a cell expressing the polypeptide.

For the detection of the cell expressing the polypeptide, known immunological detection methods can be used, and an immunoprecipitation method, a fluorescent cell staining method, an immune tissue staining method and the like are preferably used. Also, an immunofluorescent staining method using FMAT 8100 HTS system (Applied Biosystem) and the like can be used.

An immunoprecipitation method is a method in which a cell expressing the polypeptide is allowed to react with the monoclonal antibody or antibody fragment of the present invention and then a carrier having specific binding ability to immunoglobulin such as protein G-Sepharose is added so that an antigen-antibody complex is precipitated. Also, the following method can be carried out.

The above-described antibody or antibody fragment of the present invention is solid-phased on a 96-well plate for ELISA and then blocked with BSA-PBS. When the antibody is in a non-purified state such as a culture supernatant of hybridoma cells anti-mouse immunoglobulin or rat immunoglobulin or protein A or G or the like is previously adsorbed on a 96-well plate for ELISA and blocked with BSA-PBS and a culture supernatant of hybridoma cell is dispensed thereto for binding. After USA-PBS is discarded and the residue is sufficiently washed with PBS, reaction is carried out with a dissolved solution of cells or tissues expressing polypeptide having the amino acid sequence represented by SEQ ID NO:2. An immune precipitate is extracted from the well-washed plate with a sample buffer for SDS-PAGE and detected by the above-described Western blotting.

An immune cell staining method and an immune tissue staining method are immunofluorescent staining methods (a flow cytometry) where cells or tissues in which antigen is expressed are treated, if necessary, with a surfactant or methanol to make an antibody easily permeate to the cells or tissues, then the antibody of the present invention is allowed to react therewith, then further allowed to react with an anti-immunoglobulin antibody or binding fragment thereof subjected to fluorescent labeling such as FITC, enzyme label such as peroxidase or biotin labeling and the label is visualized and observed under a microscope or cells are allowed to react with a fluorescence-labeled antibody and analyzed by a flow cytometer. That can be carried out by the methods described, for example, in the literatures [*Monoclonal Antibodies— Principles and practice*, Third Edition, Academic Press (1996), *Manual for Experiments of Monoclonal Antibodies*, Kodansha Scientific (1987)]. Particularly, since the antibody or antibody fragment of the present invention binds to three-dimensional structure of an extracellular region of CLDN4, it can be preferably used for detection of a cell expressing the polypeptide maintaining a natural type three-dimensional structure by a flow cytometry.

In addition, by using FMAT8100HTS system (manufactured by Applied Biosystems) which utilizes the principle of fluorescent antibody staining, the antigen quantity or antibody quantity can be measured without separating the formed antibody-antigen complex and the free antibody or antigen which is not concerned in the formation of the antibody-antigen complex.

5. Method for Diagnosing Disease Using the Monoclonal Antibody or Antibody Fragment of the Present Invention which Reacts with Both CLDN3 and CLDN4

A disease relating to CLDN4 and/or CLDN3 can be diagnosed by detecting or determining a cell expressing CLDN4 and/or CLDN3 by using the monoclonal antibody or antibody fragment of the present invention which specifically recognizes three-dimensional structure of an extracellular region of CLDN4 and binds to the extracellular region of CLDN4 and also specifically recognizes three-dimensional structure of an extracellular region of CLDN3 and binds to the extracellular region of CLDN3, or the monoclonal antibody or antibody fragment of the present invention which specifically binds to an extracellular region of CLDN4 and has neutralizing activity for CLDN4 and also specifically recognizes three-dimensional structure of an extracellular region of CLDN3 and binds to the extracellular region of CLDN3.

The disease relating to CLDN3 and/or CLDN4 is not limited, so long as it is a disease relating to a cell expressing the polypeptide, such as cancer. The cancer includes cancer derived from epidermis, such as breast cancer, uterine cancer, colorectal cancer, stomach cancer, ovarian cancer, uterine cervix cancer and prostate cancer.

The detection, measurement and diagnosis of CLDN4 and/or CLDN3 can be carried out in the same manner in the above-described item 4, 6. Method for Treating Disease Using the Anti-CLDN4 Monoclonal Antibody or Antibody Fragment of the Present Invention The monoclonal antibody or antibody fragment which specifically recognizes three-dimensional structure of an extracellular region of CLDN4 and binds to the extracellular region or the monoclonal antibody or the antibody fragment thereof which binds to an extracellular region of CLDN4 and has neutralizing activity for CLDN4 in the present invention can be used for the treatment of diseases relating to CLDN4.

The disease relating to the polypeptide encoded by CLDN4 gene is not limited, so long as it is a disease relating to a cell expressing the polypeptide, such as cancer. The cancer includes cancer derived from epidermis, such as breast cancer, uterine cancer, colorectal cancer, stomach cancer, ovarian cancer, lung cancer, renal cancer, rectal cancer, thyroid cancer, uterine cervix cancer, small intestinal cancer, prostate cancer and pancreatic cancer.

The therapeutic agent in the present invention includes a therapeutic agent for cancer comprising the antibody or antibody fragment of the present invention. The therapeutic agent in the present invention also includes a therapeutic agent for cancer having effector activity such as ADCC activity and CDC activity or a therapeutic agent for cancer by an apoptosis-inducing activity.

Since the antibody or antibody fragment of the present invention can recognizes three-dimensional structure of CLDN4 expressed on the cell membrane, it can recognize a cell expressing CLDN4 in vivo. Accordingly, among the antibodies or the antibody fragments of the present invention, the antibody or antibody fragment thereof effector activity can injure the cell expressing CLDN4 in vivo and in vitro. Also, since the antibody or antibody fragment of the present invention can injure and decrease cells expressing CLDN4 in viva, it is particularly effective as a therapeutic agent.

The therapeutic agent comprising the antibody or antibody fragment of the present invention or derivatives thereof may be only the antibody or antibody fragment or derivatives thereof as an active ingredient, and is preferably supplied as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred. The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like. Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like. Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like. Injections can be prepared using a carrier such as a salt solution, a glucose solution or a mixture of both thereof. Suppositories can be prepared using a carrier such as cacao butter, hydrogenated fat or carboxylic acid. Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. Depending on the properties of the antibody and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration method, treating period, age, body weight and the like, it is usually 10 µg/kg to 8 mg/kg per day and per adult, 7. Method for Treating Disease Using the Antibody or Antibody Fragment of the Present Invention which Reacts Both CLDN3 and CLDN4

The monoclonal antibody or antibody fragment of the present invention which specifically recognizes three-dimensional structure of an extracellular region of CLDN4, binds to the extracellular region of CLDN4, specifically recognizes three-dimensional structure of an extracellular region of CLDN3 and binds to the extracellular region of CLDN3 or the monoclonal antibody or antibody fragment of the present invention which binds to an extracellular region of CLDN4, has neutralizing activity for CLDN4, specifically recognizes three-dimensional structure of an extracellular region of CLDN3 and binds to the extracellular region of CLDN3 can be used for treatment of a disease relating to CLDN4 and/or CLDN3.

The disease relating to CLDN3 and/or CLDN4 is not limited, so long as it is a disease relating to a cell expressing the polypeptide, such as cancer. The cancer includes cancer derived from epidermis, such as breast cancer, uterine cancer, colorectal cancer, stomach cancer, ovarian cancer, uterine cervix cancer and prostate cancer.

The treatment using the antibody of the present invention can be carried out by the therapeutic agent prepared in the same manner as in the above 6 and the therapeutic method.

The present invention provides a monoclonal antibody or an antibody fragment thereof, which specifically recognizes three-dimensional structure of an extracellular region of CLDN4 and binds to the extracellular region; a monoclonal antibody or an antibody fragment thereof, which specifically recognizes three-dimensional structures of both of extracellular regions of CLDN3 and CLDN4 and binds to the extracellular regions; a hybridoma which produces the antibody; a DNA which encodes the antibody; a vector which comprises the DNA; a transformant obtained by transforming the vector; a process for producing an antibody or an antibody fragment thereof using the hybridoma or the transformant; and a diagnostic agent or a therapeutic agent for cancer using the antibody or the antibody fragment.

The present invention is described below by Examples; however, the present invention is not limited to the following Examples.

EXAMPLE 1

Construction of CLDN-myc/His Gene-Introduced CHO Cell Clone (1) CLDN4-myc/His Gene-Introduced CHO Cell Clone PCR was carried out by preparing 100 µl of a reaction solution containing 100 ng of a plasmid having the human CLDN4 gene (SEQ ID NO:1) registered with Japan DNA Data Bank (AK126315) as the template, 10 µl of 10×KOD buffer 1, 10 µl of 2 mmol/l dNTP, 4 µl of 25 mmol/l magnesium chloride, 1 µl of 1 µg/µl of each of the primers comprising the nucleotide sequences represented by SEQ ID NO:9 and SEQ ID NO:10 and 1 µl of KOD polymerase (manufactured by TOYOBO). Regarding the reaction conditions, after denaturation treatment at 96° C. for 3 minutes, reaction was carried out by 30 to 40 cycles, each cycle consisting of reaction at 94° C. for 1 minute, reaction at 55° C. for 1 minute and reaction at 72° C. for 1 minute, followed by reaction at 72° C. for 7 minutes. Hereinafter, unless otherwise indicated, a gene encoding a fusion protein in which myc/His was added to the C-terminal of human CLDN4 gene (hereinafter referred to as "CLDN4-myc/His") was amplified by carrying out PCR under the above-described reaction conditions. The nucleotide sequence and the amino acid sequence of CLDN4-myc/His are represented by SEQ ID NO:3 and SEQ ID NO:4, respectively. The reaction solution was separated by agarose gel electrophoresis, and the thus obtained gene fragment of about 0.7 kbp was extracted using Gel Extraction Kit (manufactured by QIAGEN). The thus obtained gene fragment was inserted into the SmaI, EcoRV or EcoRI-KpnI site of the pBluescript II SK(−) vector and ligated using Ligation high (manufactured by TOYOBO) and then *Escherichia coli* DH5α was transformed therewith by the method of Cohen et al. [*Proc, Nat, Acad. Sci. USA,* 69, 2100 (1972)]. By extracting plasmids from the thus obtained transformants using an automatic plasmid extraction device (manufactured by KURABO), a plasmid pBluescript SK(−)-CLDN4-myc/His having the nucleotide sequence represented by SEQ ID NO:3 was obtained.

The plasmid pBluescript SK(−)-CLDN4-myc/His was digested with EcoRI and KpnI, the gene fragment containing human CLDN4-myc/His was ligated to pKANTEX93 vector (WO 97/10354) which had been digested with EcoRI and KpnI, thereby obtaining a transformant by the above-mentioned method of Cohen et al., and then a plasmid pKANTEX-CLDN4-myc/His was obtained using plasmid extraction kit (manufactured by QIAGEN).

Next, the pKANTEX-CLDN4-myc/His was introduced into CHO/DG44 cell [*Somatic Cell and Molecular Genetics,* 12, 555 (1986)] by electroporation [*Cytotechnology,* 3, 133 (1990)] in the following manner.

The cell was used by sub-culturing it with a medium prepared by adding 1×HT supplement (manufactured by Life Technologies) to IMDM medium (manufactured by Life Technologies) supplemented with 10% fetal bovine serum (manufactured by Life Technologies) and 50 µg/ml Gentamicin (manufactured by Nacalai Tesque). The CHO/DG44 cells were suspended in a K-PBS buffer (a suspension of 137 nmol/l potassium chloride, 2.7 nmol/l sodium chloride, 8.1 mmol/l disodium hydrogenphosphate, 1.5 nmol/l sodium dihydrogenphosphate and 4 mmol/1 magnesium) to give a density of $8\times10^6$ cells/ml, and 200 µl of the cell suspension (contains $1.6\times10^6$ cells) was mixed with 10 µg of the above-mentioned plasmid. The mixture was transferred into a cuvette (interelectrode distance 2 mm), and gene transfer was carried out using GenePulserII (BioRad) device at 0.35 kV pulse voltage and 250 µF electric capacity. After allowing the curvette to stand still on ice, the cell suspension in the cuvette was suspended in a flask containing A3 medium and cultured in an incubator at 37° C. in the presence of 5% $CO_2$, Five days after culturing, sub-culturing was continued for a while by changing the medium to the A3 medium supplemented with 0.5 mg/ml G418 (manufactured by CALBIOCHEM), and a G418-resistant clone was obtained about 2 weeks after the gene transfer.

The thus obtained G418-resistant clone was diluted with the A3 medium supplemented with 0.5 mg/ml G418 to give a density of 5 cells/ml and dispensed at 100 µl into a 96-well plate, and 500 nmol/l methotrexate (hereinafter referred to as "MTX") was added thereto, followed by culturing to obtain MTX-resistant strains. As a result, a CLDN4-myc/His gene-introduced CHO cell clone (hereinafter referred to as "(CLDN4/CHO") was obtained.

(2) Construction of CLDN5-myc/His Gene-Introduced CHO Cell Clone

CLDN5-myc/His gene-introduced CHO cell clone (hereinafter referred to as "CLDN5/CHO") was prepared by amplifying a gene sequence encoding a fusion protein in which myc/His was added to the C-terminal of human CLDN5 gene polypeptide (hereinafter referred to as "CLDN5-myc/His") in the same manner as the case of the above-mentioned CLDN4/CHO cell, except that a plasmid comprising the human CLDN5 gene (SEQ ID NO:29) registered with Japan DNA Data Bank (AK092561) was used as die template, and primers comprising the nucleotide sequences represented by SEQ ID NO:41 and SEQ ID NO:42 were used. The nucleotide sequence and the amino acid sequence of the human CLDN5-myc/His are represented by SEQ ID NO:31 and SEQ ID NO:32, respectively.

(3) Construction of CLDN6-myc/His Gene-Introduced CHO Cell Clone

CLDN6-myc/His gene-introduced CHO cell clone (hereinafter referred to as "CLDN6/CHO") was prepared by amplifying a gene sequence encoding a fusion protein in which myc/His was added to the C-terminal of human CLDN6 gene polypeptide (hereinafter referred to as "CLDN6-myc/His") in the same manner as the case of the above-mentioned CLDN4/CHO cell, except that a plasmid comprising the human CLDN6 gene (SEQ ID NO:5) registered with Japan DNA Data Bank (XM_012518) was used as the template, and primers comprising the nucleotide sequences represented by SEQ ID NO:11 and SEQ ID NO:12 were used. The nucleotide sequence and the amino acid sequence of the human CLDN6-myc/His are represented by SEQ ID NO:7 and SEQ ID NO:8, respectively.

(4) Construction of CLDN3-myo/His Gene-Introduced CHO Cell Clone

PCR was carried out by preparing 20 µl of a reaction solution containing 5 µl of a large intestine tissue-derived cDNA purchased from BD Clontech as the template, 2 µl of 10×ExTaq buffer 1, 1.6 µl of 2.5 mmol/l dNTP, 1.6 µl of 25 mmol/l magnesium chloride, 1 µl of 0.1 µg/µl of each of the primers comprising the nucleotide sequences represented by SEQ ID NO:37 and SEQ ID NO:38, 0.1 µl of ExTaq polymerase (manufactured by Takara Shuzo) and 1 µl of dimethyl sulfoxide (hereinafter referred to as "DMSO"). Regarding the reaction conditions, after denaturation treatment at 96° C. for 3 minutes, reaction was carried out by 40 cycles, each cycle consisting of reaction at 95° C. for 1 minute, reaction at 50° C. for 1 minute and reaction at 72° C. for 1 minute, followed by reaction at 72° C. for 7 minutes. The reaction products were separated by agarose gel electrophoresis, and a gene fragment of about 0.7 kbp was extracted using Gel Extraction Kit (manufactured by QIAGEN), Thereafter, a plasmid pBluescript SK(−)-CLDN3-myc/His was obtained in the same manner as in Example 1-(1). Regarding the nucleotide sequence of CLDN3 contained in the plasmid pBluescript SK(−)-CLDN3-myc/His, A at position 557 in the nucleotide sequence of CLDN3 represented by SEQ ID NO:25 registered with Gene Bank as an accession No. NM-001306 was substituted with G, but the amino acid sequence encoded by this nucleotide sequence was identical to the CLDN3 amino acid sequence represented by SEQ ID NO:26.

Next, PCR was carried out by preparing a reaction solution using this as the template and primers comprising the nucleotide sequences represented by SEQ ID NO:39 and SEQ ID NO:40. After denaturation treatment at 96° C. for 3 minutes, PCR was carried out by 40 cycles, each cycle consisting of reaction at 95° C. for 1 minute, reaction at 50° C. for 1 minute and reaction at 72° C. for 1 minute at 72° C., followed by reaction at 72° C. for 7 minutes, thereby amplifying a gene fragment encoding a fusion protein in which myc/His was added to the C-terminal of human CLDN3 gene polypeptide (hereinafter referred to as "CLDN3-myc/His"). The reaction products were separated by agarose gel electrophoresis, and a gene fragment of about 0.7 kbp was extracted using Gel Extraction Kit (manufactured by QIAGEN). Thereafter, plasmids pBluescript SK(−)-CLDN3-myc/His and pKANTEX-CLDN3-myc/His both comprising the nucleotide sequence represented by SEQ ID NO:27 were obtained in the same manner as in Example 1-(1), and a CLDN3 high expression cell (hereinafter referred to as "CLDN3/CHO") was obtained.
(5) Construction of CLDN9-myc/His Gene-Introduced CHO Cell Clone PCR was carried out by preparing 50 µl of a reaction solution containing 5 µl of 10×KOD buffer 1, 5 µl of 2 mmol/l dNTP, 2 µl of 25 mmol/l magnesium chloride, 0.1 µl of 1 µg/µl of each of synthetic DNA fragments comprising the nucleotide sequences represented by SEQ ID NOs:43 to 48, 0.5 µl of KOD polymerase and 2.5 µl of DMSO. Regarding the reaction conditions, after denaturation treatment at 96° C. for 3 minutes, reaction was carried out by 25 cycles, each cycle consisting of reaction at 94° C. for 1 minute, reaction at 62° C. for 1 minute and reaction at 72° C. for 1 minute, followed by reaction at 72° C. for 7 minutes. As a result, a nucleotide sequence encoding a fusion protein in which myc/His was added to the C-terminal of human CLDN9 gene polypeptide (hereinafter referred to as "CLDN9-myc/His") was amplified. The nucleotide sequence and the amino acid sequence of the human CLDN9-myc/His are represented by SEQ ID NO:35 and SEQ ID NO:36, respectively. The reaction products were separated by agarose gel electrophoresis, and a gene fragment of about 0.7 kbp was extracted using the Gel Extraction Kit. Thereafter, plasmids pBluescript SK(−)-CLDN9-myc/His and pKANTEX-CLDN9-myc/His both comprising the nucleotide sequence represented by SEQ ID NO:35 were obtained in die same manner as in Example 1-(1), and a CLDN9 high expression cell (hereinafter referred to as "CLDN9/CHO") was obtained.

(6) Confirmation of CLDN-Expressing Cells

From 1 to 5×10$^6$ cells of each of die transformants obtained in the above-mentioned Example 1(1) to (5) were suspended in 1 ml of 70% ethanol-PBS and fixed at ice temperature for 30 minutes. After dispensing at 1 to 5×10$^6$ cells/well into a 96-well U-bottom plate and subsequent centrifugation (1,500 rpm, 5 minutes), the supernatant was discarded by blocking with BSA-PBS at ice temperature for 30 minutes. After removing the supernatant by centrifugation, a commercially available CLDN4 monoclonal antibody 3E2C1 (manufactured by Zymed) which recognizes the intracellular region of CLDN4, an anti-myc antibody PL14 (manufactured by MBL), an anti-His antibody (manufactured by QIAGEN) and a mouse IgG isotype control (manufactured by DAKO), as the primary antibodies, were diluted with BSA-PBS to give final concentrations of 0.5, 1, 0.1 and 0.1 µg/ml, respectively, and dispensed at 100 µl/well to carry out the reaction at ice temperature for 60 minutes. After the reaction and then washing with BSA-PBS once, an FITC-labeled anti-mouse immunoglobulin G (H+L) (manufactured by DAKO) diluted 50-fold with BSA-PBS was diluted with BSA-PBS and dispensed as the secondary antibody at 100 µl/well to carry out the reaction in the dark at ice temperature for 60 minutes. After again washing with BSA-PBS once, the cells were suspended in PBS and the fluorescence intensity was measured by a flow cytometer (hereinafter referred to as "FCM") (manufactured by Beckman Coulter).

A result thereof is shown in FIG. 1. As shown in FIG. 1, all antibodies of the anti-CLDN4 antibody, anti-myc antibody and anti-His antibody reacted with the CLDN4/CHO, so that it was found that the CLDN4 with which the myc tag and His tag were fused was expressed. On the other hand, the anti-CLDN4 antibody did not react with the CLDN3/CHO, CLDN5/CHO, CLDN6/CHO and CLDN9/CHO, but reacted with the anti-myo antibody and anti-His antibody, so that it was found that the CLDN4 with which the myc tag and His tag were fused was expressed in CLDN3/CHO, CLDN5/CHO, CLDN6/CHO and CLDN9/CHO.

EXAMPLE 2

Preparation of Anti-CLDN4 Monoclonal Antibody (1) Preparation of Immunogen

Pancreatic cancer cell line Capan-2 (ATCC HTB-80) or CLDN4/CHO was cultured for 3 to 5 days and peeled off using a 0.02% EDTA solution (manufactured by Nacalai Tesque) or a cell scraper. The cells were suspended in PBS and prepared to the number of cells of 6×10$^6$ to 1×10$^7$ per animal,
(2) Immunization of Animal and Preparation of Antibody Producing Cell Capan-2 cell prepared in Example 2-(1) was administered together with 1×10$^9$ cells of pertussis vaccine (manufactured by Chiba Serum Institute) to 3 animals/group a BXSB mouse of 6 weeks old (manufactured by Japan SLC). One week after the administration, the cells were administered once a week, 4 times in all, and blood was partially collected from the fundus of the eye of the mice. By carrying out the fluorescent antibody staining shown in Example 2-(3), its blood antibody titer was measured by ABI 8200 Cellular Detection System (manufactured by Applied Biosystems) or FCM (manufactured by Beckman Coulter), and the spleen was extracted from a mouse which showed sufficient antibody titer 3 days after the final immunization.

The spleen was cut to pieces in MEM (Minimum essential medium) (manufactured by Nissui Pharmaceutical), unbound using a pair of forceps and centrifuged (250×g, 5 minutes). Erythrocytes were removed by adding Tris-ammonium chloride buffer (pH 7.6) to the thus obtained precipitation fraction and treating it for 1 to 2 minutes. The thus obtained precipitation fraction (cell fraction) was washed three times with MEM and used for the cell fusion.

(3) Fluorescent Antibody Staining Using Cells (ABI 8200 Cellular Detection System)

As the cells for assay, CLDN4/CHO and CHO cell transfected with pKANTEX93 alone (vector/CHO) were used. The CLDN4/CHO and vector/CHO cells were cultured for 2 to 3 days in Iscove's modified Dulbecco's medium (manufactured by Invitrogen) supplemented with 10% FCS, and the resulting cells were peeled off using Trypsin-EDTA solution (manufactured by Invitrogen), suspended in the medium, inoculated at $1 \times 10^4$ cells/50 μl medium/well into a 96-well black plate for ABI 8200 and cultured overnight. A mouse anti-serum to be immunized and a hybridoma culture supernatant were dispensed as the primary antibodies at 10 μl/well into the plate, and ALEXA 647-labeled anti-mouse immunoglobulin G (H+L) (manufactured by Invitrogen) was added thereto as the secondary antibody at 100 μl/well and allowed to stand for 4 hours under shading. A wavelength of from 650 to 685 nm excited with a laser 633 He/Ne was measured by the ABI 8200 Cellular Detection System (manufactured by Applied Biosystems).

(4) Fluorescent Antibody Staining Using Cells

As the cells for assay, CLDN4/CHO and vector/CHO were used. CLDN4/CHO and vector/CHO cells were cultured for 2 to 3 days in Iscove's modified Dulbecco's medium (manufactured by Invitrogen) supplemented with 10% FCS, and the resulting respective cells were peeled off using 0.02% EDTA solution (manufactured by Nacalai Tesque) and washed with PBS. In order to prevent nonspecific adsorption of antibodies, the cells were blocked using BSA-PBS at ice temperature for 20 minutes. The cells were dispensed at $5 \times 10^5$ cells/50 μl BSA-PBS into a 96-well U bottom plate and centrifuged (1,800 rpm, 2 minutes), the supernatant was removed and then a mouse anti-serum to be immunized and a hybridoma culture supernatant were dispensed as the primary antibodies at 50 μl/well and allowed to react at ice temperature for 30 minutes. After the reaction and then washing three times by centrifugation using PBS, ALEXA 488-labeled anti-mouse immunoglobulin G (H+L) (manufactured by Invitrogen) was added thereto as the secondary antibody at 50 μl/well and allowed to react at ice temperature for 30 minutes under shading. After washing again three times by centrifugation using PBS and subsequently suspending in PBS, a wavelength of 510 to 530 nm n excited by a laser 488 in argon was measured by FCM (manufactured by Beckman Coulter).

(5) Preparation of Mouse Myeloma Cell

8-Azaguanine-resistant mouse myeloma cell line P3X63Ag8U.1 (P3-U1; purchased from ATCC) was cultured using a normal medium (10% FCS RPMI medium), and $2 \times 10^7$ or more of cells were saved at the time of cell fusion and subjected to the cell fusion as the parent cell line.

(6) Preparation of Hybridoma

The mouse spleen cells obtained in Example 2-(2) and the myeloma cells obtained in Example 2-(5) were mixed at a ratio of 10:1 and centrifuged (250×g, 5 minutes). After thoroughly loosening a group of cells of the thus obtained precipitation fraction, a mixed solution of 1 g of polyethylene glycol-1000 (PEG-1000), 1 ml of MEM medium and 0.35 ml of dimethyl sulfoxide was added thereto, in an amount of 0.5 ml per $10^8$ mouse spleen cells, at 37° C. under stirring, 1 ml of the MEM medium was added to the suspension several times at intervals of 1 to 2 minutes, and then the total volume was adjusted to 50 ml by adding the MEM medium.

The suspension was centrifuged (900 rpm, 5 minutes), cells of the thus obtained precipitation fraction were mildly loosened, and then the cells were gently suspended in 100 ml of a HAT medium [a medium prepared by adding HAT Media Supplement (manufactured by Invitrogen) to 10% fetal bovine serum-supplemented RPMI medium] by repeated drawing up into and discharging from a measuring pipette. The suspension was dispensed at 200 μl/well into a 96-well culture plate and cultured in a 5% $CO_2$ incubator at 37° C. for 8 to 10 days.

Figure 3:
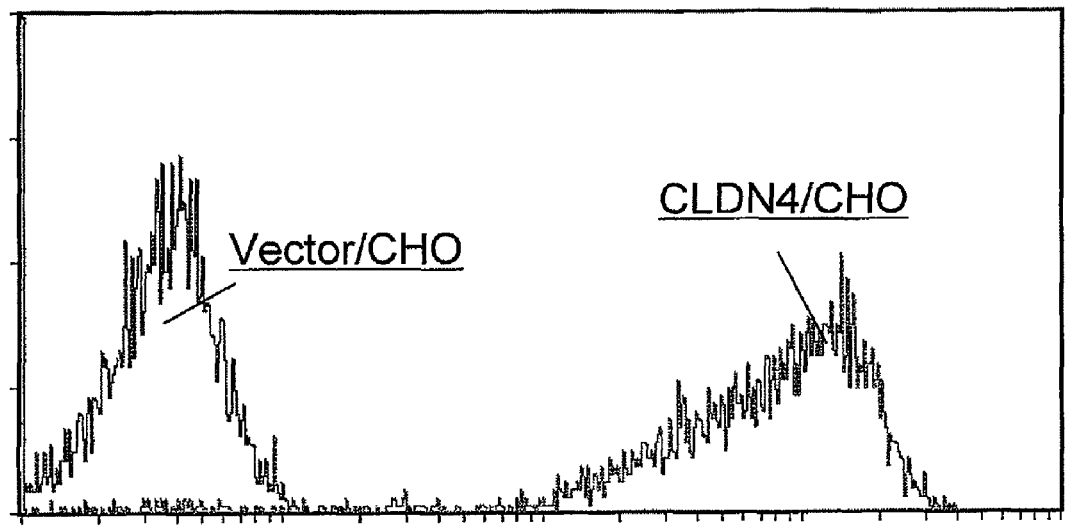
FIG. 3 shows results in which the reactivity of an anti-CLDN4 monoclonal antibody KM3900 for CLDN4-myc/His gene-introduced CHO cell (CLDN4/CHO) and vector-introduced CHO cell (Vector/CHO) was measured by FCM. The ordinate shows the number of cells, and the abscissa shows fluorescence intensity.

After the culturing, the culture supernatant was checked by fluorescent antibody staining described in Example 2-(3) and 2-(4), thereby selecting wells which reacted with the CLDN4/CHO clone but did not react with the vector/CHO, and cloning from the cells contained in the wells by the limiting dilution method was repeated twice. An anti-CLDN4 monoclonal antibody-producing hybridoma KM3900 (FIG. 2, FIG. 3) and hybridoma KM3907 were established.

(7) Purification of Monoclonal Antibody

Each of the hybridoma cell lines obtained in Example 2-(6) was intraperitoneally injected into pristane-treated female nude mice of 7 weeks old (ICR) at a dose of 5 to $20 \times 10^6$ cells/animal. Ten to twenty-one days thereafter, ascitic fluid was collected from the mice in which the hybridoma caused ascites tumor to generate the ascitic fluid (1 to 8 ml/animal).

The ascetic fluid was centrifuged (1,200×g, 5 minutes) to remove the solid matter. A purified IgG monoclonal antibody was obtained by purifying by the caprylic acid precipitation method [*Antibodies—A Laboratory Manual*, Cold Spring Harbor Laboratory (1988)]. Determination of subclass of the monoclonal antibody was carried out by the method of Example 2-(3), and a subclass-specific ALEXA 647-labeled anti-mouse immunoglobulin (manufactured by Invitrogen) was used as the secondary antibody. As a result, it was found that the subclass of the respective antibodies was mouse IgG2a subclass in both cases of the KM3900 and KM3907.

EXAMPLE 3

Examination of Reactivity of Anti-CLDN4 Monoclonal Antibodies (1) Detection of CLDN3 or CLDN4 by Western Blotting Using Anti-CLDN4 Monoclonal Antibodies KM3900 and KM3907

Figure 4:
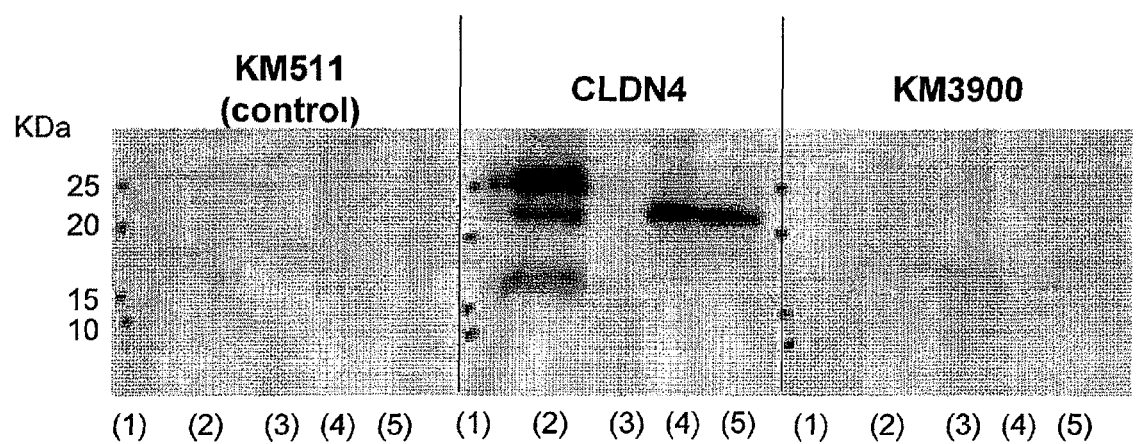
FIG. 4 shows the reactivity of an anti-CLDN4 monoclonal antibody KM3900 by Western blotting. From the left side of the lane, (1) molecular weight marker, (2) CLDN4-myc/His gene-introduced CHO cell (CLDN4/CHO), (3) vector-introduced CHO cell (Vector/CHO), (4) Capan-2 and (5) HPAF-II are shown.
Figure 6:
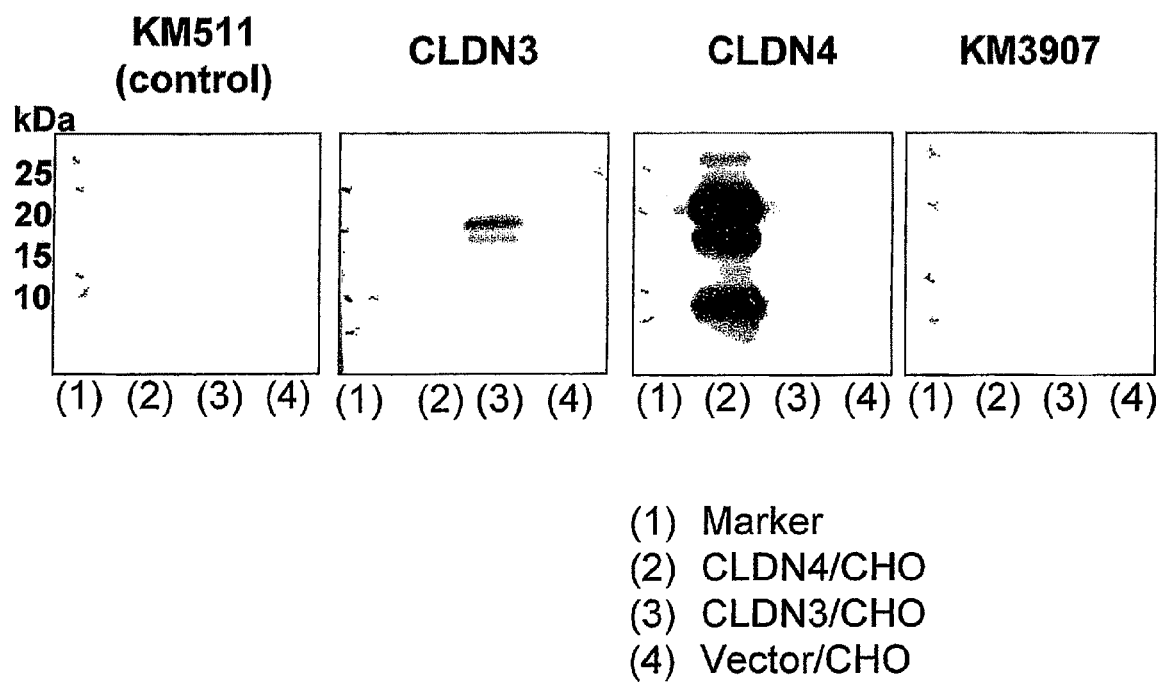
FIG. 6 shows results in which the reactivity of an anti-CLDN4 monoclonal antibody KM3907 for CLDN3 protein and CLDN4 protein was examined by Western blotting. From the left side of the lane, (1) molecular weight marker, (2) CLDN4/CHO, (3) CLDN3/CHO and (4) vector-introduced CHO cell (Vector/CHO) are shown. An anti-CLDN4 monoclonal antibody KM3907 was used as an antibody to be detected, an anti-GS CSF derivative antibody KM511 was used as a negative control antibody to be detected, and a commercially available anti-CLDN3 polyclonal antibody or an anti-CLDN4 monoclonal antibody 3E2C1 was used as a positive control antibody to be detected.

SDS-polyacrylamide electrophoresis was carried out by preparing respective cell extracts from $5 \times 10^4$ cells of CLDN4/CHO, vector/CHO, pancreatic cancer cell lines Capan-2 (ATCC HTB-80) and HPAF-II (ATCC CRL-1997). Thereafter, they were transferred onto a PVDF membrane (manufactured by Millipore), and the membrane was blocked with BSA-PBS. After removing the BSA-PBS, a commercially available positive control antibody, anti-CLDN4 monoclonal antibody 3E2C1 (manufactured by Zymed), a culture supernatant of the hybridoma KM3900, a culture supernatant of the hybridoma KM3907 or a negative control antibody KM511 (anti-G-CSF derivative antibody) [*Agric. Biol. Chem.*, 53, 1095 (1989)] was allowed as the primary antibody to react with the membrane at 4° C. overnight. The membrane was thoroughly washed with Tween-PBS, and peroxidase-labeled anti-mouse immunoglobulin G (H+L) (manufactured by Zymed) was allowed to react therewith at room temperature for 1 hour. The membrane was thoroughly washed with Tween-PBS again, and an antibody-bound band was detected using ECL™ Western blotting detection reagents (manufactured by Amersham Pharmacia). As a result, the commercially available anti-CLDN4 monoclonal antibody 3E2C1 was able to detect the CLDN4 protein, but the monoclonal antibodies KM3900 and KM3907 were unable to detect the CLDN4 protein (FIG. 4, FIG. 6).

In the same manner, a cell extract was prepared from CLDN3/CHO, and the reactivity of KM3907 for CLDN3 was examined. As a result, a commercially available anti-CLDN3 polyclonal antibody (manufactured by Zymed) was able to detect the CLDN3 protein, but the monoclonal antibody KM3907 was unable to detect CLDN3 (FIG. 6).

(2) Detection of CLDN3 or CLDN4 by Immunoprecipitation Using Anti-CLDN4 Monoclonal Antibodies KM3900 and KM3907

To a 96-well ELISA plate, 50 µg/ml in concentration of KM3900 or KM3907 was added at 100 µl/well and allowed to react at 4° C. overnight, and after washing with PBS, blocking was carried out using BSA-PBS in order to prevent nonspecific adsorption. To $5 \times 10^7$ cells of CLDN4/CHO, Vector/CHO, CLDN6/CHO, human pancreatic cancer cell line Capan-2 or HPAF-II, 1 ml of a cell lysis buffer [50 mmol/l Tris-HCl (pH 7.2), 1% Triton X-100, 150 mmol/l NaCl, 2 mmol/l $MgCl_2$, 2 mmol/l $CaCl_2$, 0.1% $NaN_3$, 50 mmol/l iodoacetamide, 50 mmol/l N-ethylmaleimide, 1 mg/ml leupeptin, 0.1 mmol/l dithiothreitol] was added, allowed to stand at 4° C. for 2 hours and then centrifuged to prepare a cell extract. After discarding BSA-PBS, the thus prepared cell extract was dispensed at 50 µl/well into the plate and allowed to stand at 4° C. overnight. After washing the plate with Tween-PBS, immunoblotting was carried out using those which were dissolved using an SDS-PAGE sample buffer [2% SDS, 62 mmol/l tris-HCl (pH 6.8), 10% glycerol] as the samples.

Figure 5:
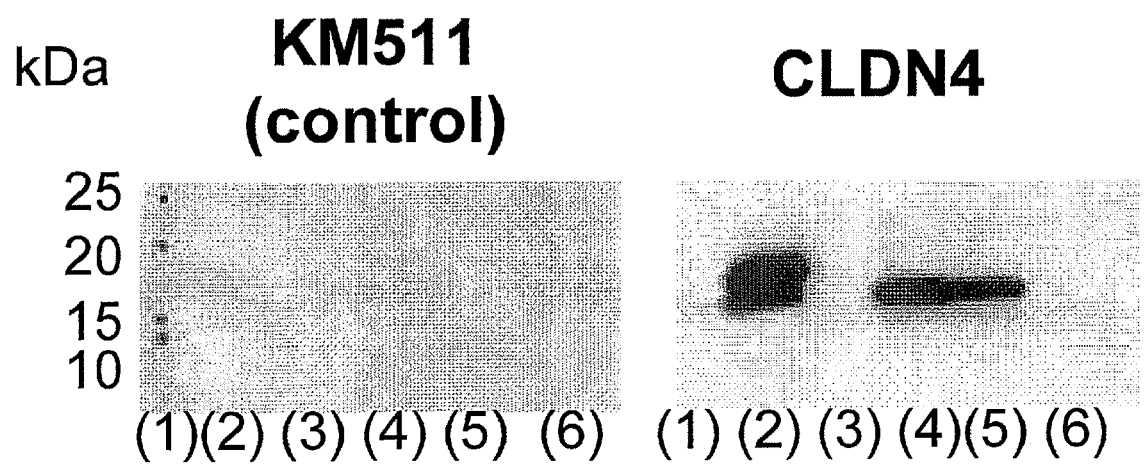
FIG. 5 shows the reactivity of an anti-CLDN4 monoclonal antibody KM3900 by immunoprecipitation. From the left side of the lanes (1) molecular weight marker, (2) CLDN4-myc/His gene-introduced CHO cell (CLDN4/CHO), (3) vector-introduced CHO cell (Vector/CHO), (4) Capan-2, (5) HPAF-II and (6) CLDN6-myc/His gene-introduced CHO cell (CLDN6/CHO) are shown.

The sample after SDS-polyacrylamide electrophoresis was transferred onto a PVDF membrane (manufactured by Millipore), and the membrane was blocked using BSA-PBS. After removing the BSA-PBS, 1 µg/ml of a commercially available anti-CLDN4 monoclonal antibody 3E2C1 (manufactured by Zymed) or anti-CLDN3 polyclonal antibody (manufactured by Zymed) as the positive control antibody, or KM511 (anti-G-CSF derivative antibody) as negative control antibody, was allowed to react with the membrane at room temperature for 2 hours. After the reaction, the membrane was thoroughly washed with Tween-PBS, and peroxidase-labeled anti-mouse immunoglobulin G (H+L) (manufactured by Zymed) was allowed to react therewith at room temperature for 1 hour. The membrane was thoroughly washed with Tween-PBS again, and an antibody-bound band was detected using ECL™ Western blotting detection reagents (manufactured by Amersham Pharmacia). As a result, since a band was detected at around 22 kDa in molecular weight, it was shown that the anti-CLDN4 monoclonal antibodies KM3900 and KM3907 are antibodies which can immuno-precipitate CLDN4 (FIG. 5, FIG. 7).

In the same manner, a cell extract was prepared from CLDN3/CHO, and the reactivity of anti-CLDN4 monoclonal antibody KM3907 for CLDN3 was examined. As a result, since a band was detected at around 22 kDa in molecular weight, it was shown that the anti-CLDN4 monoclonal antibody KM3907 is an antibody which can immuno-precipitate CLDN3 (FIG. 7).

Accordingly, it was found that the anti-CLDN4 monoclonal antibodies KM3900 and KM3907 of the present invention are antibodies which do not react with a denatured CLDN4 protein but react only a CLDN4 protein maintaining three-dimensional structure.

(3) Reactivity of Anti-CLDN4 Monoclonal Antibodies KM3900 and KM3907 for CLDN3, CLDN4, CLDN5, CLDN6 and CLDN9

Each of CLDN3/CHO, CLDN4/CHO, CLDN5/CHO, CLDN6/CHO and CLDN9/CHO was cultured for 3 to 4 days and peeled off using 0.02% EDTA solution (manufactured by Nacalai Tesque), and the recovered cells were washed with PBS and, in order to avoid nonspecific adsorption of antibodies, blocked at ice temperature for 30 minutes. The cells were dispensed at 1 to $5 \times 10^5$ cells/100 µl BSA-PBS into a 96-well U bottom plate and centrifuged (1,500 rpm, 5 minutes), the supernatant was removed and then a mouse anti-serum to be immunized, a culture supernatant of hybridoma KM3900 (8.6 µg/ml), anti-CLDN4 monoclonal antibodies KM3900 and KM3907 diluted to 5 µg/ml and a mouse IgG2a isotype control (manufactured by DAKO) were dispensed as the primary antibodies at 100 µl/well and allowed to react at ice temperature for 60 minutes. After the reaction and then washing with BSA-PBS once, FITC-labeled anti-mouse immunoglobulin G (H+L) (manufactured by DAKO) diluted 50-fold with BSA-PBS was added thereto as the secondary antibody at 100 µl/well and allowed to react at ice temperature for 30 minutes under shading. After washing again once with BSA-PBS and subsequently suspending in PBS, the fluorescent intensity was measured by FCM (manufactured by Beckman Coulter).

The reactivity for respective cells is shown in the following Table 1, and a histogram of the typical reaction is shown in FIG. 8.

TABLE 1

Reactivity of anti-CLDN4 monoclonal antibody

| | CLDN-expressing cells | | | | |
|---|---|---|---|---|---|
| Antibody | CLDN3 | CLDN4 | CLDN5 | CLDN6 | CLDN9 |
| KM3900 | − | + | − | − | − |
| KM3907 | + | + | − | − | − |

As shown in Table 1, the anti-CLDN4 monoclonal antibody KM3900 reacted only with CLDN4/CHO but did not react with other CLDN-expressing cells. In addition, the anti-CLDN4 monoclonal antibody KM3907 reacted with both of CLDN3/CHO and CLDN4/CHO but did not react with other CLDN-expressing cells. Accordingly, it was found that the anti-CLDN4 monoclonal antibodies KM3900 and KM3907 recognize three-dimensional structure of an extracellular region of CLDN4 expressed in cells and bind thereto. In addition, it was found that the anti-CLDN4 monoclonal antibody KM3907 recognizes the extracellular region of both CLDN4 and CLDN3 and binds thereto.

(4) Reactivity of Anti-CLDN4 Monoclonal Antibodies for Cancer Cells

Human pancreatic cancer cell lines Capan-2 and HPAF-II human lymphoma cell line Daudi (ATCC CCL-213), human breast cancer cell line MCF7 (ATCC HTB-22), human colorectal cancer cell lines HT-29 (ATCC HTB-38) and SW480 (ATCC CCL-228) and human prostate cancer cell line s 22Rv1 (ATCC CRL-2505), DU 145 (ATCC HTB-81) and PC-3 (ATCC CRL-1435) were cultured for 3 to 4 days, and adhered cells were peeled off using 0.02% EDTA solution (manufactured by Nacalai Tesque) to recover the cells. The thus recovered cells were washed with PBS and, in order to prevent nonspecific adsorption of antibodies, blocked at ice temperature for 30 minutes using BSA-PBS. The cells were dispensed at 1 to $5 \times 10^5$ cells/100 µl BSA-PBS into a 96-well U bottom plate and centrifuged (1,500 rpm, 5 minutes), the supernatant was removed and then a mouse anti-serum to be immunized, a culture supernatant of hybridoma KM3900 (8.6 μg/ml), anti-CLDN4 monoclonal antibodies KM3900 and KM3907 diluted to 5 μg/ml or a mouse IgG2a isotype control (manufactured by DAKO) was dispensed as the primary antibody at 100 μl/well and allowed to react at ice temperature for 60 minutes. After washing with BSA-PBS once, FITC-labeled anti-mouse immunoglobulin G (H+L) (manufactured by DAKO) 50 times-diluted with BSA-PBS was added thereto as the secondary antibody at 100 μl/well and allowed to react at ice temperature for 30 minutes under shading. After the reaction, the cells were washed once with BSA-PBS and suspended in PBS, and the fluorescent intensity was measured by FCM (manufactured by Beckman Coulter).

A histogram when 8.6 μg/ml of the anti-CLDN4 monoclonal antibody KM3900 was allowed to react with human pancreatic cancer cell lines Capan-2 and HPAF-II and human lymphoma cell line Daudi (ATCC CCL-213) is shown in FIG. 9. As shown in FIG. 9, die anti-CLDN4 monoclonal antibody KM3900 strongly bound to the human pancreatic cancer cell lines Capan-2 and HPAF-II, but hardly bound to the human lymphoma cell line Daudi.

Figure 10:
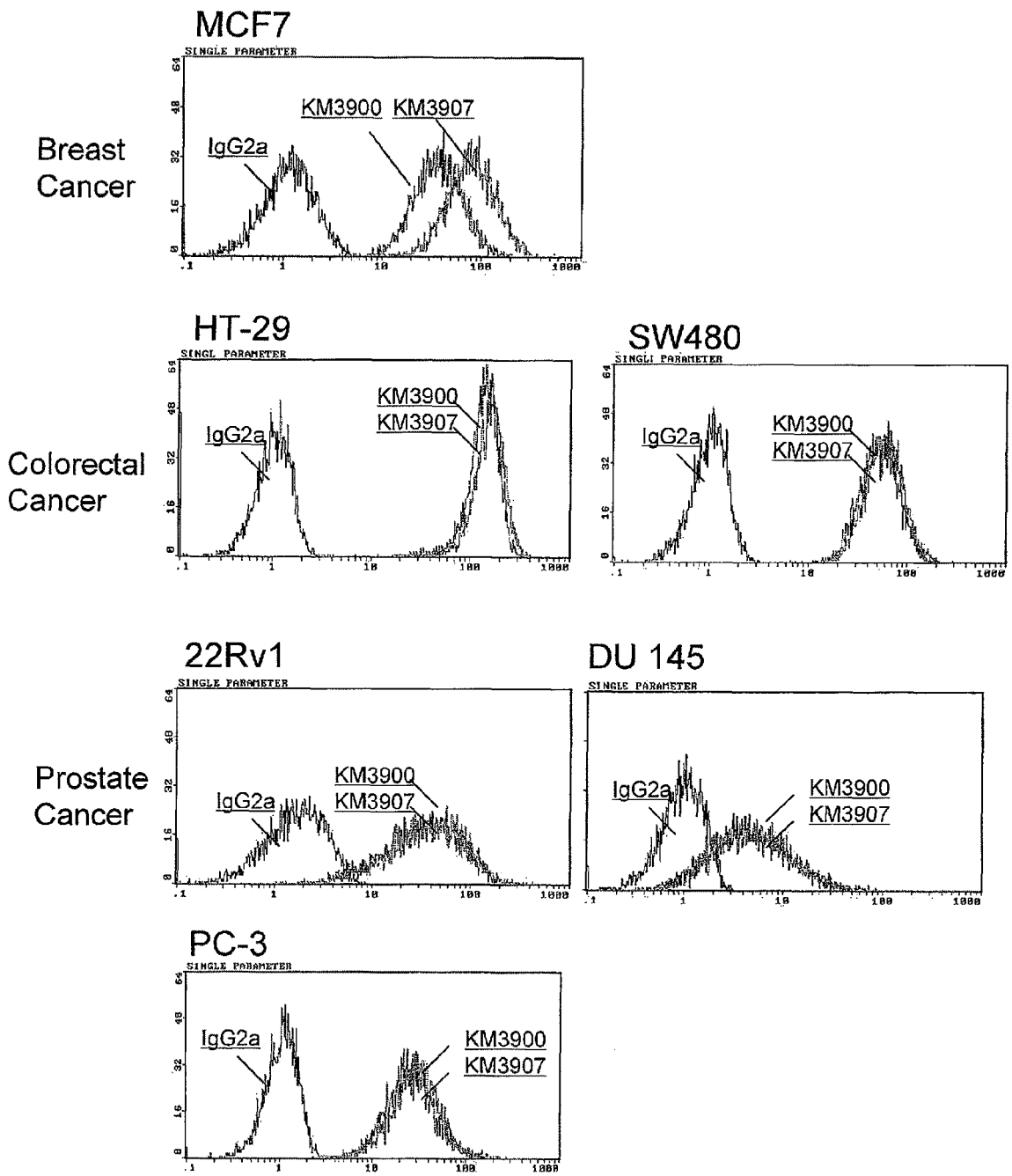
FIG. 10 shows results in which the reactivity of a negative control antibody mouse IgG2a and anti-CLDN4 monoclonal antibodies KM3900 and KM3907 for human cancer cell lines, MCF7 (breast cancer), HT-29 (colorectal cancer), SW480 (colorectal cancer), 22Rv1 (prostate cancer), DU145 prostate cancer) and PC-3 (prostate cancer), was measured by FCM. The ordinate shows the number of cells, and the abscissa shows fluorescence intensity.

In addition, a histogram when 5 μg/ml of the anti-CLDN4 monoclonal antibody KM3900 or KM3907 was allowed to react with human breast cancer cell line MCF7 (ATCC HTB-22), human colorectal cancer cell lines FIT-29 (ATCC HTB-38) and SW480 (ATCC CCL-228) and human prostate cancer cell lines 22Rv1 (ATCC CRL-2505), DU 145 (ATCC HTB-81) and PC-3 (ATCC CRL-1435) is shown in FIG. 10. As shown in FIG. 10, it was found that die anti-CLDN4 monoclonal antibodies KM3900 and KM3907 strongly bind to the human breast cancer cell line MCF7, human colorectal cancer cell lines HT-29 and SW480 and human prostate cancer cell lines 22Rv1, DU 145 and PC-3.

Accordingly, it was found that the anti-CLDN4 monoclonal antibodies KM3900 and KM3907 strongly bind to the CLDN4 expressed in breast cancer cells, colorectal cancer cells and prostate cancer cells.

EXAMPLE 4

Figure 12:
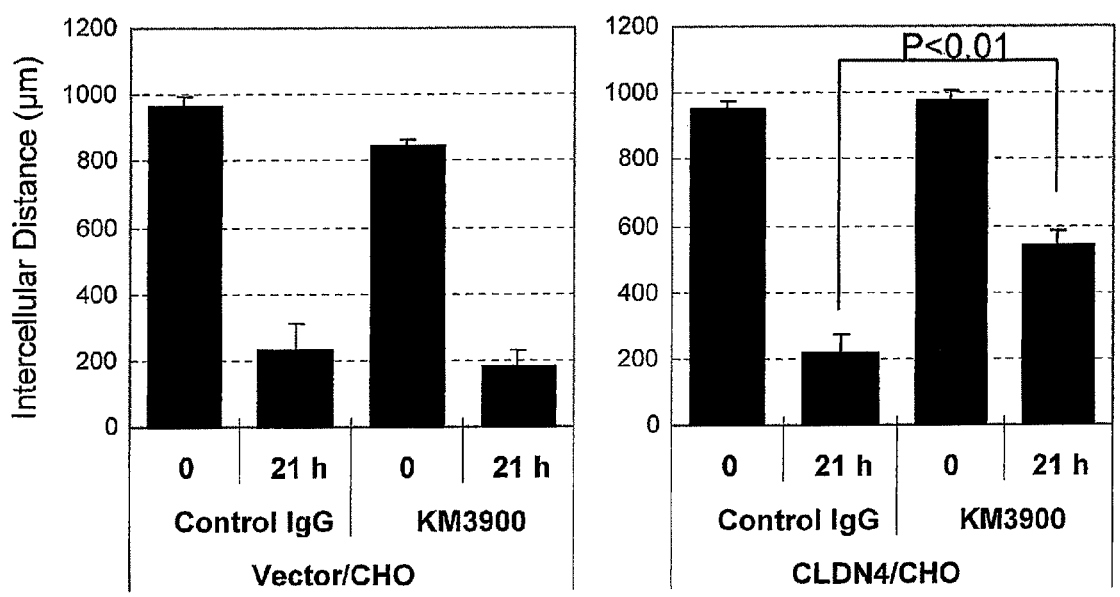
FIG. 12 shows results in which the intercellular distances of a cell peeling area before adding an anti-G-CSF derivative antibody KM511 as a negative control antibody and an anti-CLDN4 monoclonal antibody KM3900 at a concentration of 1 µg/ml to CLDN4-myc/His gene-introduced CHO cell (CLDN4/CHO) and vector-introduced CHO cell (Vector/CHO) (0 h), or when culturing was carried out for 21 hours after the addition (21 h), by the wound healing method, were measured and made into a graph. The ordinate shows intercellular distance (µm), and the abscissa shows culture time and treated antibodies.

Neutralizing Activity for CLDN4 by Anti-CLDN4 Monoclonal Antibodies (1) Effect of KM3900 Upon Cell Movement Ability by Wound Healing Method CLDN4/CHO or vector/CHO was inoculated at $3\times10^4$ cells/100 μl/well into a 96-well plate and cultured for 2 days, and then a part of the monolayer-cultured cell was peeled off by drawing a vertical line with the point of a chip. The anti-CLDN4 monoclonal antibody KM3900 and a negative control antibody KM511 (anti-G-CSF derivative antibody) were added to the medium to give a final concentration of 1 μg/ml and cultured for 21 hours. By photographing the peeled area before the antibody addition (0 h) and twenty-one hours after the culturing (21 h), the intercellular distance was measured. A photographic image in the case of CLDN4/CHO is shown in FIG. 11. In addition, a graph summarizing the results of carrying out using 6 wells for each group is shown in FIG. 12.

As a result, a tendency of inhibiting reduction of intercellular distance was confirmed in the wells of CLDN4/CHO to which KM3900 was added, and the cell movement ability of CLDN4/CHO was significantly inhibited in comparison with KMI511 (Students test, $P<0.01$). On the other hand, in the case of the Vector/CHO, difference in the reduction of intercellular distance between the KM3900 addition and KM511 addition was not found.

Based on the above results, it was found that the anti-CLDN4 monoclonal antibody KM3900 inhibits the cell movement ability of CLDN4 expression cells.

EXAMPLE 5

Examination of Reactivity of an Anti-CLDN4 Monoclonal Antibody 4A4 Manufactured by Abnova, by FCM CLDN4/CHO, vector/CHO and human pancreatic cancer cell line Capan-2 were cultured for 3 to 4 days, and adhered cells were peeled off using 0.02% EDTA solution (manufactured by Nacalai Tesque) to recover the cells. The thus recovered cells were washed with PBS and, in order to avoid nonspecific adsorption of antibodies, blocked at ice temperature for 30 minutes using BSA-PBS. The cells were dispensed at 1 to $5\times10^5$ cells/100 μl BSA-PBS into a 96-well U bottom plate and centrifuged (1,500 rpm, 5 minutes), the supernatant was removed and then 5 μg/ml of an anti-CLDN4 monoclonal antibody 4A4 (manufactured by Abnova) diluted to 5 μg/ml with BSA-PBS or BSA-PBS was dispensed at 100 μl/well and allowed to react at ice temperature for 60 minutes. After washing once with BSA-PBS, FITC-labeled anti-mouse immunoglobulin G (H+L) (manufactured by DAKO) diluted 50-fold with BSA-PBS was added thereto as the secondary antibody at 100 μl/well and allowed to react at ice temperature for 30 minutes under shading. After the reaction, the cells were washed once with BSA-PBS and suspended in PBS, and the fluorescent intensity was measured by FCM (manufactured by Beckman Coulter).

Figure 13:
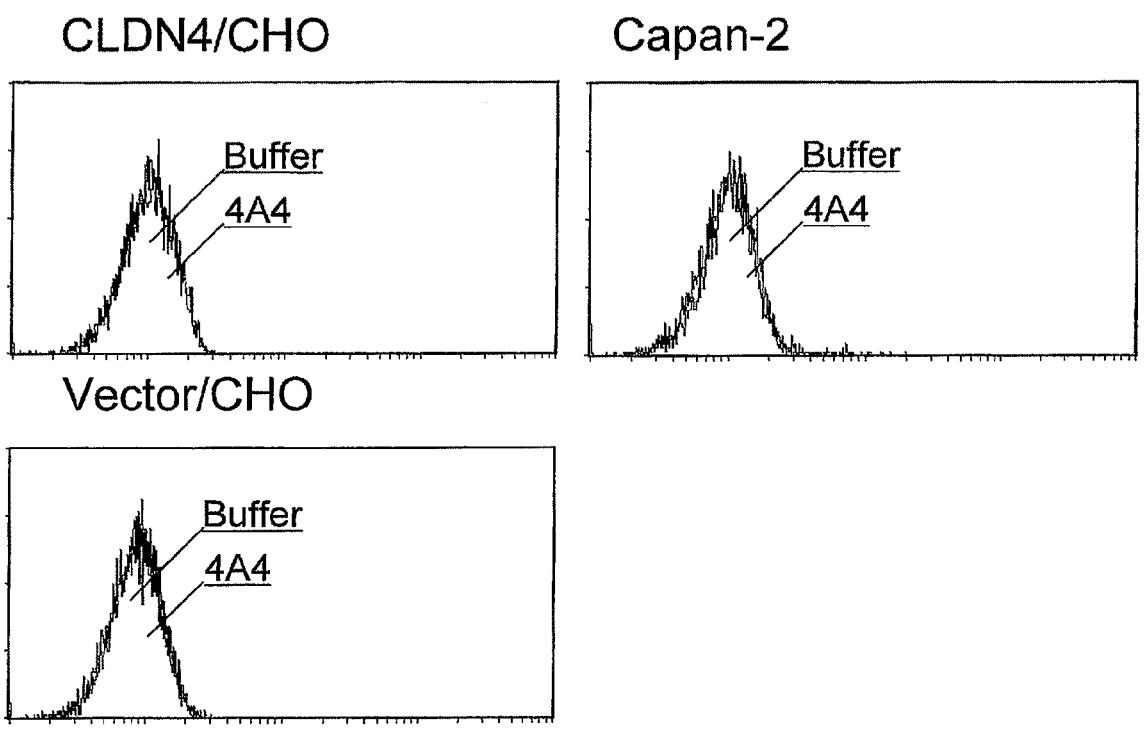
FIG. 13 shows results in which the reactivity of a commercially available anti-CLDN4 monoclonal antibody 4A4 for CLDN4-myc/His gene-introduced CHO cell (CLDN4/CHO), vector-introduced CHO cell (Vector/CHO) and human pancreatic cancer cell line Capan-2 was measured by FCM. An antibody non-addition (buffer) was set as the negative control. The ordinate shows the number of cells, and the abscissa shows fluorescence intensity.

A histogram when 5 μg/ml of the anti-CLDN4 monoclonal antibody 4A4 was allowed to react with CLDN4/CHO, vector/CHO and human pancreatic cancer cell lines Capan-2 is shown in FIG. 13. As a result, the commercially available anti-CLDN4 monoclonal antibody 4A4 did not bind to CLDN4/CHO and human pancreatic cancer cell line Capan-2. Based on the above, it was found that the anti-CLDN4 monoclonal antibody 4A4 is a monoclonal antibody which cannot recognize three-dimensional structure of the extracellular region and bind thereto.

EXAMPLE 6

Isolation and Analysis of cDNA Encoding the Variable Regions of Anti-CLDN4 Monoclonal Antibodies (1) Preparation of mRNA from Anti-CLDN4 Monoclonal Antibody Producer Hybridoma Cells Using the hybridomas KM43900 and KM3907 described in Example 2, mRNA of a mouse monoclonal antibody KM3900 and mRNA of a mouse monoclonal antibody KM3907 were prepared from $5\times10^7$ cells of the respective hybridoma cells, using RNAeasy Maxi Kit (manufactured by QIAGEN) and Oligotex™-dT30<Super>mRNA Purification Kit (manufactured by Takara) in accordance with the instructions attached thereto.

(2) Gene Cloning of H Chain and L Chain Variable Regions of Anti-CLDN4 Monoclonal Antibodies KM3900 and KM3907

Using BD SMART™ RACE cDNA Amplification Kit (manufactured by BD Biosciences) and in accordance with the instructions attached thereto, a cDNA having the BD SMART II™ A Oligonucleotide sequence attached to the kit at the 5'-terminal was obtained from 1 μg of the mRNA of anti-CLDN4 monoclonal antibody KM3900 obtained in Example 5-(1). A cDNA fragment of VH was amplified by carrying out PCR using the thus obtained cDNA as the template and using a universal primer Amix attached to the kit and die mouse Ig(γ)-specific primer (mG2aa2) represented by SEQ ID NO:13. Also, a cDNA fragment of VL was amplified by carrying out PCR using the mouse Ig(κ)-specific primer (mKa1) represented by SEQ ID NO:14 instead of the mouse Ig(γ)-specific primer.

In the PCR, after heating at 94° C. for 5 minutes, reaction was carried out by 5 cycles, each cycle consisting of reaction at 94° C. for 30 minutes reaction at 72° C. for 3 minutes; 5 cycles, each cycle consisting of reaction at 94° C. for 30 seconds, reaction at 70° C. for 30 seconds and reaction at 72° C. for 3 minutes at 72° C.; and 30 cycles, each cycle consisting of reaction at 94° C. for 30 seconds, reaction at 68° C. for 30 seconds and reaction at 72° for 3 minutes, followed by reaction at 72° for 10 minutes. The PCR was carried out using PTC-200 DNA Engine (manufactured by BioRad). The thus obtained PCR product was about 600 bp in size both on the KM3900H chain and KM3900 L chain. Also, the size of the KM3907H chain was 600 bp, and that of KM3907 L chain was 800 bp.

In order to determine nucleotide sequences of the thus obtained PCR products, they were separated by agarose gel electrophoresis, and each PCR product was extracted using Gel Extraction Lit (manufactured by QIAGEN). The thus obtained extraction fragment was ligated to the pBluescript II SK(-) vector digested with SmaI using Ligation high (manufactured by TOYOBO) and then transformed into *Escherichia coli* DHSA by the method of Cohen et al. [*Proc. Natl. Acad. Sci. USA*, 69, 2100 (1972)]. Plasmids were extracted from die thus obtained transformants using an automatic plasmid extraction device (manufactured by KURABO) and allowed to react using BigDye Terminator Cyclesequencing FS Ready Reaction Kit (manufactured by PE Biosystems) in accordance with the instructions attached thereto, and then their nucleotide sequences were analyzed by a sequencer of the same company, ABI PRISM 3700. As a result, a plasmid comprising complete length H chain cDNA and a plasmid comprising complete length L chain cDNA, in which an ATG sequence considered to be the initiation codon is present in the 5'-terminal of the cDNA, were obtained.

As a result, a plasmid KM3900VH_H202 comprising the H chain cDNA and a plasmid KM3900VL_$K_{23}$ comprising the L chain cDNA were obtained from the hybridoma KM3900, and a plasmid KM3907G2a101 comprising the H chain cDNA and a plasmid KM3907Ka103 comprising the L chain cDNA were obtained from the hybridoma KM3907.

(3) Analysis of V Region Amino Acid Sequences of Anti-CLDN4 Monoclonal Antibodies Complete nucleotide sequence of the VH contained in the plasmid KM3900VH_1-H202 is represented by SEQ ID NO:15, complete amino acid sequence of the secretion type VH including a signal sequence deduced from the nucleotide sequence is represented by SEQ ID NO:16, complete nucleotide sequence of the VL contained in the plasmid KM3900VL_K23 is represented by SEQ ID NO:17, and complete amino acid sequence of the secretion type VL including a signal sequence deduced from the nucleotide sequence is represented by SEQ ID NO:18. Based on the comparison with the conventionally known sequence data on mouse antibodies [*SEQUENCES of Proteins of Immunological Interest*, US Dept. Health and Human Services (1991)] and the comparison with a result of the analysis of the H chain and L chain N-terminal amino acid sequences of the purified anti-CLDN4 monoclonal antibody KM3900 carried out using a protein sequencer (PPSQ-10; manufactured by Shimadzu Corporation), it was found that the isolated each cDNA is a complete length cDNA encoding the anti-CLDN4 monoclonal antibody KM3900 including a secretion signal sequence, and the sequence at positions 1 to 19 of the amino acid sequence represented by SEQ ID NO:16 is the secretion signal sequence regarding the H chain, and the sequence at positions 1 to 22 of the amino acid sequence represented by SEQ ID NO:18 is the secretion signal sequence regarding the L chain.

In addition, complete nucleotide sequence of the VH contained in the plasmid KM3907G2a101 is represented by SEQ ID NO:55, complete amino acid sequence of the secretion type VH including a signal sequence deduced from the nucleotide sequence is represented by SEQ ID NO:56, complete nucleotide sequence of the VL contained in the plasmid KM3907Ka103 is represented by SEQ ID NO:57, and complete amino acid sequence of the secretion type VL including a signal sequence deduced from the nucleotide sequence is represented by SEQ ID NO:58. Based on an analysis similar to the above, it was found that the isolated each cDNA is a complete length cDNA encoding the antis CLDN4 monoclonal antibody KM3907 including a secretion signal sequence, and the sequence at positions 1 to 19 of the amino acid sequence represented by SEQ ID NO:56 is the secretion signal sequence regarding the H chain, and the sequence at positions 1 to 22 of the amino acid sequence represented by SEQ ID NO:58 is the secretion signal sequence regarding the L chain.

Next, novelty of the amino acid sequences of the VH and VL of anti-CLDN4 monoclonal antibodies KM3900 and KM3907 was examined. Using GCG Package (version 9.1, Genetics Computer Group) as the sequence analyzing system, amino acid sequence data base of known proteins was retrieved by the BLASTP method [*Nucleic Acids Res.*, 25, 3389 (1997)]. As a result, completely coinciding amino acid sequences were not found for both of the VH and VL, so that it was confirmed that the VH and VL of anti-CLDN4 monoclonal antibodies KM3900 and KM3907 have novel amino acid sequences.

Also, CDRs of the VH and VL of anti-CLDN4 monoclonal antibodies KM3900 and KM3907 were identified by comparing with conventionally known amino acid sequences of antibodies [*SEQUENCES of Proteins of Immunological Interest*, US Dept. Health and Human Services (1991)]. The amino acid sequences of the CDR1, CDR2 and CDR3 of the VH of anti-CLDN4 monoclonal antibody KM3900 are represented by SEQ ID NOs:19, 20 and 21, respectively, and the acid sequences of the CDR1, CDR2 and CDR3 of the VL are represented by SEQ ID NOs:22, 23 and 24, respectively.

In addition, the amino acid sequences of the CDR1, CDR2 and CDR3 of the VH of anti-CLDN4 monoclonal antibody KM3907 are represented by SEQ ID NOs:59, 60 and 61, respectively, and the acid sequences of the CDR1, CDR2 and CDR3 of the VL are represented by SEQ ID NOs:62, 63 and 64, respectively.

EXAMPLE 7

Preparation of Anti-CLDN4 Human Chimeric Antibodies (1) Construction of Vectors for Expression of Anti-CLDN4 Human Chimeric Antibody cKM3900_93 and cKM3907_93

A vector for expression of an anti-CLDN4 human chimeric antibody cKM3900_93 was constructed in the following manner using the vector for expression of humanized antibody pKANTEX93 described in WO 97/10354 and the plasmids KM3900_H202 and KM3900_K23 obtained in Example 6-(2).

PCR was carried out by preparing 50 μl of a reaction solution containing 100 ng of the plasmid KM3900_H202 as the template, 5 μl of 10×KOD buffer 1, 5 μl of 2 mmol/l dNTP, 2 μl of 25 mmol/l magnesium chloride, 1 μl of 10 μmol/l of each of the primers comprising the nucleotide sequences represented by SEQ ID NOs:49 and 50 and 1 μl of KOD polymerase (manufactured by TOYOBO). The PCR was carried out by, after denaturation treatment at 96° C. for 3 minutes, repeating 35 cycles, each cycle consisting of reaction at 94° C. for 1 minute at 94° C., reaction 58° C. for 1 minute and reaction at 72° C. for 1 minute, followed by reaction at 72° C. for 5 minutes. By this reaction, a gene fragment encoding the VH of KM3900 to which the restriction enzyme recognition sequence for inserting into pKANTEX93 was added was amplified. In die same manner, a reaction solution containing 100 ng of the plasmid KM3900_K23 as the template, 5 μl of 10 μmol/l buffer 1, 5 μl of 2 mmol/l dNTP, 2 μl of 25 mmol/l magnesium chloride, 1 μl of 10 μmol/l of each of the primers comprising the nucleotide sequences represented by SEQ ID NOs:51 and 52 and 1 μl of KOD polymerase (manufactured by TOYOBO) was prepared, and the PCR was carried out in the same manner as in the above, thereby amplifying a gene fragment encoding the VL of KM3900 to which the restriction enzyme recognition sequence for inserting into pKANTEX93 was added.

In the same manner, an anti-CLDN4 human chimeric antibody expression vector cKM3907_93 was constructed using the plasmids KM3907G2a101 and KM3907Ka103 obtained in Example 6-(2). Sequences of the primers for VH amplification use are represented by SEQ ID NOs:65 and 66, and sequences of the primers for VL amplification use in SEQ ID NOs:67 and 68.

Respective reaction products were separated by agarose gel electrophoresis, and the thus obtained amplified fragment of about 0.4 kbp was extracted using Gel Extraction Kit (manufactured by QIAGEN). The thus obtained gene fragment was ligated to a pBluescript II SK(−) vector digested with SmaI using Ligation high (manufactured by TOYOBO), and then transformants were prepared therefrom to obtain a plasmid VH5 containing a nucleotide sequence encoding the VH of KM3900 and a plasmid VL7 containing a nucleotide sequence encoding the VL of KM3900, in the same manner as in Example 1-(1).

After digesting the plasmid VH5 with restriction enzymes ApaI and NotI and digesting the plasmid VL7 with restriction enzymes EcoRI and BsiWI, respective reaction products were separated by agarose gel electrophoresis, and the thus obtained gene fragment of about 0.4 kbp was extracted using Gel Extraction Kit (manufactured by QIAGEN). After obtaining transformants in the same manner as described in the above, by ligating the fragment obtained by digesting the plasmid VH5 to the pKANTEX93 vector digested also with ApaI and NotI, pKANTEX93 vector into which the VH of KM3900 was inserted was obtained using a plasmid extraction kit (manufactured by QIAGEN). Next, the vector was digested with EcoRI and BsiWI and then ligated to a fragment obtained by digesting the above-described plasmid VL7, thereby obtaining transformants in the same manner as in Example 1-(1), and then an anti-CLDN4 human chimeric antibody expression vector cKM3900_93 into which the VH and VL of KM3900 were inserted was obtained using the plasmid extraction kit.

(2) Expression of Anti-CLDN4 Human Chimeric Antibody in an Animal Cell

Using the anti-CLDN4 human chimeric antibody cKM3900_93 obtained in the above-mentioned (1), expression of the anti-CLDN4 human chimeric antibody in an animal cell was carried out by a conventional method [*Antibody Engineering, A Practical Guide*, W.H. Freeman and Company (1992)] to obtain transformants into which the cKM3900_93 was transfected. Also, an anti-CLDN4 human chimeric antibody expression vector cKM3907_93 into which the VH and VL of KM3907 were inserted was obtained in the same manner.

(3) Preparation of Purified Antibodies

After culturing each of the transformants obtained in the above-mentioned (2) by a general culturing method, die cell suspensions were recovered and centrifuged for 15 minutes under conditions of 3,000 rpm at 4° C. to recover the culture supernatants, and then the culture supernatants were filtration-sterilized using a 0.22 μm pore size Millex GV filter (manufactured by Millipore). Anti-CLDN4 human chimeric antibodies cKM3900 and cKM3907 (hereinafter referred to as "cKM3900" and "cKM3907", respectively) were purified from the thus obtained culture supernatants using Protein A High-capacity Resin (manufactured by Millipore) and in accordance with the instructions attached thereto.

Purity and expressed molecular size of the thus obtained purified samples of cKM3900 and cKM3907 were confirmed by SDS-PACE using gradient gel (manufactured by ATTO, catalogue number: E-T520L) and in accordance with the instructions attached thereto.

Figure 14:
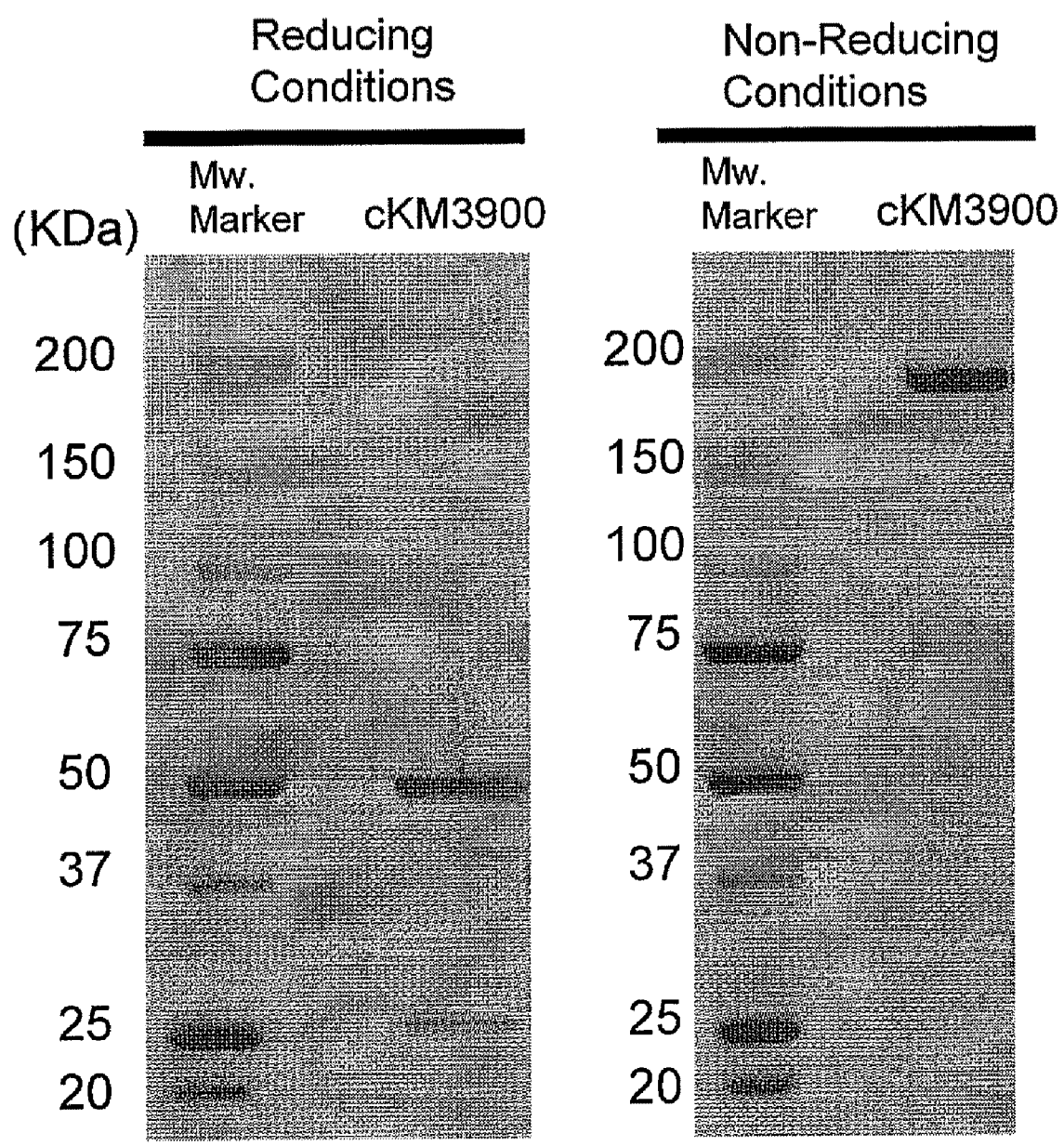
FIG. 14 shows results in which a purified anti-CLDN4 human chimeric antibody cKM3900 was subjected to SDS-PAGE under reducing conditions (β-mercaptoethanol added) and non-reducing conditions (β-mercaptoethanol non-added).
Figure 15:
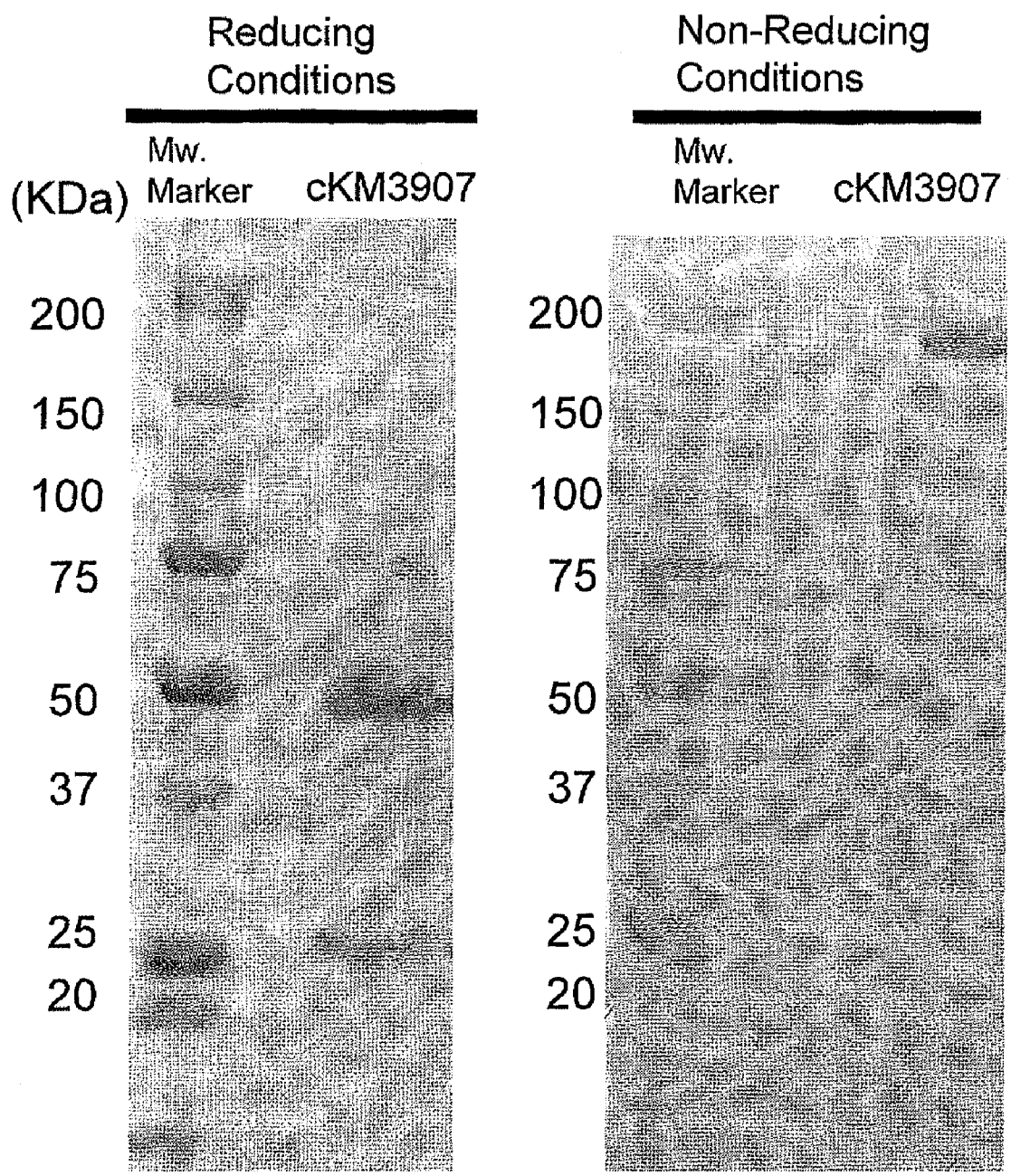
FIG. 15 shows results in which a purified anti-CLDN4 human chimeric antibody cKM3907 was subjected to SDS-PAGE under reducing conditions (β-mercaptoethanol added) and non-reducing conditions (β-mercaptoethanol non-added).

A result of cKM3900 is shown in FIG. 14, and a result of cKM3907 is shown in FIG. 15. From the electrophoresis pattern of the purified anti-CLDN4 human chimeric antibodies, one band was found at around 150 to 200 kilo Daltons (hereinafter referred to as "kDa") in molecular weight under non-reducing condition, and two bands of about 50 kDa and about 25 kDa under reducing condition. Such an electrophoresis pattern coincides with the result in which SDS-PAGE of IgG class antibodies was carried out under the same conditions [*Antibodies—A Laboratory Manual*, Cold Spring Harbor Laboratory, Chapter 14 (1988), *Monoclonal Antibodies—Principles and Practice*, Academic Press Limited (1996)]. Accordingly, it was confirmed that the anti-CLDN4 human chimeric antibodies cKM3900 and cKM3907 are expressed as the antibody molecules of normal structure.

EXAMPLE 8

Activity Evaluation of Anti-CLDN4 Human Chimeric Antibodies (1) Reactivity with Cancer Cell Lines by FCM Pancreatic cancer cell line Capan-2 which expresses CLDN4 was used as the evaluation cell of cKM3900, and a breast cancer cell line MCF7 which expresses both of CLDN3 and CLDN4 was used as the evaluation cell of cKM3907. The cells were cultured for 3 to 4 days and peeled off using 0.02% EDTA solution (manufactured by Nacalai Tesque) to recover the resulting cells. The thus recovered cells were washed with PBS and, in order to avoid nonspecific adsorption of antibodies, blocked using BSA-PBS at ice temperature for 30 minutes. The cells were dispensed at 1 to $5×10^5$ cells/100 μl BSA-PBS into a 96-well U bottom plate and centrifuged (1,500 rpm, 5 minutes), the supernatant was removed and then 5 μg/ml of a negative control antibody cKM3034 (anti-FGF8 human chimeric antibody) [US 2004/0091480], an anti-CLDN4 monoclonal antibody KM3900 or KM3907 or an anti-CLDN4 human chimeric antibody cKM3900 or cKM3907 was dispensed as the primary antibody at 100 µl/well and allowed to react at ice temperature for 60 minutes. After washing with BSA-PBS once, an FITC-labeled anti-mouse immunoglobulin G (H+L) (manufactured by DAKO) or FITC-labeled anti-human immunoglobulin U (H+L) (manufactured by Jackson Laboratories), diluted 50-fold with BSA-PBS, was added thereto as the secondary antibody at 100 µl/well and allowed to react at ice temperature for 30 minutes under shading. After washing again once with PBS and subsequently suspending in PBS, the fluorescent intensity was measured by FCM (manufactured by Beckman Coulter).

Reactivity of the negative control antibody cKM3034 (anti-FGF8 human chimeric antibody), anti-CLDN4 monoclonal antibody KM3900 and anti-CLDN4 human chimeric antibody cKM3900 is shown by a histogram in FIG. 16. It was found that the anti-CLDN4 human chimeric antibody KM3900 reacts with Capan-2 similar to the case of the anti-CLDN4 monoclonal antibody KM3900.

Figure 17:
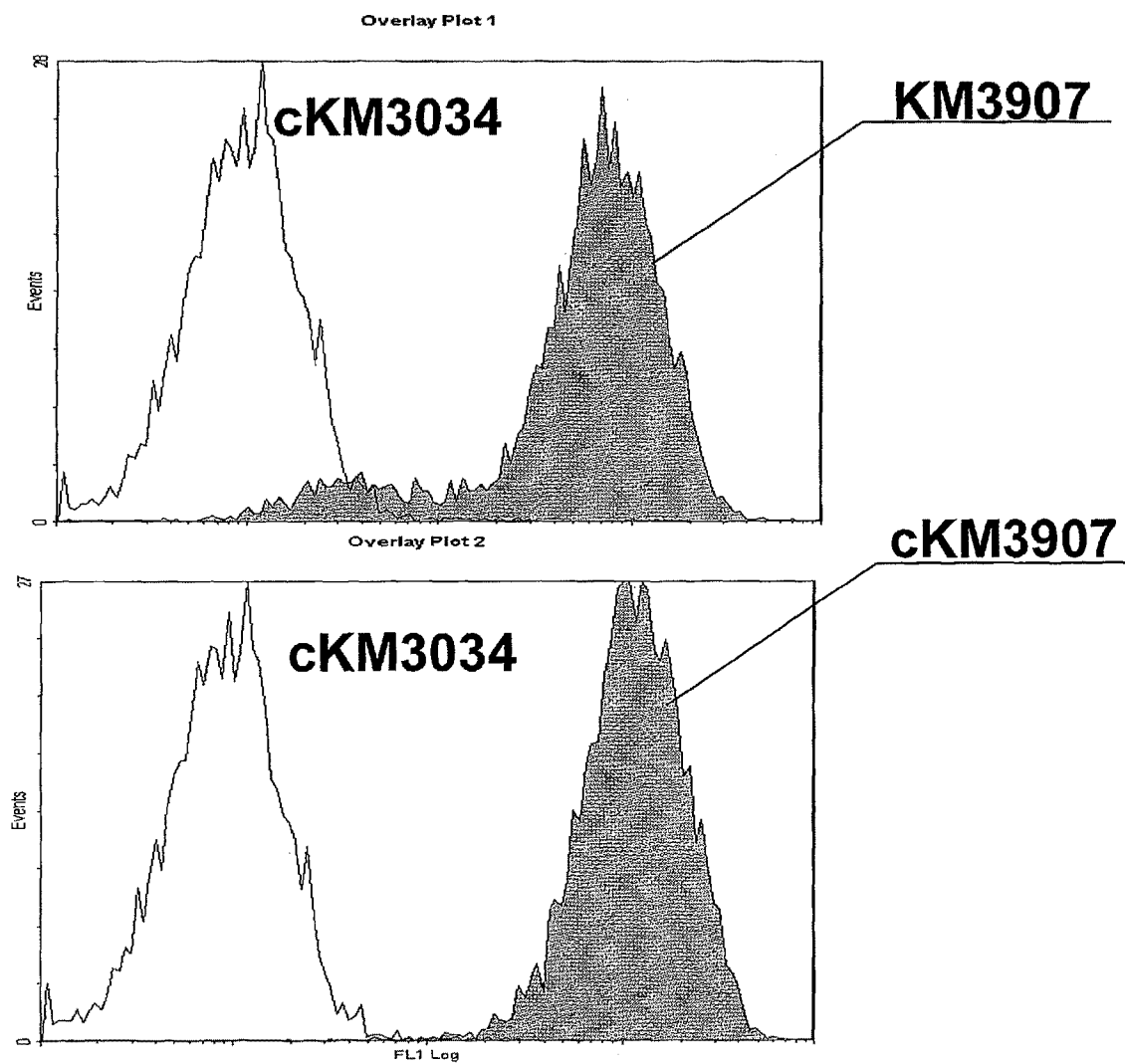
FIG. 17 shows results in which the reactivity of an anti-FGF-8 human chimeric antibody cKM3034 as a negative control antibody, an anti-CLDN4 human chimeric antibody cKM3900 and an anti-CLDN4 monoclonal antibody KM3900 for human breast cancer cell line MCF7 was measured by FCM. The ordinate shows the number of cells, and the abscissa shows fluorescence intensity.

Reactivity of the negative control antibody cKM3034 (anti-FGF8 human chimeric antibody), anti-CLDN4 monoclonal antibody KM3907 and anti-CLDN4 human chimeric antibody cKM3907 is shown by a histogram in FIG. 17. It was found that the anti-CLDN4 human chimeric antibody KM3907 reacts with MCF7 similar to the case of the anti-CLDN4 monoclonal antibody KM3907.

(2) ADCC Activity of Anti-CLDN4 Human Chimeric Antibodies

ADCC activity of the anti-CLDN4 human chimeric antibodies cKM3900 and cKM3907 obtained in Example 7 was measured in the following manner. As the target cells of cKM3900, the CLDN4-myc/His gene-introduced CHO cell clone (CLDN4/CHO), CLDN4-expressing human pancreatic cancer cell line Capan-2 used in (1) of this Example, human ovarian cancer cell line MCAS and human breast cancer cell line MCF7 were used. As the evaluation cells of cKM3907, CLDN4/CHO, CLDN3-myc/His gene-introduced CHO cell clone (CLDN3/CHO), human ovarian cancer cell line MCAS and the human breast cancer cell line MCF7 which expresses both CLDN4 and CLDN3 and was used in (1) of this Example were used. Polymorphprep (manufactured by NYCOMED) was used for the preparation of effector cell solution.

(2)-1 Preparation of Target Cell Solution

Capan-2 cultured using an RPMI 1640-FCS(10) medium [RPMI 1640 medium containing 10% FCS (manufactured by Invitrogen)] was washed by centrifugation and suspension using an RPMI 1640-FCS(1) medium [RPMI 1640 medium containing 1% FCS (manufactured by Invitrogen)] which is an ADCC activity measuring medium, and then the cell density was adjusted to $2 \times 10^5$ cells/ml using the ADCC activity measuring medium and used as the target cell solution.

(2)-2 Preparation of Effector Cell Solution

From a healthy person, 30 ml of venous blood was collected and gently mixed by adding heparin sodium (manufactured by Shimizu Pharmaceutical). A mononuclear cell (PBMC) fraction was separated from this using Polymorphprep (manufactured by NYCOMED) and in accordance with the instructions attached thereto. The thus separated PBMC fraction was washed twice by centrifugation with the ADCC activity measuring medium and then optionally suspended to be used as the effector cell solution.

(2)-3 Measurement of ADCC Activity

The target cell solution prepared in the above-mentioned (2)-1 was dispensed at 50 µl ($1 \times 10^4$ cells/well) into a 96-well U bottom plate (manufactured by Falcon). Next, 50 µl of the effector cell solution prepared in the above-mentioned (2)-2 (diluted such that the ratio of the effector cell and target cell becomes 25:1) was added thereto. Further, the anti-CLDN4 human chimeric antibody cKM3900 or cKM3907 was added thereto by diluting with the ADCC activity measuring medium to a respective final concentration of 0.001 to 10 µg/ml and, after adjusting die total volume to 150 µl, allowed to react at 37° C. for 4 hours. After the reaction, the plate was centrifuged, and lactate dehydrogenase (LDH) activity in the supernatant was measured by obtaining die absorbance data using LDH-Cytotoxic Test (manufactured by WAKO) and in accordance with the instructions attached thereto. Absorbance data of the target cell spontaneous release were obtained by carrying out the same operation described in the above by using the ADCC activity measuring medium instead of the effector cell solution and antibody solution, and absorbance data of the effector cell natural release by using the ADCC activity measuring medium instead of the target cell solution and antibody solution. Absorbance data of the target cell total release were obtained by carrying out the same operation described in the above, by using the ADCC activity measuring medium instead of the antibody solution and effector cell solution and carrying out the reaction by adding 20 µl of 9% Triton X-100 solution 45 minutes before completion of the reaction. The ADCC activity was calculated by the following formula.

(Formula)

ADCC activity (%)={(absorbance of sample−(absorbance of effector cell and target cell spontaneous release)}/(absorbance of target cell total release−absorbance of target cell spontaneous release)×100

A result of cKM3900 is shown in FIG. 18, and a result of cKM3907 in FIG. 19. It was found that the anti-CLDN4 human chimeric antibody cKMS3900 has ADCC activity antibody concentration-dependently upon the CLDN4-expressing cells. It was also found that the anti-CLDN4 human chimeric antibody cKM3907 has ADCC activity antibody concentration-dependently upon the CLDN4- and CLDN3- expressing cells.

(3) CDC Activity of Anti-CLDN4 Human Chimeric Antibodies

CDC activity of the anti-CLDN4 human chimeric antibodies cKM3900 and cKM3907 obtained in Example 7 was measured in the following manner. As the target cell of cKM3900, CLDN4/CHO was used. As the target cells of cKM3900, CLDN4/CHO, CLDN3/CHO and the human breast cancer cell line MCF7 which expresses both CLDN3 and CLDN4 were used.

(3)-1 Preparation of Target Cell Solution

Each of the cell lines was peeled off using 0.02% EDTA Solution (manufactured by Nacalai Tesque), washed with RPM 1640 medium (manufactured by Invitrogen) containing 1.4% BSA (manufactured by Invitrogen) and 50 µg/ml gentamicin (manufactured by Nacalai Tesque) and then suspended in the same medium to give a density of $2 \times 10^{-5}$ cells/ml and used as the target cell solution.

(3)-2 Preparation of Human Complement Solution

A human complement serum SERA, COMPLEMENT (manufactured by SIGMA, S1764) was dissolved in 1 ml of de-ionized water and diluted 2-fold by adding the same volume of a CDC measuring medium, and used as the human complement solution.

(3)-3 Measurement of CDC Activity

The complement solution prepared in the above-mentioned (3)-2 was dispensed at 50 µl into respective wells of a 96-well flat bottom plate (manufactured by SUMILON). Subsequently, 50 µl of the target cell solution prepared in the above-mentioned (3)-1 was added thereto and 50 µl of each antibody solution diluted with a medium for CDC use was flier added thereto and, after adjusting the total volume to 150 µl, allowed to react at 37° C. for 2 hours at 5% $CO_2$. A cell growth reagent WST-1 (manufactured by Roche) was added at 15 µl to respective wells, stirred using a plate mixer and allowed to react at 37° C. for 4 hours at 5% $CO_2$, and the absorbance at 415 nm was measured using Emax precision microplate reader (manufactured by WAKO). Using a well to which 50 µl of the complement solution and 100 µl of the medium for CDC were added, as the blank, and measuring absorbance of a well to which 50 µl of each of the target cell, complement solution and medium for CDC use was added (antibody non-addition), the CDC activity was calculated by the following formula.
(Formula)

CDC activity (%)={1−(antibody-added sample absorbance−blank absorbance)/(antibody non-added sample absorbance−blank absorbance)}×100

Figure 20:
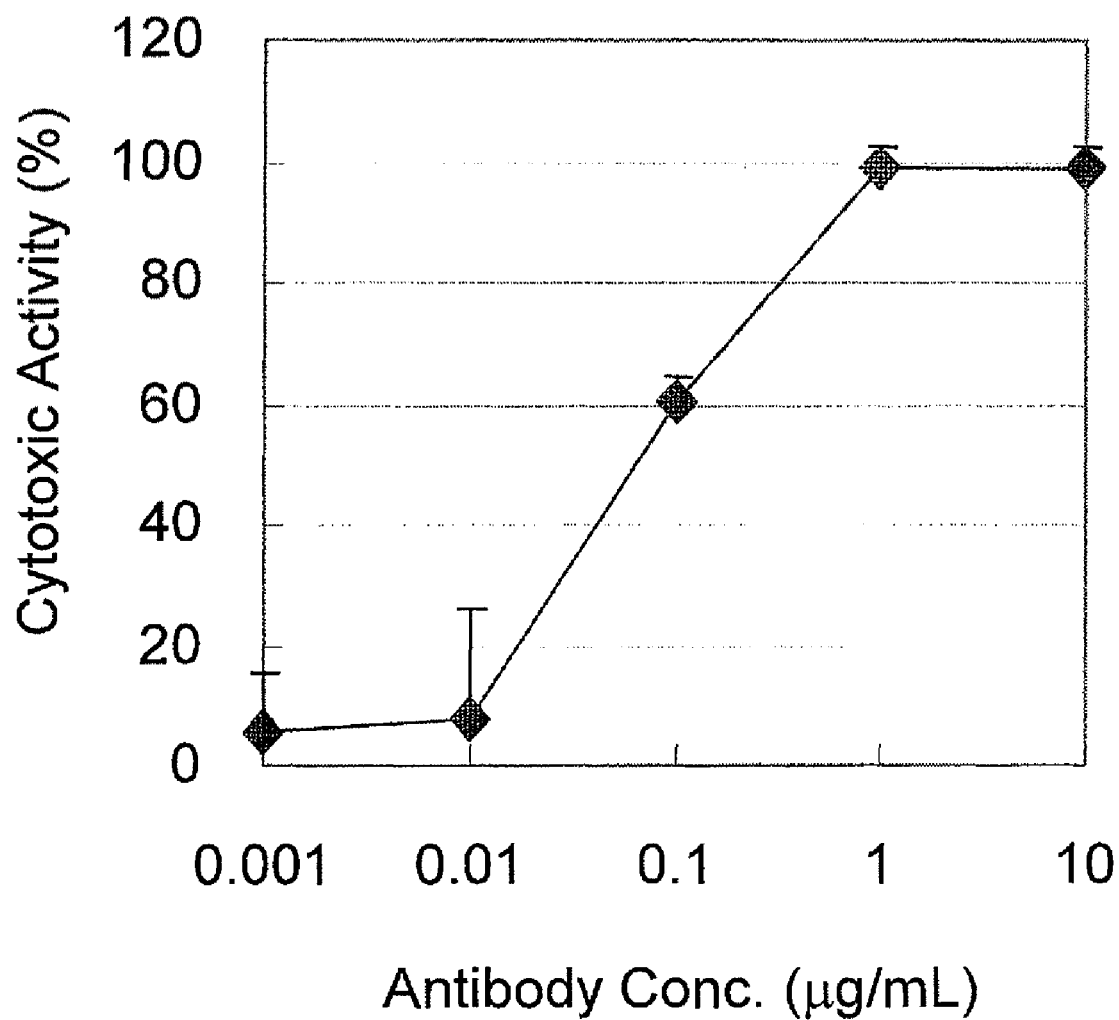
FIG. 20 shows results in which the CDC activity of an anti-CLDN4 human chimeric antibody cKM3900 for CLDN4-myc/His gene-introduced CHO cell (CLDN4/CHO) was measured. The ordinate shows CDC activity (%), and the abscissa shows the antibody concentration.

A result of the anti-CLDN4 human chimeric antibody cKM3900 is shown in FIG. 20, and a result of the anti-CLDN4 human chimeric antibody cKM3907 is shown in FIG. 21. It was found that the anti-CLDN4 human chimeric antibody cKM3900 has CDC activity antibody concentration-dependently upon the CLDN4-expressing cells. It was also found that the anti-CLDN4 human chimeric antibody cKM3907 has CDC activity antibody concentration-dependently upon the CLDN4- and CLDN3-expressing cells.

EXAMPLE 9

Cell Growth Inhibitory Activity of Anti-CLDN4 Monoclonal Antibodies Upon CLDN4-Expressing Cells In order to examine their cell growth inhibitory activity upon CLDN4-expressing cells, cell growth ability of the CLDN4-expressing CHO cell in the presence of the anti-CLDN4 monoclonal antibody KM3900 or KM3907 was examined.

CLDN4/CHO or vector/CHO was inoculated at $1 \times 10^3$ cells/100 µl/well into a 96-well plate and cultured for 24 hours, and then cultured for 96 hours by adding KM3900, KM3907 or a negative control antibody KMS511 to the medium to give a final concentration of 31.6 to 0.1 µg/ml. After the culturing, WST-1 reagent (manufactured by Roche Diagnostics) diluted to 50% with IMDM medium was added thereto at 20 µl/well and incubated at 37° C. for 2 hours, and then the absorbance at 450 nm (reference wavelength 650 nm) was measured using a microplate spectrophotometer. By regarding the value of a well to which the medium alone was added without adding the antibody (control) as 100%, relative growth rate (%) of the wells which were cultured for 96 hours by adding the antibody was calculated.

The results are shown in FIG. 22. As shown in FIG. 22, the anti-CLDN4 monoclonal antibody KM3900 did not inhibit cell growth of the vector/CHO, but inhibited cell growth of the CLDN4/CHO.

EXAMPLE 10

Evaluation of Drug Effect of Anti-CLDN4 Human Chimeric Antibody in Mouse Xenograft Model In order to evaluate in vivo drug effect of the anti-CLDN4 human chimeric antibody cKM3900, evaluation was carried out on the in vivo drug effect of the CLDN4-myc/His gene-introduced cell (CLDN4/CHO), a human pancreatic cancer cell line and a human ovarian cell line in a mouse xenograft early stage cancer model.

The CLDN4/CHO, human pancreatic cancer cell line Capan-2 (ATCC HTB-80) or human ovarian cell line MCAS (JCRB JCRB0240) was peeled off using 0.02% EDTA Solution (manufactured by Nacalai Tesque), washed with PBS, mixed with PRMI 1640 medium (manufactured by GIBCO-BRL) and then centrifuged at 300×g for 5 minutes, and the supernatant was discarded. After washing by a centrifugation by adding the same medium, the CLDN4/CHO and Capan-2 were adjusted to $5 \times 10^7$ cells/ml, and the MCAS to $1 \times 10^7$ cells/ml. Each cell suspension was subcutaneously transplanted at a dose of 100 µl under the right side of each of the SCID mice of 6 to 7 weeks old (manufactured by CLEA Japan). From the day of transplantation, the antibody solution diluted with PBS was administered through the caudal vein to die antibody administration group at a dose of 10 mg/kg, and the same volume of PBS alone was administered through the caudal vein to the control group (two animals per group). The administration was carried out twice a week, 6 times in all, and tumor diameter was measured using slide calipers starting at the time of finding the tumor. Tumor volume was calculated by the following formula.

Tumor volume $(mm^3)$=length×breadth$^2$×0.5

The results are shown in FIG. 23. As shown in FIG. 23, the anti-CLDN4 human chimeric antibody cKM3900 showed significant antitumor effect in the early stage cancer model caused by the transplantation of CLDN4/CHO, human pancreatic cancer cell line Capan-2 and human ovarian cancer cell line MCAS.

EXAMPLE 11

Preparation of Anti-CLDN4 Humanized Antibody (1) Design of Amino Acid Sequences of VH and VL of Anti-CLDN4 Humanized Antibody Firstly, amino acid sequence of VH of an anti-CLDN4 humanized antibody was designed in the following manner.

The amino acid sequence of FR of VH of a human antibody for grafting amino acid sequences of antibody VH of CDR1 to CDR3 represented by SEQ ID NOs:19 to 21, respectively, was selected. Kabat et al. have classified the VH of conventionally known various human antibodies into three subgroups (HSG I to III) based on the homology of their amino acid sequences and reported on the consensus sequences for each of the subgroups [*SEQUENCES of Proteins of Immunological Interest*, US Dept. Health and Human Services (1991)]. Since it is considered that these consensus sequences have a possibility of further reducing immunogenicity in human, it was decided to design the amino acid sequence of VH of an anti-CLDN4 humanized antibody based on these consensus sequences. In order to prepare an anti-CLDN4 humanized antibody having further high binding activity, an FR amino acid sequence having most high homology with the FR amino acid sequence of VH of anti-CLDN4 mouse antibody KM3900 which is a monoclonal antibody that binds to an extracellular region of a polypeptide encoded by the CLDN4 gene and has the neutralizing activity for CLDN4, among the FR amino acid sequences of the consensus sequences of the three subgroups of the VH of human antibodies, was selected in designing it.

As a result of retrieving the homology, the homologies with HSG I, HSG II and HSG III were 73.2%, 57.3% and 59.8%, respectively. Accordingly, the amino acid sequence of FR of the VH region of KM3900 had the highest homology with the subgroup I.

Based on the above result, the amino acid sequence of CDR of the VH of anti-CLDN4 mouse antibody KM3900 was grafted to an appropriate position of the FR amino acid sequence of the consensus sequence of subgroup I of human antibody VH. However, since (Glu at position 20, Ile at position 39, Lys at position 93 and Arg at position 103 in the amino acid sequence of VH of KM3900 represented by SEQ ID NO:16 are not the amino acid residues having highest using frequency in the region which corresponds to the amino acid sequence of human antibody FR cited by Kabat, but are amino acid residues which are used at a relatively high frequency, the above-mentioned amino acid residues which are recognized in the amino acid sequence of KM3900 were used. In this manner, an amino acid sequence HV0 of the VH of anti-CLDN4 humanized antibody represented by SEQ ID NO:74 was designed.

Next, amino acid sequence of VL of all anti-CLDN4 humanized antibody was designed in the following manner.

The amino acid sequence of FR of VL of a human antibody for grafting amino acid sequences of antibody VL of CDR1 to CDR3 represented by SEQ ID NOs:22 to 24, respectively, was selected. Kabat et al. have classified the VL of conventionally known various human antibodies into four subgroups (HSG I to TV) based on the homology of their amino acid sequences and further reported on the consensus sequences for each of the subgroups [*SEQUENCES of Proteins of Immunological Interest*, US Dept. Health and Human Services (1991)]. Thus, in the same manner as the case of VH, an FR amino acid sequence having most high homology with the FR amino acid sequence of VL of anti-CLDN4 mouse antibody KM3900 which is a monoclonal antibody that binds to an extracellular region of a polypeptide encoded by the CLDN4 gene and has the neutralizing activity for CLDN4, among the FR amino acid sequences of the consensus sequences of the four subgroups of the VL of human antibodies, was selected.

As a result of retrieving die homology, the homologies with HSG I, HSG II, HSG III and HSG IV were 72.5%, 62.5%, 68.8% and 71.3%, respectively. Accordingly, the amino acid sequence of FR of the VL of KM3900 had the highest homology with the subgroup I.

Based on the above result, the amino acid sequence of CDR of the VL of anti-CLDN4 mouse antibody KM3900 was grafted to an appropriate position of the FR amino acid sequence of the consensus sequence of subgroup I of human antibody VL. However, since Leu at position 26, Tyr at position 94 and Leu at position 127 in the amino acid sequence of VL of KM3900 represented by SEQ ID NO:18 are not the amino acid residues having highest using frequency in the region which corresponds to the amino acid sequence of human antibody FR cited by Kabat, but are amino acid residues which are used at a relatively high frequency, the above-mentioned amino acid residues which are recognized in the amino acid sequence of KM3900 were used. In this manner, an amino acid sequence HL0 of the VL of anti-CLDN4 humanized antibody represented by SEQ ID NO:76 was designed.

The amino acid sequence HV0 of VH and amino acid sequence HL0 of VL of anti-CLDN4 humanized antibody designed in the above are sequences in which the CDR amino acid sequence of the anti-CLDN4 mouse antibody KM3900 alone was grafted to the selected human antibody FR amino acid sequence, but in general, when a humanized antibody is prepared, its binding activity is frequently lowered in the case of merely a simple grafting of CDR amino acid sequence of a mouse antibody to a human antibody FR. In order to avoid lowering of the binding activity, modification of the amino acid residues considered to have influence upon the binding activity, among the FR amino acid residues which are different between human antibodies and mouse antibodies, is carried out together with the grafting of CDR amino acid sequence. Thus, the amino acid residues of FR considered to have influence upon the binding activity were identified in this Example in the following manner.

Firstly, three-dimensional structure of an antibody V region consisting of the amino acid sequence HV0 of VH and amino acid sequence HL0 of VL of anti-CLDN4 humanized antibody designed in the above (HV0LV0) was constructed using a computer modeling technique. Preparation of the three dimensional structure coordinates was carried out using a software AbM (manufactured by Oxford Molecular), and display of the three-dimensional structure using a software Pro-Explore (manufactured by Oxford Molecular) or ViewerLite (manufactured by Accelrys), in accordance with respective instructions attached thereto. In addition, a computer model of the three-dimensional structure of V region of the anti-CLDN4 mouse monoclonal antibody KM3900 was also constructed in the same manner. Further, by similarly constructing a three-dimensional structure model consisting of an amino acid sequence in which the amino acid residues in the FR amino acid sequences of VH and VL of HV0LV0, which are different from those of the anti-CLDN4 mouse antibody KM3900, were modified one by one into the amino acid residues that are found at positions corresponding to the anti-CLDN4 mouse antibody KM3900, three-dimensional structures of the V regions of anti-CLDN4 mouse antibody KM3900, HV0LV0 and modified product were compared.

As a result, as the amino acid residues among amino acid residues of FR of HV0LV0, which are considered to change three-dimensional structure of the antigen binding region and have influence upon the binding activity, Pro at position 41, Gln at position 43, Gly at position 44, Met at position 48, Arg at position 67, Val at position 68, Ile at position 70 and Ala at position 72 in the HV0 represented by SEQ ID NO:74, and Asp at position 1, Ser at position 10, Ile at position 21, Leu at position 48, Asp at position 71, Leu at position 79 and Pro at position 81 in the LV0 represented by SEQ ID NO:76 were selected. By modifying at least one or more of these selected amino acid residues into the amino acid residues which are present at the same positions of the amino acid sequence of the mouse antibody KM3900, VH and VL of humanized antibody having various modifications were designed. Specifically, regarding the antibody VH, at least one modification was introduced among the amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val in the amino acid sequence represented by SEQ ID NO:74. Also, regarding the VL, at least one modification was introduced among the amino acid modifications for substituting Asp at position 1 with Gln, Ser at position 10 with Ile, Ile at position 21 with Met, Leu at position 48 with Trp, Asp at position 71 with Ser, Leu at position 79 with Met and Pro at position 81 with Ala in the amino acid sequence represented by SEQ ID NO:76.

(2) Construction of cDNA Encoding VH of Anti-CLDN4 Humanized Antibody

A cDNA encoding the amino acid sequence HV0, designed in (1) of this Example, of VH of anti-CLDN4 humanized antibody was constructed using PCR in the following manner.

Firstly, the designed amino acid sequence was ligated with the anti-PERP mouse antibody KM3411 H chain secretion signal sequence described as the sequence at position 1 to 18 of the SEQ ID NO:12 described in WO 2005/121338A1, thereby preparing a complete antibody amino acid sequence. Next, the amino acid sequence was concerted into genetic codons. When two or more genetic codons are present for one amino acid residue, the corresponding genetic codon was determined by taking the codon usage found in the nucleotide sequences of antibody genes [*SEQUENCES of Proteins of Immunological Interest*, US Dept. Health and Human Services (1991)] into consideration (SEQ ID NO:73). The nucleotide sequence of cDNA encoding the amino acid sequence of complete antibody V region was designed by ligating the thus determined genetic codons, and binding nucleotide sequences of primers for amplification use at the time of PCR (including restriction enzyme recognition sequences for cloning into a vector for humanized antibody expression) were further added to the 5'-terminal and 3'-terminal. The thus designed nucleotide sequence was divided into a total of 4 nucleotide sequences, each consisting of about 100 nucleotides, starting from the 5'-terminal side (adjoining nucleotide sequences are allowed to have an overlapping sequence of about 20 bases on their termini), and synthetic oligonucleotides were synthesized from them in alternating orders of sense chain and antisense chain (SEQ ID NOs:77 to 80).

Each of the oligonucleotides (SEQ ID NOs:77 to 80) was added to 50 µl of a reaction solution to give a final concentration of 0.1 µmol/l, and PCR was carried out using 0.5 µmol/l T3 primer (manufactured by Takara Shuzo), 0.5 µmol/l T7 primer (manufactured by Takara Shuzo) and 1 unit of KOD polymerase (manufactured by TOYOBO) and in accordance with the instructions attached thereto. The conditions described in the instructions (30 cycles, each cycle consisting of reaction at 94° C. for 30 seconds, reaction at 50° C. for 30 seconds and reaction at 74° C. for 60 seconds) were used as the reaction conditions of this case. After subjecting the reaction solution to ethanol precipitation, the residue was dissolved in sterilized water, subjected to an appropriate restriction enzyme treatment and then ligated to a plasmid pBluescript II SK(−) (manufactured by Stratagene). *Escherichia coli* DH5α was transformed using the recombinant plasmid DNA solution obtained in this manner, plasmid DNA samples were prepared from the transformants and their nucleotide sequences were analyzed using BigDye Terminator Cyclesequencing FS Ready Reaction Kit (manufactured by Applied Biosystems), and a plasmid pBS/HV0 having the nucleotide sequence of interest was obtained as a result.

Next, modification of the amino acid residues of FR designed in (1) of this Example was carried out by preparing synthetic oligonucleotides having mutation and carrying out the above-mentioned PCR, or by carrying out PCR using the plasmid DNA comprising a cDNA encoding HV0, prepared in the above, as the template and using synthetic DNA samples having mutation as the primers, and by isolating amplified gene fragments. Regarding the genetic codons of the amino acid residues after modification, the genetic codons found in the anti-CLDN4 mouse antibody KM3900 were employed. In addition, unless otherwise noted, these were allowed to react hereinafter by PCR of 35 cycles, each cycle consisting of reaction at 94° C. for 30 seconds, reaction at 55° C. for 30 seconds and reaction at 72° C. for 60 seconds. The PCR was carried out using KOD-plus polymerase (manufactured by TOYOBO). Also, the synthetic oligonucleotides used herein were purchased from FASMAC.

(3) Construction of cDNA Encoding VL of Anti-CLDN4 Humanized Antibody

A cDNA encoding the amino acid sequence of VL of anti-CLDN4 humanized antibody, designed in (1) of this Example, was constructed using PCR in the following manner.

Firstly, the designed amino acid sequence was ligated with the anti-PERP mouse antibody KM3411 L chain secretion signal sequence described as the sequence at positions 1 to 22 of the SEQ ID NO:14 described in WO 2005/121338A1, thereby preparing a complete antibody amino acid sequence. Next, the amino acid sequence was concerted into genetic codons. When two or more genetic codons are present for one amino acid residue, the corresponding genetic codon was determined by taking the codon usage found in the nucleotide sequences of antibody genes [*SEQUENCES of Proteins of Immunological Interest*, US Dept. Health and Human Services (1991)] into consideration (SEQ ID NO:75). The nucleotide sequence of cDNA encoding the amino acid sequence of complete antibody V region was designed by ligating the thus determined genetic codons, and binding nucleotide sequences of primers for amplification use at the time of PCR (including restriction enzyme recognition sequences for cloning into a vector for humanized antibody expression) were further added to the 5'-terminal and 3'-terminal. The thus designed nucleotide sequence was divided into a total of 4 nucleotide sequences, each consisting of about 100 nucleotides, starting from die 5'-terminal side (adjoining nucleotide sequences are allowed to have an overlapping sequence of about 20 bases on their termini), and synthetic oligonucleotides were synthesized from them in alternating orders of sense chain and antisense chain (SEQ ID NOs:81 to 84).

Each of the oligonucleotides (SEQ ID NOs:81 to 84) was added to 50 µl of a reaction solution to give a final concentration of 0.1 µmol/l, and PCR was carried out in the same manner as in the above-mentioned (2) using 0.5 µmol/l T7 primer (manufactured by Takara Shuzo), 0.5 µmol/l T3 primer (manufactured by Takara Shuzo) and 1 unit of KOD polymerase (manufactured by TOYOBO) and in accordance with the instructions attached to the KOD polymerase. After subjecting the reaction solution to ethanol precipitation, the residue was dissolved in sterilized water, subjected to an appropriate restriction enzyme treatment and then ligated to a plasmid pBluescript II SK(−) (manufactured by Stratagene). *Escherichia coli* DH45α was transformed using the recombinant plasmid DNA solution obtained in this manner, plasmid DNA samples were prepared from the transformants and their nucleotide sequences were analyzed using BigDye Terminator Cyclesequencing FS Ready Reaction Kit (manufactured by Applied Biosystems), and a plasmid pBS/LV0 having the nucleotide sequence of interest was obtained as a result.

Next, modification of the amino acid residues of FR designed in (1) of this Example was carried out by preparing synthetic oligonucleotides having mutation and carrying out the above-mentioned PCR, or by carrying out PCR using the plasmid DNA comprising a cDNA encoding LV0, prepared in the above, as the template and using synthetic DNA samples having mutation as the primers, and by isolating amplified gene fragments. Regarding the genetic codons of the amino acid residues after modification, the genetic codons found in the anti-CLDN4 mouse antibody KM3900 were employed.

In addition, unless otherwise noted, these were allowed to react hereinafter by PCR of 35 cycles, each cycle consisting of reaction at 94° C. for 30 seconds, reaction at 55° C. for 30 seconds and reaction at 72° C. for 60 seconds. The PCR was carried out using KOD-plus polymerase (manufactured by TOYOBO). Also, the synthetic oligonucleotides used herein were purchased from FASMAC.
(4) Construction of Vector for Expression of Anti-CLDN4 Humanized Antibody Various vectors for expression of anti-CLDN4 humanized antibody were constructed by inserting respective cDNA preparations encoding the HV0 and LV0 obtained in (2) and (3) of this Example, or cDNA preparations encoding their modified products, into appropriate sites of the vector for expression of humanized antibody pKANTEX93 described in WO 97/10354.
(5) Stable Expression of Anti-CLDN4 Humanized Antibody Using an Animal Cell and Preparation of Purified Antibody Stable expression of anti-CLDN4 humanized antibody using an animal cell and purification of the antibody from a culture supernatant were carried out in the same manner as the methods described in Example 7.

EXAMPLE 12

Identification of Anti-CLDN4 Monoclonal Antibody Recognizing Epitopes

In order to analyze epitopes of anti-CLDN4 monoclonal antibodies, cells which express a fusion protein of CLDN4 and CLDN6 prepared by substituting the amino acid sequence of the extracellular region of CLDN6 with two extracellular regions of CLDN4 (hereinafter referred to as "EL-1" and "EL-2", respectively) were prepared. By examining the reactivity of anti-CLDN4 monoclonal antibodies KM3900 and KM3907 for these cells expressing the fusion protein of CLDN4 and CLDN6, identification of epitopes of the antibodies was carried out.
(1) Construction of CLDN4-CLDN6 Fusion Protein-Expressing CHO Cell Clone Each of the genes encoding CLDN4-myc/His and CLDN6-myc/His prepared in Example 1-(1) and Example 1-(2) was digested with restriction enzymes EcoRI, KpnI and PstI. After the separation/recovering of an EcoRI-PstI fragment (about 250 bp) and a PstI-KpnI fragment (about 500 bp) by agarose gel electrophoresis, the CLDN4-myc/His-derived EcoRI-PstI fragment and CLDN6-myc/His-derived PstI-KpnI fragment were ligated using Ligation high (manufactured by TOYOBO) and inserted into the EcoRI-KpnI site of pBluescript II SK(-) vector. As a result, a gene encoding a fusion protein in which its N-terminal side extracellular region (hereinafter referred to as "EL1") has the amino acid sequence of CLDN4, its C-terminal side extracellular region (hereinafter referred to as "EL2") has the amino acid sequence of CLDN6 and myc/His is added to the C-terminal side (hereinafter referred to as "4-EL1/6-EL2") was prepared. The nucleotide sequence and the amino acid sequence of the 4-EL1/6-EL2 are represented by SEQ ID NO:69 and SEQ ID NO:70, respectively.

By the same method, a gene encoding a fusion protein in which its EL1 has the amino acid sequence of CLDN6, its EL2 has the amino acid sequence of CLDN4 and myc/His is added to the C-terminal side (hereinafter referred to as "6-EL1/4-EL2") was prepared. The nucleotide sequence and the amino acid sequence of the 6-EL1/4EL2 are represented by SEQ ID NO:71 and SEQ ID NO:72, respectively.

By the same method of Example 1-(1), an expression vector was prepared by inserting 4-EL1/6-EL2 and 6-EL1/4-EL2 into pKANTEX93 vector and introduced into a CHO/DG44 cell [*Somatic Cell and Molecular Genetics*, 12, 555 (1986)] by electroporation [*Cytotechnology*, 3, 133 (1990)], and then a drug selection was carried out to obtain a 4-EL1/6-EL2 gene-introduced CHO cell clone (hereinafter referred to as "4-EL1/6-EL2/CHO") and a 6-EL1/4-EL2 gene-introduced CHO cell clone (hereinafter referred to as "6-EL1/4-EL2/CHO").
(2) Reactivity of Anti-CLDN4 Monoclonal Antibodies KM3900 and KM3907 for 4-EL1/6-EL2 and 6-EL1/4-EL2 Expression Cells By the same method of Example 3-(3), the reactivity of anti-CLDN4 monoclonal antibodies KM3900 and KM3907 for 4-EL1/6-EL2/CHO and 6-EL1/4-EL2/CHO was examined by FCM. The reactivity for each cell is shown in the following Table 2.

TABLE 2

| Reactivity of anti-CLDN4 monoclonal antibody | | |
|---|---|---|
| | CHO expression cell | |
| Antibody | 4-EL1/6-EL2 | 6-EL1/4-EL2 |
| KM3900 | − | + |
| KM3907 | + | − |

As shown in Table 2, the anti-CLDN4 monoclonal antibody KM3900 reacted with 6-EL1/4-EL2/CHO but did not react with 4-EL1/6-EL2/CHO. The anti-CLDN4 monoclonal antibody KM3907 reacted with 4-EL1/6-EL2/CHO but did not react with 6-EL1/4-EL2/CHO.

Based on the above results, it was found that the anti-CLDN4 monoclonal antibody KM3900 recognizes a three-dimensional structure consisting of the amino acid sequence at position 141 to 159 of CLDN4 and binds thereto, and the anti-CLDN4 monoclonal antibody KM3907 recognizes a three-dimensional structure consisting of the amino acid sequence at positions 28 to 76 of CLDN4 and binds thereto.

While the invention has been described in detail and with reference to specific embodiments thereof, it will be apparent to one skill in the art that various changes and modifications can be made therein without departing from the spirit and scope thereof.

This application is based on Japanese patent application Nos. 2007-068064 and 2007-223803 filed Mar. 16, 2007 and Aug. 30, 2007, respectively, and U.S. patent application Nos. 60/946,518 and 60/969,269 filed Jun. 27, 2007 and Aug. 31, 2007, respectively, the entire contents of which are incorporated hereinto by reference. All references cited herein are incorporated in their entirety.

What is claimed is:

1. An isolated monoclonal antibody or an antibody fragment thereof, which competes with a monoclonal antibody produced by the hybridoma KM3900 (FERM BP-10751) in the binding to the extracellular region of Claudin-4 (CLDN4), and
   (a) which specifically recognizes a three-dimensional structure of an extracellular region of a polypeptide encoded by the gene and binds to the extracellular region, or
   (b) which specifically binds to an extracellular region of a polypeptide encoded by a CLDN4 gene and has neutralizing activity for CLDN4,
wherein said antibody produced by the hybridoma KM3900 binds to residues 141 to 159 of CLDN4.

2. The isolated monoclonal antibody or the antibody fragment thereof according to claim 1, which binds to an epitope in the extracellular region of CLDN4 to which the hybridoma KM3900 (FERM BP-10751)-produced antibody binds.

3. The isolated antibody or the antibody fragment thereof according to claim 1, which is a monoclonal antibody produced by the hybridoma KM3900(FERM BP-10751).

4. The isolated antibody or the antibody fragment thereof according to claim 1, which is a recombinant antibody.

5. The isolated monoclonal antibody or the antibody fragment thereof according to claim 4, wherein the recombinant antibody is selected from a human chimeric antibody, a humanized antibody and a human antibody.

6. The isolated monoclonal antibody or the antibody fragment thereof according to claim 5, wherein CDR1, CDR2 and CDR3 of VH of the recombinant antibody comprise the amino acid sequences represented by SEQ ID NOs: 19, 20 and 21, respectively, and CDR1, CDR2 and CDR3 of VL of the recombinant antibody comprise the amino acid sequences represented by SEQ ID NOs: 22, 23 and 24, respectively.

7. The isolated monoclonal antibody or the antibody fragment thereof according to claim 5, which is a human chimeric antibody.

8. The isolated monoclonal antibody or the antibody fragment thereof according to claim 7, wherein VH of the human chimeric antibody comprises the amino acid sequence at positions 20 to 142 in the amino acid sequence represented by SEQ ID NO: 16, and VL of the human chimeric antibody comprises the amino acid sequence at positions 23 to 130 in the amino acid sequence represented by SEQ ID NO: 18.

9. The isolated monoclonal antibody or the antibody fragment thereof according to claim 5,
   wherein VH of the humanized antibody comprises the amino acid sequence represented by SEQ ID NO:74 or the amino acid sequence in which at least one modification among amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val is introduced in the amino acid sequence represented by SEQ ID NO:74, and
   VL of the humanized antibody comprises the amino acid sequence represented by SEQ ID NO:76 or the amino acid sequence in which at least one modification among amino acid modifications for substituting Asp at position 1 with Gln, Ser at position 10 with Ile, Ile at position 21 with Met, Leu at position 48 with Trp, Asp at position 71 with Ser, Leu at position 79 with Met and Pro at position 81 with Ala is introduced in the amino acid sequence represented by SEQ ID NO:76.

10. The isolated monoclonal antibody or the antibody fragment thereof according to claim 5,
- wherein VH of the humanized antibody comprises the amino acid sequence in which at least one modification among amino acid modifications for substituting Pro at position 41 with His, Gln at position 43 with Lys, Gly at position 44 with Ser, Met at position 48 with Ile, Arg at position 67 with Lys, Val at position 68 with Ala, Ile at position 70 with Leu and Ala at position 72 with Val is introduced in the amino acid sequence represented by SEQ ID NO:74, and
- VL of the humanized antibody comprises the amino acid sequence in which at least one modification among amino acid modifications for substituting Asp at position 1 with Gln, Ser at position 10 with Ile, Ile at position 21 with Met, Leu at position 48 with Trp, Asp at position 71 with Ser, Leu at position 79 with Met and Pro at position 81 with Ala is introduced in the amino acid sequence represented by SEQ ID NO:76.

11. An isolated monoclonal antibody or an antibody fragment thereof, which competes with a monoclonal antibody produced by the hybridoma KM3907 (FERM BP-10885) in the binding to the extracellular region of CLDN4, and
- (a) which specifically recognizes three-dimensional structure of an extracellular region of a polypeptide encoded by CLDN4 gene and binds to the extracellular region, or
- (b) which specifically binds to an extracellular region of a polypeptide encoded by a CLDN4 gene and has neutralizing activity for CLDN4,
- wherein said antibody produced by the hybridoma KM3907 binds to residues 28 to 76 of CLDN4.

12. The isolated monoclonal antibody or the antibody fragment thereof according to claim 11, which binds to an epitope in the extracellular region of CLDN4 to which the hybridoma KM3907 (FERM BP-10885)-produced monoclonal antibody binds.

13. The isolated antibody or the antibody fragment thereof according to claim 12, wherein the isolated monoclonal antibody is a monoclonal antibody produced by the hybridoma KM3907 (FERM BP-10885).

14. The isolated monoclonal antibody fragment according to claim 1, wherein the isolated antibody fragment is an antibody fragment selected from Fab, Fab', F(ab')$_2$, a single chain antibody (scFv), dimerized V region (diabody), disulfide stabilized V region (dsFv) and a peptide comprising CDRs.

15. A hybridoma which produces the monoclonal antibody described in claim 1, or 14.

16. The hybridoma according to claim 15, wherein the hybridoma is a hybridoma KM3900 (FERM BP-10751).

17. The hybridoma according to claim 15, wherein the hybridoma is a hybridoma KM3907 (FERM BP-10885).

18. A process for producing the antibody or the antibody fragment thereof of claim 1 or 11 comprising culturing the hybridoma of claim 15 and recovering the antibody or the antibody fragment thereof from the culture.

19. A method for immunologically detecting or measuring a polypeptide encoded by a CLDN4 gene, which comprises reacting the antibody or the antibody fragment thereof described in claim 1 with a sample.

* * * * *

SEQUENCE LISTING

<160> NUMBER OF SEQ ID NOS: 84

<210> SEQ ID NO 1
<211> LENGTH: 1846
<212> TYPE: DNA

<213> ORGANISM: Homo sapiens
<220> FEATURE:
<221> NAME/KEY: CDS
<222> LOCATION: (340)..(969)

<400> SEQUENCE: 1

| | | | | | |
|---|---|---|---|---|---|
| aaaagtgcct | tgttggcct | gggctcagga | atccagagaa | actggtcagg | aggaggcccc | 60 |
| agtgacaaaa | acccctccct | ctgccccgc | ccctctgcca | gagccatata | actgctcaac | 120 |
| ctgtccccga | gagagagtgc | cctggcagct | gtcggctgga | aggaactggt | ctgctcacac | 180 |
| ttgctggctt | gcgcatcagg | actggcttta | tctcctgact | cacggtgcaa | aggtgcactc | 240 |
| tgcgaacgtt | aagtccgtcc | ccagcgcttg | gaatcctacg | gcccccacag | ccggatcccc | 300 |
| tcagccttcc | aggtcctcaa | ctcccgtgga | cgctgaacaa | tggcctccat | ggggctacag | 360 |
| gtaatgggca | tcgcgctggc | cgtcctgggc | tggctggccg | tcatgctgtg | ctgcgcgctg | 420 |
| cccatgtggc | gcgtgacggc | cttcatcggc | agcaacattg | tcacctcgca | gaccatctgg | 480 |
| gagggcctat | ggatgaactg | cgtggtgcag | agcaccggcc | agatgcagtg | caaggtgtac | 540 |
| gactcgctgc | tggcactgcc | gcaggacctg | caggcggccc | gcgccctcgt | catcatcagc | 600 |
| atcatcgtgg | ctgctctggg | cgtgctgctg | tccgtggtgg | ggggcaagtg | taccaactgc | 660 |
| ctggaggatg | aaagcgccaa | ggccaagacc | atgatcgtgg | cgggcgtggt | gttcctgttg | 720 |
| gccggcctta | tggtgatagt | gccggtgtcc | tggacgcccc | acaacatcat | ccaagacttc | 780 |
| tacaatccgc | tggtggcctc | cgggcagaag | cgggagatgg | gtgcctcgct | ctacgtcggc | 840 |
| tgggccgcct | ccggcctgct | gctccttggc | gggggggctgc | tttgctgcaa | ctgtccaccc | 900 |
| cgcacagaca | agccttactc | cgccaagtat | tctgctgccc | gctctgctgc | tgccagcaac | 960 |
| tacgtgtaag | gtgccacggc | tccactctgt | tcctctctgc | tttgttcttc | cctggactga | 1020 |
| gctcagcgca | ggctgtgacc | ccaggagggc | cctgccacgg | gccactggct | gctggggact | 1080 |
| ggggactggg | cagagactga | gccaggcagg | aaggcagcag | ccttcagcct | ctctggccca | 1140 |
| ctcggacaac | ttcccaaggc | cgcctcctgc | tagcaagaac | agagtccacc | tcctctgga | 1200 |
| tattggggag | ggacggaagt | gacagggtgt | ggtggtggag | tggggagctg | gcttctgctg | 1260 |
| gccaggatag | cttaaccctg | actttgggat | ctgcctgcat | cggcgttggc | cactgtcccc | 1320 |
| atttacattt | tccccactct | gtctgcctgc | atctcctctg | ttccgggtag | gccttgatat | 1380 |
| cacctctggg | actgtgcctt | gctcaccgaa | acccgcgccc | aggagtatgg | ctgaggcctt | 1440 |
| gcccacccac | ctgcctggga | agtgcagagt | ggatggacgg | gtttagaggg | gaggggcgaa | 1500 |
| ggtgctgtaa | acaggtttgg | gcagtggtgg | gggaggggc | cagagaggcg | gctcaggttg | 1560 |
| cccagctctg | tggcctcagg | actctctgcc | tcacccgctt | cagccagggg | cccctggaga | 1620 |
| ctgatcccct | ctgagtcctc | tgccccttcc | aaggacacta | atgagcctgg | gagggtggca | 1680 |
| gggaggaggg | gacagcttca | cccttggaag | tcctgggggtt | tttcctcttc | cttctttgtg | 1740 |
| gtttctgttt | tgtaatttaa | gaagagctat | tcatcactgt | aattattatt | attttctaca | 1800 |
| ataaatggga | cctgtgcaca | ggaaaaaaaa | aaaaaaaaaa | aaaaaa | | 1846 |

<210> SEQ ID NO 2
<211> LENGTH: 209
<212> TYPE: PRT
<213> ORGANISM: Homo sapiens

<400> SEQUENCE: 2

```
Met Ala Ser Met Gly Leu Gln Val Met Gly Ile Ala Leu Ala Val Leu
 1               5                  10                  15
```

```
Gly Trp Leu Ala Val Met Leu Cys Cys Ala Leu Pro Met Trp Arg Val
             20                  25                  30
Thr Ala Phe Ile Gly Ser Asn Ile Val Thr Ser Gln Thr Ile Trp Glu
         35                  40                  45
Gly Leu Trp Met Asn Cys Val Val Gln Ser Thr Gly Gln Met Gln Cys
     50                  55                  60
Lys Val Tyr Asp Ser Leu Leu Ala Leu Pro Gln Asp Leu Gln Ala Ala
 65                  70                  75                  80
Arg Ala Leu Val Ile Ile Ser Ile Ile Val Ala Ala Leu Gly Val Leu
                 85                  90                  95
Leu Ser Val Val Gly Gly Lys Cys Thr Asn Cys Leu Glu Asp Glu Ser
            100                 105                 110
Ala Lys Ala Lys Thr Met Ile Val Ala Gly Val Val Phe Leu Leu Ala
        115                 120                 125
Gly Leu Met Val Ile Val Pro Val Ser Trp Thr Ala His Asn Ile Ile
    130                 135                 140
Gln Asp Phe Tyr Asn Pro Leu Val Ala Ser Gly Gln Lys Arg Glu Met
145                 150                 155                 160
Gly Ala Ser Leu Tyr Val Gly Trp Ala Ala Ser Gly Leu Leu Leu Leu
                165                 170                 175
Gly Gly Gly Leu Leu Cys Cys Asn Cys Pro Pro Arg Thr Asp Lys Pro
            180                 185                 190
Tyr Ser Ala Lys Tyr Ser Ala Ala Arg Ser Ala Ala Ala Ser Asn Tyr
        195                 200                 205
Val

<210> SEQ ID NO 3
<211> LENGTH: 693
<212> TYPE: DNA
<213> ORGANISM: Artificial sequence
<220> FEATURE:
<221> NAME/KEY: CDS
<222> LOCATION: (1)..(693)
<223> OTHER INFORMATION: Synthetic construct  CLDN4-myc/His sequence

<400> SEQUENCE: 3
atggcctcca tggggctaca ggtaatgggc atcgcgctgg ccgtcctggg ctggctggcc      60
gtcatgctgt gctgcgcgct gcccatgtgg cgcgtgacgg ccttcatcgg cagcaacatt     120
gtcacctcgc agaccatctg ggagggccta tggatgaact gcgtggtgca gagcaccggc     180
cagatgcagt gcaaggtgta cgactcgctg ctggcactgc cgcaggacct gcaggcggcc     240
cgcgccctcg tcatcatcag catcatcgtg gctgctctgg gcgtgctgct gtccgtggtg     300
gggggcaagt gtaccaactg cctggaggat gaaagcgcca aggccaagac catgatcgtg     360
gcgggcgtgg tgttcctgtt ggccggcctt atggtgatag tgccggtgtc ctggacggcc     420
cacaacatca tccaagactt ctacaatccg ctggtggcct ccgggcagaa gcgggagatg     480
ggtgcctcgc tctacgtcgg ctgggccgcc tccggcctgc tgctccttgg cggggggctg     540
ctttgctgca actgtccacc ccgcacagac aagccttact ccgccaagta ttctgctgcc     600
cgctctgctg ctgccagcaa ctacgtggaa caaaaactca tctcagaaga ggatctgaat     660
atgcataccg gtcatcatca ccatcaccat tga                                 693

<210> SEQ ID NO 4
<211> LENGTH: 230
<212> TYPE: PRT
<213> ORGANISM: Artificial sequence
<220> FEATURE:
```

<223> OTHER INFORMATION: Synthetic construct CLDN4-myc/His sequence

<400> SEQUENCE: 4

```
Met Ala Ser Met Gly Leu Gln Val Met Gly Ile Ala Leu Ala Val Leu
 1               5                  10                  15
Gly Trp Leu Ala Val Met Leu Cys Cys Ala Leu Pro Met Trp Arg Val
             20                  25                  30
Thr Ala Phe Ile Gly Ser Asn Ile Val Thr Ser Gln Thr Ile Trp Glu
         35                  40                  45
Gly Leu Trp Met Asn Cys Val Val Gln Ser Thr Gly Gln Met Gln Cys
     50                  55                  60
Lys Val Tyr Asp Ser Leu Leu Ala Leu Pro Gln Asp Leu Gln Ala Ala
 65                  70                  75                  80
Arg Ala Leu Val Ile Ile Ser Ile Ile Val Ala Ala Leu Gly Val Leu
                 85                  90                  95
Leu Ser Val Val Gly Gly Lys Cys Thr Asn Cys Leu Glu Asp Glu Ser
            100                 105                 110
Ala Lys Ala Lys Thr Met Ile Val Ala Gly Val Val Phe Leu Leu Ala
        115                 120                 125
Gly Leu Met Val Ile Val Pro Val Ser Trp Thr Ala His Asn Ile Ile
    130                 135                 140
Gln Asp Phe Tyr Asn Pro Leu Val Ala Ser Gly Gln Lys Arg Glu Met
145                 150                 155                 160
Gly Ala Ser Leu Tyr Val Gly Trp Ala Ala Ser Gly Leu Leu Leu Leu
                165                 170                 175
Gly Gly Gly Leu Leu Cys Cys Asn Cys Pro Pro Arg Thr Asp Lys Pro
            180                 185                 190
Tyr Ser Ala Lys Tyr Ser Ala Ala Arg Ser Ala Ala Ala Ser Asn Tyr
        195                 200                 205
Val Glu Gln Lys Leu Ile Ser Glu Glu Asp Leu Asn Met His Thr Gly
    210                 215                 220
His His His His His His
225                 230
```

<210> SEQ ID NO 5
<211> LENGTH: 1363
<212> TYPE: DNA
<213> ORGANISM: Homo sapiens
<220> FEATURE:
<221> NAME/KEY: CDS
<222> LOCATION: (35)..(697)

<400> SEQUENCE: 5

```
atctccttcg cagtgcagct ccttcaacct cgccatggcc tctgccggaa tgcagatcct    60
gggagtcgtc ctgacactgc tgggctgggt gaatggcctg gtctcctgtg ccctgcccat   120
gtggaaggtg accgctttca tcggcaacag catcgtggtg gcccaggtgg tgtgggaggg   180
cctgtggatg tcctgcgtgg tgcagagcac cggccagatg cagtgcaagg tgtacgactc   240
actgctggcg ctgccacagg acctgcaggc tgcacgtgcc ctctgtgtca tcgccctcct   300
tgtggccctg ttcggcttgc tggtctacct tgctggggcc aagtgtacca cctgtgtgga   360
ggagaaggat tccaaggccc gcctggtgct cacctctggg attgtctttg tcatctcagg   420
ggtcctgacg ctaatccccg tgtgctggac ggcgcatgcc gtcatccggg acttctataa   480
cccccctggtg gctgaggccc aaaagcggga gctgggggcc tccctctact gggctgggc   540
ggcctcaggc cttttgttgc tgggtggggg gttgctgtgc tgcacttgcc cctcgggggg   600
```

```
gtcccagggc cccagccatt acatggcccg ctactcaaca tctgcccctg ccatctctcg    660
ggggccctct gagtacccta ccaagaatta cgtctgacgt ggaggggaat gggggctccg    720
ctggcgctag agccatccag aagtggcagt gcccaacagc tttgggatgg gttcgtacct    780
tttgtttctg cctcctgcta ttttctttt gactgaggat atttaaaatt catttgaaaa    840
ctgagccaag gtgttgactc agactctcac ttaggctctg ctgtttctca cccttggatg    900
atggagccaa agaggggatg ctttgagatt ctggatcttg acatgcccat cttagaagcc    960
agtcaagcta tggaactaat gcggaggctg cttgctgtgc tggctttgca acaagacaga   1020
ctgtccccaa gagttcctgc tgctgctggg ggctgggctt ccctagatgt cactggacag   1080
ctgcccccca tcctactcag gtctctggag ctcctctctt caccctgga aaaacaaatg    1140 atctgttaac aaaggactgc ccacctccgg aacttctgac ctctgtttcc tccgtcctga   1200
taagacgtcc acccccagg gccaggtccc agctatgtag accccgccc ccacctccaa     1260 cactgcaccc ttctgcctg ccccctcgt ctcaccccct ttacactcac attttatca     1320 aataaagcat gttttgttag tgcaaaaaaa aaaaaaaaaa aaa                     1363
```

<210> SEQ ID NO 6
<211> LENGTH: 220
<212> TYPE: PRT
<213> ORGANISM: Homo sapiens

<400> SEQUENCE: 6

```
Met Ala Ser Ala Gly Met Gln Ile Leu Gly Val Val Leu Thr Leu Leu
  1               5                  10                  15

Gly Trp Val Asn Gly Leu Val Ser Cys Ala Leu Pro Met Trp Lys Val
                 20                  25                  30

Thr Ala Phe Ile Gly Asn Ser Ile Val Val Ala Gln Val Val Trp Glu
             35                  40                  45

Gly Leu Trp Met Ser Cys Val Val Gln Ser Thr Gly Gln Met Gln Cys
         50                  55                  60

Lys Val Tyr Asp Ser Leu Leu Ala Leu Pro Gln Asp Leu Gln Ala Ala
 65                  70                  75                  80

Arg Ala Leu Cys Val Ile Ala Leu Leu Val Ala Leu Phe Gly Leu Leu
                 85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220
```

<210> SEQ ID NO 7
<211> LENGTH: 726
<212> TYPE: DNA

```
<213> ORGANISM: Artificial sequence
<220> FEATURE:
<221> NAME/KEY: CDS
<222> LOCATION: (1)..(726)
<223> OTHER INFORMATION: Synthetic construct CLDN6-myc/His sequence

<400> SEQUENCE: 7
atggcctctg ccggaatgca gatcctggga gtcgtcctga cactgctggg ctgggtgaat      60
ggcctggtct cctgtgccct gcccatgtgg aaggtgaccg cttttcatcgg caacagcatc     120
gtggtggccc aggtggtgtg ggagggcctg tggatgtcct gcgtggtgca gagcaccggc     180
cagatgcagt gcaaggtgta cgactcactg ctggcgctgc cacaggacct gcaggctgca     240
cgtgccctct gtgtcatcgc cctccttgtg gccctgttcg gcttgctggt ctaccttgct     300
ggggccaagt gtaccacctg tgtggaggag aaggattcca aggcccgcct ggtgctcacc     360
tctgggattg tctttgtcat ctcaggggtc ctgacgctaa tccccgtgtg ctggacggcg     420
catgccgtca tccgggactt ctataacccc ctggtggctg aggcccaaaa gcgggagctg     480
ggggcctccc tctacttggg ctgggcggcc tcaggccttt tgttgctggg tgggggggttg    540
ctgtgctgca cttgccccctc gggggggtcc cagggcccca gccattacat ggcccgctac    600
tcaacatctg ccctgccat ctctcgggg ccctctgagt accctaccaa gaattacgtc        660
gaacaaaaac tcatctcaga agaggatctg aatatgcata ccggtcatca tcaccatcac     720
cattga                                                                726

<210> SEQ ID NO 8
<211> LENGTH: 241
<212> TYPE: PRT
<213> ORGANISM: Artificial sequence
<220> FEATURE:
<223> OTHER INFORMATION: Synthetic construct CLDN6-myc/His sequence

<400> SEQUENCE: 8

Met Ala Ser Ala Gly Met Gln Ile Leu Gly Val Val Leu Thr Leu Leu
  1               5                  10                  15

Gly Trp Val Asn Gly Leu Val Ser Cys Ala Leu Pro Met Trp Lys Val
             20                  25                  30

Thr Ala Phe Ile Gly Asn Ser Ile Val Val Ala Gln Val Val Trp Glu
         35                  40                  45

Gly Leu Trp Met Ser Cys Val Val Gln Ser Thr Gly Gln Met Gln Cys
     50                  55                  60

Lys Val Tyr Asp Ser Leu Leu Ala Leu Pro Gln Asp Leu Gln Ala Ala
 65                  70                  75                  80

Arg Ala Leu Cys Val Ile Ala Leu Leu Val Ala Leu Phe Gly Leu Leu
                 85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190
```

```
Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val Glu Gln Lys Leu
    210                 215                 220

Ile Ser Glu Glu Asp Leu Asn Met His Thr Gly His His His His
225                 230                 235                 240

His

<210> SEQ ID NO 9
<211> LENGTH: 60
<212> TYPE: DNA
<213> ORGANISM: Artificial sequence
<220> FEATURE:
<223> OTHER INFORMATION: Synthetic DNA

<400> SEQUENCE: 9
ccggaattca cgctgaacaa tggcctccat ggggctacag gtaatgggca tcgcgctggc      60

<210> SEQ ID NO 10
<211> LENGTH: 120
<212> TYPE: DNA
<213> ORGANISM: Artificial sequence
<220> FEATURE:
<223> OTHER INFORMATION: Synthetic DNA

<400> SEQUENCE: 10
cgatggtacc tcaatggtga tggtgatgat gaccggtatg catattcaga tcctcttctg      60
agatgagttt tgttccacg tagttgctgg cagcagcaga gcgggcagca gaatacttgg      120

<210> SEQ ID NO 11
<211> LENGTH: 60
<212> TYPE: DNA
<213> ORGANISM: Artificial sequence
<220> FEATURE:
<223> OTHER INFORMATION: Synthetic DNA

<400> SEQUENCE: 11
ccgggaattc aacctcgcca tggcctctgc cggaatgcag atcctgggag tcgtcctgac      60

<210> SEQ ID NO 12
<211> LENGTH: 120
<212> TYPE: DNA
<213> ORGANISM: Artificial sequence
<220> FEATURE:
<223> OTHER INFORMATION: Synthetic DNA

<400> SEQUENCE: 12
cgatggtacc tcaatggtga tggtgatgat gaccggtatg catattcaga tcctcttctg      60
agatgagttt tgttcgacg taattcttgg tagggtactc agagggcccc cgagagatgg      120

<210> SEQ ID NO 13
<211> LENGTH: 24
<212> TYPE: DNA
<213> ORGANISM: Artificial sequence
<220> FEATURE:
<223> OTHER INFORMATION: Synthetic construct primer of mouse IgG1 mG2aa2

<400> SEQUENCE: 13
ttgaccaggc atcctagagt cacc                                            24

<210> SEQ ID NO 14
<211> LENGTH: 30
<212> TYPE: DNA
<213> ORGANISM: Artificial sequence
```

<220> FEATURE:
<223> OTHER INFORMATION: Synthetic construct primer of mouse kappa mKa2

<400> SEQUENCE: 14
gaagcacacg actgaggcac ctccagatgt                                    30

<210> SEQ ID NO 15
<211> LENGTH: 426
<212> TYPE: DNA
<213> ORGANISM: Mus musculus
<220> FEATURE:
<221> NAME/KEY: CDS
<222> LOCATION: (1)..(426)

<400> SEQUENCE: 15

```
atg gga tgg agc tgg atc ttt ctc ttt ctc ctg tca gga act gca ggt    48
Met Gly Trp Ser Trp Ile Phe Leu Phe Leu Leu Ser Gly Thr Ala Gly
 1               5                  10                  15 ggc ctc tct gag gtc cag ctg caa caa tct gga cct gag ctg gtg aag    96
Gly Leu Ser Glu Val Gln Leu Gln Gln Ser Gly Pro Glu Leu Val Lys
             20                  25                  30 cct ggg gct tca gtg aag ata tcc tgt aag gct tct gga tac acg ttc   144
Pro Gly Ala Ser Val Lys Ile Ser Cys Lys Ala Ser Gly Tyr Thr Phe
         35                  40                  45 act gac tac tac atg aat tgg gtg aag cag agc cat gga aag agc ctt   192
Thr Asp Tyr Tyr Met Asn Trp Val Lys Gln Ser His Gly Lys Ser Leu
 50                  55                  60 gag tgg att gga gat gtt gtt cct aac aat ggt gtt cct acc tac aac   240
Glu Trp Ile Gly Asp Val Val Pro Asn Asn Gly Val Pro Thr Tyr Asn
 65                  70                  75                  80 cag aag ttc aag ggc aag gcc aca ttg act gta gac aag tcc tcc agc   288
Gln Lys Phe Lys Gly Lys Ala Thr Leu Thr Val Asp Lys Ser Ser Ser
                 85                  90                  95 aca gcc tac atg gag ctc cgc agc ctg aca tct gag gac tct gca gtc   336
Thr Ala Tyr Met Glu Leu Arg Ser Leu Thr Ser Glu Asp Ser Ala Val
            100                 105                 110 tat tac tgt gca cga ccc cat tat tac tac gct ggt aga tcg ggt gct   384
Tyr Tyr Cys Ala Arg Pro His Tyr Tyr Tyr Ala Gly Arg Ser Gly Ala
        115                 120                 125 atg gac tac tgg ggt caa gga acc tca gtc acc gtc tcc tca           426
Met Asp Tyr Trp Gly Gln Gly Thr Ser Val Thr Val Ser Ser
    130                 135                 140
```

<210> SEQ ID NO 16
<211> LENGTH: 142
<212> TYPE: PRT
<213> ORGANISM: Mus musculus

<400> SEQUENCE: 16

```
Met Gly Trp Ser Trp Ile Phe Leu Phe Leu Leu Ser Gly Thr Ala Gly
 1               5                  10                  15

Gly Leu Ser Glu Val Gln Leu Gln Gln Ser Gly Pro Glu Leu Val Lys
             20                  25                  30

Pro Gly Ala Ser Val Lys Ile Ser Cys Lys Ala Ser Gly Tyr Thr Phe
         35                  40                  45

Thr Asp Tyr Tyr Met Asn Trp Val Lys Gln Ser His Gly Lys Ser Leu
 50                  55                  60

Glu Trp Ile Gly Asp Val Val Pro Asn Asn Gly Val Pro Thr Tyr Asn
 65                  70                  75                  80

Gln Lys Phe Lys Gly Lys Ala Thr Leu Thr Val Asp Lys Ser Ser Ser
                 85                  90                  95
```

```
Thr Ala Tyr Met Glu Leu Arg Ser Leu Thr Ser Glu Asp Ser Ala Val
                100                 105                 110
Tyr Tyr Cys Ala Arg Pro His Tyr Tyr Ala Gly Arg Ser Gly Ala
            115                 120                 125
Met Asp Tyr Trp Gly Gln Gly Thr Ser Val Thr Val Ser Ser
    130                 135                 140

<210> SEQ ID NO 17
<211> LENGTH: 390
<212> TYPE: DNA
<213> ORGANISM: Mus musculus
<220> FEATURE:
<221> NAME/KEY: CDS
<222> LOCATION: (,P)..(390)

<400> SEQUENCE: 17 atg gat ttt cag gtg cag att ttc agc ttc ctg cta atc agt gcc tca       48
Met Asp Phe Gln Val Gln Ile Phe Ser Phe Leu Leu Ile Ser Ala Ser
 1               5                  10                  15 gtc ata atg tcc aga gga caa att gtt ctc acc cag tct cca gca atc       96
Val Ile Met Ser Arg Gly Gln Ile Val Leu Thr Gln Ser Pro Ala Ile
             20                  25                  30 atg tct gca tct cta ggg gaa cgg gtc acc atg acc tgc act gcc agc      144
Met Ser Ala Ser Leu Gly Glu Arg Val Thr Met Thr Cys Thr Ala Ser
         35                  40                  45 tca act gta agt tcc act tac tta cac tgg tac cag cag aag cca gga      192
Ser Thr Val Ser Ser Thr Tyr Leu His Trp Tyr Gln Gln Lys Pro Gly
     50                  55                  60 tcc tcc ccc aaa ctc tgg att tat agc aca tcc aac ctg gct tct gga      240
Ser Ser Pro Lys Leu Trp Ile Tyr Ser Thr Ser Asn Leu Ala Ser Gly
 65                  70                  75                  80 gtc cca gct cgc ttc agt ggc agt ggg tct ggg acc tct tac tct ctc      288
Val Pro Ala Arg Phe Ser Gly Ser Gly Ser Gly Thr Ser Tyr Ser Leu
                 85                  90                  95 aca atc agc agc atg gag gct gaa gat gct gcc act tat tac tgc cac      336
Thr Ile Ser Ser Met Glu Ala Glu Asp Ala Ala Thr Tyr Tyr Cys His
                100                 105                 110 cag tat cat cgt tcc cca ccc acg ttc gga ggg ggg acc aag ctg gaa      384
Gln Tyr His Arg Ser Pro Pro Thr Phe Gly Gly Gly Thr Lys Leu Glu
            115                 120                 125 ata aaa                                                              390
Ile Lys
    130

<210> SEQ ID NO 18
<211> LENGTH: 130
<212> TYPE: PRT
<213> ORGANISM: Mus musculus

<400> SEQUENCE: 18

Met Asp Phe Gln Val Gln Ile Phe Ser Phe Leu Leu Ile Ser Ala Ser
 1               5                  10                  15

Val Ile Met Ser Arg Gly Gln Ile Val Leu Thr Gln Ser Pro Ala Ile
             20                  25                  30

Met Ser Ala Ser Leu Gly Glu Arg Val Thr Met Thr Cys Thr Ala Ser
         35                  40                  45

Ser Thr Val Ser Ser Thr Tyr Leu His Trp Tyr Gln Gln Lys Pro Gly
     50                  55                  60

Ser Ser Pro Lys Leu Trp Ile Tyr Ser Thr Ser Asn Leu Ala Ser Gly
 65                  70                  75                  80

Val Pro Ala Arg Phe Ser Gly Ser Gly Ser Gly Thr Ser Tyr Ser Leu
```

```
                    85                  90                  95
Thr Ile Ser Ser Met Glu Ala Glu Asp Ala Thr Tyr Tyr Cys His
            100                 105                 110

Gln Tyr His Arg Ser Pro Pro Thr Phe Gly Gly Gly Thr Lys Leu Glu
        115                 120                 125

Ile Lys
    130

<210> SEQ ID NO 19
<211> LENGTH: 10
<212> TYPE: PRT
<213> ORGANISM: Mus musculus

<400> SEQUENCE: 19

Gly Tyr Thr Phe Thr Asp Tyr Tyr Met Asn
1               5                   10

<210> SEQ ID NO 20
<211> LENGTH: 17
<212> TYPE: PRT
<213> ORGANISM: Mus musculus

<400> SEQUENCE: 20

Asp Val Val Pro Asn Asn Gly Val Pro Thr Tyr Asn Gln Lys Phe Lys
1               5                   10                  15

Gly

<210> SEQ ID NO 21
<211> LENGTH: 14
<212> TYPE: PRT
<213> ORGANISM: Mus musculus

<400> SEQUENCE: 21

Pro His Tyr Tyr Tyr Ala Gly Arg Ser Gly Ala Met Asp Tyr
1               5                   10

<210> SEQ ID NO 22
<211> LENGTH: 12
<212> TYPE: PRT
<213> ORGANISM: Mus musculus

<400> SEQUENCE: 22

Thr Ala Ser Ser Thr Val Ser Ser Thr Tyr Leu His
1               5                   10

<210> SEQ ID NO 23
<211> LENGTH: 7
<212> TYPE: PRT
<213> ORGANISM: Mus musculus

<400> SEQUENCE: 23

Ser Thr Ser Asn Leu Ala Ser
1               5

<210> SEQ ID NO 24
<211> LENGTH: 9
<212> TYPE: PRT
<213> ORGANISM: Mus musculus

<400> SEQUENCE: 24

His Gln Tyr His Arg Ser Pro Pro Thr
1               5
```

```
<210> SEQ ID NO 25
<211> LENGTH: 1294
<212> TYPE: DNA
<213> ORGANISM: homo sapiens
<220> FEATURE:
<221> NAME/KEY: CDS
<222> LOCATION: (198)..(860)

<400> SEQUENCE: 25
caaagccaca ggcaggtgca ggcgcagccg cggcgagagc gtatggagcc gagccgttag      60
cgcgcgccgt cggtgagtca gtccgtccgt ccgtccgtcc gtcggggcgc cgcagctccc     120
gccaggccca gcggccccgg cccctcgtct ccccgcaccc ggagccaccc ggtggagcgg     180
gccttgccgc ggcagccatg tccatgggcc tggagatcac gggcaccgcg ctggccgtgc     240
tgggctggct gggcaccatc gtgtgctgcg cgttgcccat gtggcgcgtg tcggccttca     300
tcggcagcaa catcatcacg tcgcagaaca tctgggaggg cctgtggatg aactgcgtgg     360
tgcagagcac cggccagatg cagtgcaagg tgtacgactc gctgctggca ctgccacagg     420
accttcaggc ggcccgcgcc ctcatcgtgg tggccatcct gctggccgcc ttcgggctgc     480
tagtggcgct ggtgggcgcc cagtgcacca actgcgtgca ggacgacacg gccaaggcca     540
agatcaccat cgtggcaggc gtgctgttcc ttctcgccgc cctgctcacc ctcgtgccgg     600
tgtcctggtc ggccaacacc attatccggg acttctacaa ccccgtggtg cccgaggcgc     660
agaagcgcga gatgggcgcg ggcctgtacg tgggctgggc ggccgcggcg ctgcagctgc     720
tggggggcgc gctgctctgc tgctcgtgtc ccccacgcga gaagaagtac acggccacca     780
aggtcgtcta ctccgcgccg cgctccaccg gcccgggagc cagcctgggc acaggctacg     840
accgcaagga ctacgtctaa gggacagacg cagggagacc ccaccaccac caccaccacc     900
aacaccacca ccaccaccgc gagctggagc gcgcaccagg ccatccagcg tgcagccttg     960
cctcggaggc cagcccaccc ccagaagcca ggaagccccc gcgctggact ggggcagctt    1020
ccccagcagc cacggctttg cgggccgggc agtcgacttc ggggcccagg gaccaacctg    1080
catggactgt gaaacctcac ccttctggag cacggggcct gggtgaccgc caatacttga    1140
ccaccccgtc gagccccatc gggccgctgc ccccatgctc gcgctgggca gggaccggca    1200
gccctggaag gggcacttga tattttttcaa taaaagcctt tcgttttgca aaaaaaaaa    1260 aaaaaaaaaa aaaaaaaaaa aaaaaaaaaa aaaa                                1294

<210> SEQ ID NO 26
<211> LENGTH: 220
<212> TYPE: PRT
<213> ORGANISM: Homo sapiens

<400> SEQUENCE: 26

Met Ser Met Gly Leu Glu Ile Thr Gly Thr Ala Leu Ala Val Leu Gly
  1               5                  10                  15

Trp Leu Gly Thr Ile Val Cys Cys Ala Leu Pro Met Trp Arg Val Ser
                 20                  25                  30

Ala Phe Ile Gly Ser Asn Ile Ile Thr Ser Gln Asn Ile Trp Glu Gly
             35                  40                  45

Leu Trp Met Asn Cys Val Val Gln Ser Thr Gly Gln Met Gln Cys Lys
         50                  55                  60

Val Tyr Asp Ser Leu Leu Ala Leu Pro Gln Asp Leu Gln Ala Ala Arg
 65                  70                  75                  80

Ala Leu Ile Val Val Ala Ile Leu Leu Ala Ala Phe Gly Leu Leu Val
                 85                  90                  95
```

```
Ala Leu Val Gly Ala Gln Cys Thr Asn Cys Val Gln Asp Asp Thr Ala
                100                 105                 110

Lys Ala Lys Ile Thr Ile Val Ala Gly Val Leu Phe Leu Leu Ala Ala
            115                 120                 125

Leu Leu Thr Leu Val Pro Val Ser Trp Ser Ala Asn Thr Ile Ile Arg
130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly
                165                 170                 175

Gly Ala Leu Leu Cys Cys Ser Cys Pro Pro Arg Glu Lys Lys Tyr Thr
            180                 185                 190

Ala Thr Lys Val Val Tyr Ser Ala Pro Arg Ser Thr Gly Pro Gly Ala
            195                 200                 205

Ser Leu Gly Thr Gly Tyr Asp Arg Lys Asp Tyr Val
210                 215                 220
```

<210> SEQ ID NO 27
<211> LENGTH: 726
<212> TYPE: DNA
<213> ORGANISM: Artificicial sequence
<220> FEATURE:
<221> NAME/KEY: CDS
<222> LOCATION: (1)..(726)
<223> OTHER INFORMATION: Synthetic construct CLDN3-myc/His sequence

<400> SEQUENCE: 27

```
atgtccatgg gcctggagat cacgggcacc gcgctggccg tgctgggctg gctgggcacc      60
atcgtgtgct gcgcgttgcc catgtggcgc gtgtcggcct tcatcggcag caacatcatc     120
acgtcgcaga acatctggga gggcctgtgg atgaactgcg tggtgcagag caccggccag     180
atgcagtgca aggtgtacga ctcgctgctg gcactgccac aggaccttca ggcggcccgc     240
gccctcatcg tggtggccat cctgctggcc gccttcgggc tgctagtggc gctggtgggc     300
gcccagtgca ccaactgcgt gcaggacgac acggccaagg ccaagatcac catcgtggcg     360
ggcgtgctgt tccttctcgc cgccctgctc accctcgtgc cggtgtcctg gtcggccaac     420
accattatcc gggacttcta caaccccgtg gtgcccgagg cgcagaagcg cgagatgggc     480
gcgggcctgt acgtgggctg gcggccgcg gcgctgcagc tgctgggggg cgcgctgctc     540
tgctgctcgt gtccccacg cgagaagaag tacacggcca ccaaggtcgt ctactccgcg     600
ccgcgctcca ccggcccggg agccagcctg ggcacaggct acgaccgcaa ggactacgtc     660
gaacaaaaac tcatctcaga agaggatctg aatatgcata ccggtcatca tcaccatcac     720
cattga                                                                726
```

<210> SEQ ID NO 28
<211> LENGTH: 241
<212> TYPE: PRT
<213> ORGANISM: Artificial sequence
<220> FEATURE:
<223> OTHER INFORMATION: Synthetic construct CLDN3-myc/His sequence

<400> SEQUENCE: 28

```
Met Ser Met Gly Leu Glu Ile Thr Gly Thr Ala Leu Ala Val Leu Gly
  1               5                  10                  15

Trp Leu Gly Thr Ile Val Cys Cys Ala Leu Pro Met Trp Arg Val Ser
            20                  25                  30

Ala Phe Ile Gly Ser Asn Ile Ile Thr Ser Gln Asn Ile Trp Glu Gly
        35                  40                  45
```

```
Leu Trp Met Asn Cys Val Val Gln Ser Thr Gly Gln Met Gln Cys Lys
 50                  55                  60

Val Tyr Asp Ser Leu Leu Ala Leu Pro Gln Asp Leu Gln Ala Ala Arg
 65                  70                  75                  80

Ala Leu Ile Val Val Ala Ile Leu Leu Ala Ala Phe Gly Leu Leu Val
                 85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Ala Ala
        115                 120                 125

Leu Leu Thr Leu Val Pro Val Ser Trp Ser Ala Asn Thr Ile Ile Arg
130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly
                165                 170                 175

Gly Ala Leu Leu Cys Cys Ser Cys Pro Pro Arg Glu Lys Lys Tyr Thr
            180                 185                 190

Ala Thr Lys Val Val Tyr Ser Ala Pro Arg Ser Thr Gly Pro Gly Ala
        195                 200                 205

Ser Leu Gly Thr Gly Tyr Asp Arg Lys Asp Tyr Val Glu Gln Lys Leu
210                 215                 220

Ile Ser Glu Glu Asp Leu Asn Met His Thr Gly His His His His
225                 230                 235                 240

His

<210> SEQ ID NO 29
<211> LENGTH: 1730
<212> TYPE: DNA
<213> ORGANISM: Homo sapiens
<220> FEATURE:
<221> NAME/KEY: CDS
<222> LOCATION: (471)..(1127)

<400> SEQUENCE: 29
gtctctcctg tctgaaggcc agagcaggct gctaggcctg gggccaccac tgcccctggg     60
tgctacaccc agtgtgatgg gtcactggga acttcctgaa gtggtgtcac ctgaactggg    120
cccccaagga tggggtgcgg gcagtaccgc aggaagagga gcagcccctg tgaagattga    180
gagctgccag aggctctgtg attggctgcg gcacgatgac ccgcgcacgg attggctgct    240
tcgggccggg gggccgggcc cgggggacag aatccgcccc cgaaccttca agagggtac     300
ccccccggcag gagctggcag acccaggagg tgcgacagac ccgcggggca aacggactgg    360
ggccaagagc cgggagcgcg ggcgcaaagg caccagggcc cgcccagggc gccgcgcagc    420
acggccttgg gggttctgcg ggccttcggg tgcgcgtctc gcctctagcc atggggtccg    480
cagcgttgga gatcctgggc ctggtgctgt gcctggtggg ctggggggt ctgatcctgg    540
cgtgcgggct gccatgtgg caggtgaccg ccttcctgga ccacaacatc gtgacgcgc    600
agaccacctg gaaggggctg tggatgtcgt gcgtggtgca gagcaccggg cacatgcagt    660
gcaaagtgta cgactcggtg ctggctctga caccgaggt gcaggcggcg cgggcgctca    720
ccgtgagcgc cgtgctgctg gcgttcgttg cgctcttcgt gaccctggcg ggcgcgcagt    780
gcaccacctg cgtggcccccg ggccggcca aggcgcgtgt ggccctcacg ggaggcgtgc    840
tctacctgtt ttgcgggctg ctggcgctcg tgccactctg ctggttcgcc aacattgtcg    900
```

```
tccgcgagtt ttacgacccg tctgtgcccg tgtcgcagaa gtacgagctg ggcgcagcgc    960
tgtacatcgg ctgggcggcc accgcgctgc tcatggtagg cggctgcctc ttgtgctgcg   1020
gcgcctgggt ctgcaccggc cgtcccgacc tcagcttccc cgtgaagtac tcagcgccgc   1080
ggcggcccac ggccaccggc gactacgaca agaagaacta cgtctgaggg cgctgggcac   1140
ggccgggccc ctcctgccag ccacgcctgc gaggcgttgg ataagcctgg ggagccccgc   1200
atggaccgcg gcttccgccg ggtagcgcgg cgcgcaggct cctcggaacg tccggctctg   1260
cgccccgacg cggctcctgg atccgctcct gcctgcgccc gcagctgacc ttctcctgcc   1320
actagcccgg ccctgccctt aacagacgga atgaagtttc cttttctgtg cgcggcgctg   1380
tttccatagg cagagcgggt gtcagactga ggatttcgct tcccctccaa gacgctgggg   1440
gtcttggctg ctgccttact tcccagaggc tcctgctgac ttcggagggg cggatgcaga   1500
gcccagggcc cccaccggaa gatgtgtaca gctggtcttt actccatcgg cagggcccga   1560
gcccagggac cagtgacttg gcctggacct cccggtctca ctccagcatc tccccaggca   1620
aggcttgtgg gcaccggagc ttgagagagg gcgggagtgg gaaggctaag aatctgctta   1680
gtaaatggtt tgaactctca aaaaaaaaaa aaaaaaaaa  aaaaaaaaa              1730
```

<210> SEQ ID NO 30
<211> LENGTH: 218
<212> TYPE: PRT
<213> ORGANISM: Homo sapiens

<400> SEQUENCE: 30

Met Gly Ser Ala Ala Leu Glu Ile Leu Gly Leu Val Leu Cys Leu Val
 1               5                  10                  15

Gly Trp Gly Gly Leu Ile Leu Ala Cys Gly Leu Pro Met Trp Gln Val
                20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
        50                  55                  60

Lys Val Tyr Asp Ser Val Leu Ala Leu Ser Thr Glu Val Gln Ala Ala
    65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
        195                 200                 205

Thr Gly Asp Tyr Asp Lys Lys Asn Tyr Val
    210                 215

<210> SEQ ID NO 31

<211> LENGTH: 720
<212> TYPE: DNA
<213> ORGANISM: Artificial sequence
<220> FEATURE:
<221> NAME/KEY: CDS
<222> LOCATION: (1)..(720)
<223> OTHER INFORMATION: Synthetic construct CLDN5-myc/His sequence

<400> SEQUENCE: 31

```
atggggtccg cagcgttgga gatcctgggc ctggtgctgt gcctggtggg ctgggggggt    60
ctgatcctgg cgtgcgggct gcccatgtgg caggtgaccg ccttcctgga ccacaacatc   120
gtgacggcgc agaccacctg gaaggggctg tggatgtcgt gcgtggtgca gagcaccggg   180
cacatgcagt gcaaagtgta cgactcggtg ctggctctga gcaccgaggt gcaggcggcg   240
cgggcgctca ccgtgagcgc cgtgctgctg gcgttcgttg cgctcttcgt gaccctggcg   300
ggcgcgcagt gcaccacctg cgtggccccg ggcccggcca aggcgcgtgt ggccctcacg   360
ggaggcgtgc tctacctgtt tgcgggctg ctggcgctcg tgccactctg ctggttcgcc   420
aacattgtcg tccgcgagtt ttacgacccg tctgtgcccg tgtcgcagaa gtacgagctg   480
ggcgcagcgc tgtacatcgg ctgggcggcc accgcgctgc tcatggtagg cggctgcctc   540
ttgtgctgcg gcgcctgggt ctgcaccggc cgtcccgacc tcagcttccc cgtgaagtac   600
tcagcgccgc ggcggcccac ggccaccggc gactacgaca agaagaacta cgtcgaacaa   660
aaactcatct cagaagagga tctgaatatg cataccggtc atcatcacca tcaccattga   720
```

<210> SEQ ID NO 32
<211> LENGTH: 239
<212> TYPE: PRT
<213> ORGANISM: Artificial sequence
<220> FEATURE:
<223> OTHER INFORMATION: Synthetic construct CLDN5-myc/His sequence

<400> SEQUENCE: 32

```
Met Gly Ser Ala Ala Leu Glu Ile Leu Gly Leu Val Leu Cys Leu Val
  1               5                  10                  15
Gly Trp Gly Gly Leu Ile Leu Ala Cys Gly Leu Pro Met Trp Gln Val
             20                  25                  30
Thr Ala Phe Leu Asp His Asn Ile Val Thr Ala Gln Thr Thr Trp Lys
         35                  40                  45
Gly Leu Trp Met Ser Cys Val Val Gln Ser Thr Gly His Met Gln Cys
     50                  55                  60
Lys Val Tyr Asp Ser Val Leu Ala Leu Ser Thr Glu Val Gln Ala Ala
 65                  70                  75                  80
Arg Ala Leu Thr Val Ser Ala Val Leu Leu Ala Phe Val Ala Leu Phe
                 85                  90                  95
Val Thr Leu Ala Gly Ala Gln Cys Thr Thr Cys Val Ala Pro Gly Pro
            100                 105                 110
Ala Lys Ala Arg Val Ala Leu Thr Gly Gly Val Leu Tyr Leu Phe Cys
        115                 120                 125
Gly Leu Leu Ala Leu Val Pro Leu Cys Trp Phe Ala Asn Ile Val Val
    130                 135                 140
Arg Glu Phe Tyr Asp Pro Ser Val Pro Val Ser Gln Lys Tyr Glu Leu
145                 150                 155                 160
Gly Ala Ala Leu Tyr Ile Gly Trp Ala Ala Thr Ala Leu Leu Met Val
                165                 170                 175
Gly Gly Cys Leu Leu Cys Cys Gly Ala Trp Val Cys Thr Gly Arg Pro
            180                 185                 190
```

```
Asp Leu Ser Phe Pro Val Lys Tyr Ser Ala Pro Arg Arg Pro Thr Ala
        195                 200                 205

Thr Gly Asp Tyr Asp Lys Lys Asn Tyr Val Glu Gln Lys Leu Ile Ser
210                 215                 220

Glu Glu Asp Leu Asn Met His Thr Gly His His His His His His
225                 230                 235

<210> SEQ ID NO 33
<211> LENGTH: 1804
<212> TYPE: DNA
<213> ORGANISM: Homo sapiens
<220> FEATURE:
<221> NAME/KEY: CDS
<222> LOCATION: (573)..(1226)

<400> SEQUENCE: 33
aacctccaca acaggcccct catcctcgca ccctccccgt ggctcaggtc tccctatcc      60 cggcctccct gcacttcact ctgctcctcc cctgcctggg ccttaaaacc ccgcctgcag    120
ccgagagccc gcagagtccc caggtggcac tgtcagagtc gctcagtggg aacctgcgcc    180
agccggcagg agacgtggct gtcctcagcc tggcagtgcg tctggagggc ctgtgcgagc    240
tcagcccagg tgtgacagcg gggtggtaag agcagcagca ccctcagggc atccgatggg    300
cggaggcccc tcgaggtgac acccaccact cagccgagcg ggactacgag tctgctttgt    360
gctccgcgag gaccagaaac acctgcaaga ggcacggaga ggaggcgcct ttcaagaggc    420
gcctttcatg gaactgagga ctggcctggc ttggggacac caacaagcct tcccctcct    480 gctggacaca gagacaccca cccagcacac cagacacacc ctctgagtca cctaggccgc    540
ctggggctga agacctaa ccgaggggcc agatggcttc gaccggctta gaactgctgg      600
gcatgaccct ggctgtgctg ggctggctgg ggaccctggt gtcctgcgcc ctgcccctgt    660
ggaaggtgac cgccttcatc ggcaacagca tcgtggtggc ccaggtggtg tgggagggcc    720
tgtggatgtc ctgcgtggtg cagagcacgg gccagatgca gtgcaaggtg tacgactcac    780
tgctggctct gccgcaggac ctgcaggccg cacgtgccct ctgtgtcatt gccctcctgc    840
tggccctgct tggcctcctg gtggccatca caggtgccca gtgtaccacg tgtgtggagg    900
acgaaggtgc caaggcccgt atcgtgctca ccgcggggt catcctcctc ctcgccggca    960
tcctggtgct catccctgtg tgctggacgg cgcacgccat catccaggac ttctacaacc   1020
ccctggtggc tgaggccctc aagcgggagc tgggggcctc cctctacctg gctgggcgg    1080 cggctgcact gcttatgctg ggcggggggc tcctctgctg cacgtgcccc ccgcccagg   1140 tcgagcggcc ccgcggacct cggctgggct actccatccc ctcccgctcg ggtgcatctg   1200
gactggacaa gagggactac gtgtgaggcg gaggtttccc ctgggagccc actgctcccc   1260
actgccccgc cctttcgacc ttggcctgat gaccagatgc cctgctccat cacaacctcc   1320
ttccccagga aaacccactt tccaaaagcc caagctacac ctggctgcag gctgggtca    1380 gctggcctgg ctgagctctt ctcagtgggg tccctttga tgttctcccc caagttgggc   1440
agcctagagg tgttgggaac cctggcctgc ccccacctcc ccagtaattg tttccttccg   1500
ttgcccagga cactggctgg ccttccttct cttctgagcc ctccctgcc ccaggaaccc    1560 tggcctcacc aaaacagcag cagctcgttg gctccaaaac cagggagcag accatgccct   1620
cccaaccctg gagttgtcag ggagggcctg cccatcacct ccctctcccc aacatcccca   1680
ccctcgagtt ggaaataaag agcatttgta actggaaaaa aaaaaaaaa aaaaaaaaa    1740 aaaaaaaaaa aaaaaaaaaa aaaaaaaaaa aaaaaaaaaa aaaaaaaaaa aaaaaaaaaa   1800
```

-continued aaaa 1804

<210> SEQ ID NO 34
<211> LENGTH: 217
<212> TYPE: PRT
<213> ORGANISM: Homo sapiens

<400> SEQUENCE: 34

Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Ala Leu Gly Leu Leu
                85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
    130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Pro Gln Val Glu Arg
            180                 185                 190

Pro Arg Gly Pro Arg Leu Gly Tyr Ser Ile Pro Ser Arg Ser Gly Ala
        195                 200                 205

Ser Gly Leu Asp Lys Arg Asp Tyr Val
    210                 215

<210> SEQ ID NO 35
<211> LENGTH: 717
<212> TYPE: DNA
<213> ORGANISM: Artificial sequence
<220> FEATURE:
<221> NAME/KEY: CDS
<222> LOCATION: (1)..(717)
<223> OTHER INFORMATION: Synthetic construct CLDN9-myc/His sequence

<400> SEQUENCE: 35
atggcttcga ccggcttaga actgctgggc atgaccctgg ctgtgctggg ctggctgggg      60
accctggtgt cctgcgccct gcccctgtgg aaggtgaccg ccttcatcgg caacagcatc     120
gtggtggccc aggtggtgtg ggagggcctg tggatgtcct gcgtggtgca gagcacgggc     180
cagatgcagt gcaaggtgta cgactcactg ctggctctgc cgcaggacct gcaggccgca     240
cgtgccctct gtgtcattgc cctcctgctg gccctgcttg gctcctggt ggccatcaca     300 ggtgcccagt gtaccacgtg tgtggaggac gaaggtgcca aggcccgtat cgtgctcacc     360 gcggggtca tcctcctcct cgccggcatc ctggtgctca tccctgtgtg ctggacggcg     420
cacgccatca tccaggactt ctacaacccc ctggtggctg aggccctcaa gcgggagctg     480

```
ggggcctccc tctacctggg ctgggcggcg gctgcactgc ttatgctggg cggggggctc    540
ctctgctgca cgtgcccccc gccccaggtc gagcggcccc gcggacctcg gctgggctac    600
tccatcccct cccgctcggg tgcatctgga ctggacaaga gggactacgt ggaacaaaaa    660
ctcatctcag aagaggatct gaatatgcat accggtcatc atcaccatca ccattga      717
```

<210> SEQ ID NO 36
<211> LENGTH: 238
<212> TYPE: PRT
<213> ORGANISM: Artificial sequence
<220> FEATURE:
<223> OTHER INFORMATION: Synthetic construct CLDN9-myc/His sequence

<400> SEQUENCE: 36

```
Met Ala Ser Thr Gly Leu Glu Leu Leu Gly Met Thr Leu Ala Val Leu
 1               5                  10                  15

Gly Trp Leu Gly Thr Leu Val Ser Cys Ala Leu Pro Leu Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Leu Ala Leu Gly Leu Leu
                85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
    130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Gln Val Glu Arg
            180                 185                 190

Pro Arg Gly Pro Arg Leu Gly Tyr Ser Ile Pro Ser Arg Ser Gly Ala
        195                 200                 205

Ser Gly Leu Asp Lys Arg Asp Tyr Val Glu Gln Lys Leu Ile Ser Glu
    210                 215                 220

Glu Asp Leu Asn Met His Thr Gly His His His His His
225                 230                 235
```

<210> SEQ ID NO 37
<211> LENGTH: 18
<212> TYPE: DNA
<213> ORGANISM: Artificial sequence
<220> FEATURE:
<223> OTHER INFORMATION: Synthetic DNA

<400> SEQUENCE: 37

```
gcagccatgt ccatgggc                                                   18
```

<210> SEQ ID NO 38
<211> LENGTH: 19
<212> TYPE: DNA
<213> ORGANISM: Artificial sequence

```
<220> FEATURE:
<223> OTHER INFORMATION: Synthetic DNA

<400> SEQUENCE: 38
agacgtagtc cttgcggtc                                                    19

<210> SEQ ID NO 39
<211> LENGTH: 60
<212> TYPE: DNA
<213> ORGANISM: Artificial sequence
<220> FEATURE:
<223> OTHER INFORMATION: Synthetic DNA

<400> SEQUENCE: 39
ccggaattcc gcggcagcca tgtccatggg cctggagatc acgggcaccg cgctggccgt        60

<210> SEQ ID NO 40
<211> LENGTH: 120
<212> TYPE: DNA
<213> ORGANISM: Artificial sequence
<220> FEATURE:
<223> OTHER INFORMATION: Synthetic DNA

<400> SEQUENCE: 40
cgatggtacc tcaatggtga tggtgatgat gaccggtatg catattcaga tcctcttctg        60
agatgagttt ttgttcgacg tagtccttgc ggtcgtagcc tgtgcccagg ctggctcccg      120

<210> SEQ ID NO 41
<211> LENGTH: 60
<212> TYPE: DNA
<213> ORGANISM: Artificial sequence
<220> FEATURE:
<223> OTHER INFORMATION: Synthetic DNA

<400> SEQUENCE: 41
ccggaattcg cctctagcca tggggtccgc agcgttggag atcctgggcc tggtgctgtg        60

<210> SEQ ID NO 42
<211> LENGTH: 120
<212> TYPE: DNA
<213> ORGANISM: Artificial sequence
<220> FEATURE:
<223> OTHER INFORMATION: Synthetic DNA

<400> SEQUENCE: 42
cgatggtacc tcaatggtga tggtgatgat gaccggtatg catattcaga tcctcttctg        60
agatgagttt ttgttcgacg tagttcttct tgtcgtagtc gccggtggcc gtgggccgcc      120

<210> SEQ ID NO 43
<211> LENGTH: 40
<212> TYPE: DNA
<213> ORGANISM: Artificial sequence
<220> FEATURE:
<223> OTHER INFORMATION: Synthetic DNA

<400> SEQUENCE: 43
ccggaattcg aggggccaga tggcttcgac cggcttagaa                              40

<210> SEQ ID NO 44
<211> LENGTH: 180
<212> TYPE: DNA
<213> ORGANISM: Artificial sequence
<220> FEATURE:
<223> OTHER INFORMATION: Synthetic DNA

<400> SEQUENCE: 44
```

```
cgtggtgcag agcacgggcc agatgcagtg caaggtgtac gactcactgc tggctctgcc      60
gcaggacctg caggccgcac gtgccctctg tgtcattgcc ctcctgctgg ccctgcttgg     120
cctcctggtg gccatcacag gtgcccagtg taccacgtgt gtggaggacg aaggtgccaa     180
```

<210> SEQ ID NO 45
<211> LENGTH: 150
<212> TYPE: DNA
<213> ORGANISM: Artificial sequence
<220> FEATURE:
<223> OTHER INFORMATION: Synthetic DNA

<400> SEQUENCE: 45

```
gggcctccct ctacctgggc tgggcggcgg ctgcactgct tatgctgggc gggggctcc      60 tctgctgcac gtgcccccg ccccaggtcg agcggccccg cggacctcgg ctgggctact     120
ccatcccctc ccgctcgggt gcatctggac                                      150
```

<210> SEQ ID NO 46
<211> LENGTH: 180
<212> TYPE: DNA
<213> ORGANISM: Artificial sequence
<220> FEATURE:
<223> OTHER INFORMATION: Synthetic DNA

<400> SEQUENCE: 46

```
ggcccgtgct ctgcaccacg caggacatcc acaggccctc ccacaccacc tgggccacca     60
cgatgctgtt gccgatgaag gcggtcacct tccacagggg cagggcgcag acaccaggg     120 tccccagcca gcccagcaca gccagggtca tgcccagcag ttctaagccg gtcgaagcca    180
```

<210> SEQ ID NO 47
<211> LENGTH: 180
<212> TYPE: DNA
<213> ORGANISM: Artificial sequence
<220> FEATURE:
<223> OTHER INFORMATION: Synthetic DNA

<400> SEQUENCE: 47

```
gcccaggtag agggaggccc ccagctcccg cttgagggcc tcagccacca gggggttgta     60
gaagtcctgg atgatggcgt gcgccgtcca gcacacaggg atgagcacca ggatgccggc    120
gaggaggagg atgaccccg cggtgagcac gatacgggcc ttggcacctt cgtcctccac    180
```

<210> SEQ ID NO 48
<211> LENGTH: 120
<212> TYPE: DNA
<213> ORGANISM: Artificial sequence
<220> FEATURE:
<223> OTHER INFORMATION: Synthetic DNA

<400> SEQUENCE: 48

```
cgatggtacc tcaatggtga tggtgatgat gaccggtatg catattcaga tcctcttctg     60
agatgagttt ttgttccacg tagtccctct tgtccagtcc agatgcaccc gagcgggagg    120
```

<210> SEQ ID NO 49
<211> LENGTH: 141
<212> TYPE: DNA
<213> ORGANISM: Artificial sequence
<220> FEATURE:
<223> OTHER INFORMATION: Synthetic DNA KM3900H Foward

<400> SEQUENCE: 49

```
ccgcggccgc gaccctcac catgaacctc gggctcagtt tgatttttcct tgccctcatt     60
```

```
ttaaaaggtg tccagtgtga ggtccagctg caacaatctg gacctgagct ggtgaagcct    120
ggggcttcag tgaagatatc c                                             141
```

<210> SEQ ID NO 50
<211> LENGTH: 40
<212> TYPE: DNA
<213> ORGANISM: Artificial sequence
<220> FEATURE:
<223> OTHER INFORMATION: Synthetic DNA KM3900H Reverse

<400> SEQUENCE: 50

```
cgatgggccc ttggtggagg ctgaggagac ggtgactgag                         40
```

<210> SEQ ID NO 51
<211> LENGTH: 139
<212> TYPE: DNA
<213> ORGANISM: Artificial sequence
<220> FEATURE:
<223> OTHER INFORMATION: Synthetic DNA KM3900L Foward

<400> SEQUENCE: 51

```
ccgaattcgc ctcttcaaaa tgaagttgcc tgttaggctg ttggtgctga tgttctggat    60
tcctgcttcc agcagtcaaa ttgttctcac ccagtctcca gcaatcatgt ctgcatctct    120
aggggaacgg gtcaccatg                                                139
```

<210> SEQ ID NO 52
<211> LENGTH: 40
<212> TYPE: DNA
<213> ORGANISM: Artificial sequence
<220> FEATURE:
<223> OTHER INFORMATION: Synthetic DNA KM3900L Reverse

<400> SEQUENCE: 52

```
agccaccgta cgttttattt ccagcttggt cccccctccg                         40
```

<210> SEQ ID NO 53
<211> LENGTH: 23
<212> TYPE: DNA
<213> ORGANISM: Artificial sequence
<220> FEATURE:
<223> OTHER INFORMATION: Synthetic construct primer of mouse IgG

<400> SEQUENCE: 53

```
cagtggatag accgatgggg ctg                                           23
```

<210> SEQ ID NO 54
<211> LENGTH: 32
<212> TYPE: DNA
<213> ORGANISM: Artificial sequence
<220> FEATURE:
<223> OTHER INFORMATION: Synthetic construct primer of mouse kappa

<400> SEQUENCE: 54

```
ctaacactca ttcctgttga agctcttgac aa                                 32
```

<210> SEQ ID NO 55
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 55

```
atg gaa tgg cct tgt atc ttt ctc ttc ctc ctg tca gta act gaa ggt      48
Met Glu Trp Pro Cys Ile Phe Leu Phe Leu Leu Ser Val Thr Glu Gly
 1               5                  10                 15 gtc cac tcc cag gtt cag ctg cag cag tct gga cct gag ctg gtg aag      96
Val His Ser Gln Val Gln Leu Gln Gln Ser Gly Pro Glu Leu Val Lys
            20                  25                  30 cct ggg gcc tca gtg aag att tcc tgc aag gct tct ggc tac gca ata     144
Pro Gly Ala Ser Val Lys Ile Ser Cys Lys Ala Ser Gly Tyr Ala Ile
        35                  40                  45 agt acc tcc tgg atg aac tgg gtg aag cag agg cct gga aag ggt ctt     192
Ser Thr Ser Trp Met Asn Trp Val Lys Gln Arg Pro Gly Lys Gly Leu
    50                  55                  60 gag tgg att gga cgg att aat cct gga gat gga aat acc aac tac aat     240
Glu Trp Ile Gly Arg Ile Asn Pro Gly Asp Gly Asn Thr Asn Tyr Asn
65                  70                  75                  80 ggg aaa ttc atg gcc aag gcc aca ctg act gca gac aaa ccc tcc agc     288
Gly Lys Phe Met Ala Lys Ala Thr Leu Thr Ala Asp Lys Pro Ser Ser
                85                  90                  95 aca gcc tac atg caa ctc agc agc ctg aca tct gag gac tct gcg gtc     336
Thr Ala Tyr Met Gln Leu Ser Ser Leu Thr Ser Glu Asp Ser Ala Val
            100                 105                 110 tac ttc tgt aca aga ggg gat cga tgg tcg ggg gcc atg gac tac tgg     384
Tyr Phe Cys Thr Arg Gly Asp Arg Trp Ser Gly Ala Met Asp Tyr Trp
        115                 120                 125 ggt caa gga acc tca gtc acc gtc tcc tca                             414
Gly Gln Gly Thr Ser Val Thr Val Ser Ser
    130                 135
```

<210> SEQ ID NO 56
<211> LENGTH: 138
<212> TYPE: PRT
<213> ORGANISM: Mus musculus

<400> SEQUENCE: 56

```
Met Glu Trp Pro Cys Ile Phe Leu Phe Leu Leu Ser Val Thr Glu Gly
 1               5                  10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Ile
        35                  40                  45

Ser Thr Ser Trp Met Asn Trp Val Lys Gln Arg Pro Gly Lys Gly Leu
    50                  55                  60

Glu Trp Ile Gly Arg Ile Asn Pro Gly Asp Gly Asn Thr Asn Tyr Asn
65                  70                  75                  80

Gly Lys Phe Met Ala Lys Ala Thr Leu Thr Ala Asp Lys Pro Ser Ser
                85                  90                  95

Thr Ala Tyr Met Gln Leu Ser Ser Leu Thr Ser Glu Asp Ser Ala Val
            100                 105                 110

Tyr Phe Cys Thr Arg Gly Asp Arg Trp Ser Gly Ala Met Asp Tyr Trp
        115                 120                 125

Gly Gln Gly Thr Ser Val Thr Val Ser Ser
    130                 135
```

<210> SEQ ID NO 57
<211> LENGTH: 390
<212> TYPE: DNA
<213> ORGANISM: Mus musculus
<220> FEATURE:
<221> NAME/KEY: CDS
<222> LOCATION: (1)..(390)

```
<400> SEQUENCE: 57 atg gat ttt ctg gtg cag att ttc agc ttc ttg cta atc agt gcc tca      48
Met Asp Phe Leu Val Gln Ile Phe Ser Phe Leu Leu Ile Ser Ala Ser
 1               5                  10                  15 gtt gca atg tcc aga gga gga aat gtg ctc acc cag tct cca gca atc      96
Val Ala Met Ser Arg Gly Gly Asn Val Leu Thr Gln Ser Pro Ala Ile
             20                  25                  30 atg tct gca tct cca ggg gaa aag gtc acc atg acc tgc agg gcc agc     144
Met Ser Ala Ser Pro Gly Glu Lys Val Thr Met Thr Cys Arg Ala Ser
         35                  40                  45 tca agt gta agt tcc agt tac ttg cac tgg tac cag cag aag tca ggt     192
Ser Ser Val Ser Ser Ser Tyr Leu His Trp Tyr Gln Gln Lys Ser Gly
     50                  55                  60 gcc tcc ccc aaa ctc tgg att tat agc aca tcc aac ttg gct tct gga     240
Ala Ser Pro Lys Leu Trp Ile Tyr Ser Thr Ser Asn Leu Ala Ser Gly
 65                  70                  75                  80 gtc cct gtt cgc ttc agt ggc agt ggg tct ggg acc tct tac tct ctc     288
Val Pro Val Arg Phe Ser Gly Ser Gly Ser Gly Thr Ser Tyr Ser Leu
                 85                  90                  95 aca atc agc agt gtg gag gct gaa gat gct gcc act tat tac tgc cag     336
Thr Ile Ser Ser Val Glu Ala Glu Asp Ala Ala Thr Tyr Tyr Cys Gln
            100                 105                 110 cag tac agt ggt ttc ccg ctc acg ttc ggt gct ggg acc aag ctg gaa     384
Gln Tyr Ser Gly Phe Pro Leu Thr Phe Gly Ala Gly Thr Lys Leu Glu
        115                 120                 125 ctg aaa                                                              390
Leu Lys
   130

<210> SEQ ID NO 58
<211> LENGTH: 130
<212> TYPE: PRT
<213> ORGANISM: Mus musculus

<400> SEQUENCE: 58

Met Asp Phe Leu Val Gln Ile Phe Ser Phe Leu Leu Ile Ser Ala Ser
 1               5                  10                  15

Val Ala Met Ser Arg Gly Gly Asn Val Leu Thr Gln Ser Pro Ala Ile
             20                  25                  30

Met Ser Ala Ser Pro Gly Glu Lys Val Thr Met Thr Cys Arg Ala Ser
         35                  40                  45

Ser Ser Val Ser Ser Ser Tyr Leu His Trp Tyr Gln Gln Lys Ser Gly
     50                  55                  60

Ala Ser Pro Lys Leu Trp Ile Tyr Ser Thr Ser Asn Leu Ala Ser Gly
 65                  70                  75                  80

Val Pro Val Arg Phe Ser Gly Ser Gly Ser Gly Thr Ser Tyr Ser Leu
                 85                  90                  95

Thr Ile Ser Ser Val Glu Ala Glu Asp Ala Ala Thr Tyr Tyr Cys Gln
            100                 105                 110

Gln Tyr Ser Gly Phe Pro Leu Thr Phe Gly Ala Gly Thr Lys Leu Glu
        115                 120                 125

Leu Lys
   130

<210> SEQ ID NO 59
<211> LENGTH: 5
<212> TYPE: PRT
<213> ORGANISM: Mus musculus

<400> SEQUENCE: 59
```

```
Thr Ser Trp Met Asn
  1               5

<210> SEQ ID NO 60
<211> LENGTH: 17
<212> TYPE: PRT
<213> ORGANISM: Mus musculus

<400> SEQUENCE: 60

Arg Ile Asn Pro Gly Asp Gly Asn Thr Asn Tyr Asn Gly Lys Phe Met
  1               5                  10                  15
Ala

<210> SEQ ID NO 61
<211> LENGTH: 10
<212> TYPE: PRT
<213> ORGANISM: Mus musculus

<400> SEQUENCE: 61

Gly Asp Arg Trp Ser Gly Ala Met Asp Tyr
  1               5                  10

<210> SEQ ID NO 62
<211> LENGTH: 12
<212> TYPE: PRT
<213> ORGANISM: Mus musculus

<400> SEQUENCE: 62

Arg Ala Ser Ser Ser Val Ser Ser Ser Tyr Leu His
  1               5                  10

<210> SEQ ID NO 63
<211> LENGTH: 7
<212> TYPE: PRT
<213> ORGANISM: Mus musculus

<400> SEQUENCE: 63

Ser Thr Ser Asn Leu Ala Ser
  1               5

<210> SEQ ID NO 64
<211> LENGTH: 9
<212> TYPE: PRT
<213> ORGANISM: Mus musculus

<400> SEQUENCE: 64

Gln Gln Tyr Ser Gly Phe Pro Leu Thr
  1               5

<210> SEQ ID NO 65
<211> LENGTH: 41
<212> TYPE: DNA
<213> ORGANISM: Artificial sequence
<220> FEATURE:
<223> OTHER INFORMATION: Synthetic construct forward primer amplifying
      KM3907VH

<400> SEQUENCE: 65
cgagcggccg ccttctccac agtcccagaa cacactcact c                         41

<210> SEQ ID NO 66
<211> LENGTH: 40
<212> TYPE: DNA
<213> ORGANISM: Artificial sequence
<220> FEATURE:
```

-continued

```
<223> OTHER INFORMATION: Synthetic construct reverse primer amplifying
      KM3907VH

<400> SEQUENCE: 66
gtaagggccc ttggtggagg ctgaggagac ggtgactgag                              40

<210> SEQ ID NO 67
<211> LENGTH: 124
<212> TYPE: DNA
<213> ORGANISM: Artificial sequence
<220> FEATURE:
<223> OTHER INFORMATION: Synthetic construct forward primer amplifying
      KM3907VL

<400> SEQUENCE: 67
ccgaattcgc ctcttcaaaa tgaagttgcc tgttaggctg ttggtgctga tgttctggat        60
tcctgcttcc agcagtggaa atgtgctcac ccagtctcca gcaatcatgt ctgcatctcc       120
aggg                                                                    124

<210> SEQ ID NO 68
<211> LENGTH: 30
<212> TYPE: DNA
<213> ORGANISM: Artificial sequence
<220> FEATURE:
<223> OTHER INFORMATION: Synthetic construct reverse primer amplifying
      KM3907VL

<400> SEQUENCE: 68
agccaccgta cgtttcagtt ccagcttggt                                         30

<210> SEQ ID NO 69
<211> LENGTH: 726
<212> TYPE: DNA
<213> ORGANISM: Artificial sequence
<220> FEATURE:
<221> NAME/KEY: CDS
<222> LOCATION: (1)..(726)
<223> OTHER INFORMATION: Synthetic construct of 4-EL1/6-EL2 DNA sequence

<400> SEQUENCE: 69
atggcctcca tggggctaca ggtaatgggc atcgcgctgg ccgtcctggg ctggctggcc        60
gtcatgctgt gctgcgcgct gcccatgtgg cgcgtgacgg ccttcatcgg cagcaacatt       120
gtcacctcgc agaccatctg ggagggccta tggatgaact gcgtggtgca gagcaccggc       180
cagatgcagt gcaaggtgta cgactcgctg ctggcactgc cgcaggacct gcaggctgca       240
cgtgccctct gtgtcatcgc cctccttgtg gccctgttcg gcttgctggt ctaccttgct       300
ggggccaagt gtaccacctg tgtggaggag aaggattcca aggcccgcct ggtgctcacc       360
tctgggattg tctttgtcat ctcaggggtc ctgacgctaa tccccgtgtg ctggacggcg       420
catgccgtca tccgggactt ctataacccc ctggtggctg aggcccaaaa gcggagctgg       480
ggggcctccc tctacttggg ctgggcggcc tcaggccttt tgttgctggg tggggggttg       540
ctgtgctgca cttgcccctc ggggggtcc cagggcccca gccattacat ggcccgctac       600
tcaacatctg cccctgccat ctctcggggg ccctctgagt accctaccaa gaattacgtc       660
gaacaaaaac tcatctcaga agaggatctg aatatgcata ccggtcatca tcaccatcac       720
cattga                                                                  726

<210> SEQ ID NO 70
<211> LENGTH: 241
<212> TYPE: PRT
<213> ORGANISM: Artificial sequence
```

<220> FEATURE:
<223> OTHER INFORMATION: Synthetic construct of 4-EL1/6-EL2 amino acid sequence

<400> SEQUENCE: 70

| Met | Ala | Ser | Met | Gly | Leu | Gln | Val | Met | Gly | Ile | Ala | Leu | Ala | Val | Leu |
|---|---|---|---|---|---|---|---|---|---|---|---|---|---|---|---|
| 1 | | | | 5 | | | | | 10 | | | | | 15 | |

| Gly | Trp | Leu | Ala | Val | Met | Leu | Cys | Cys | Ala | Leu | Pro | Met | Trp | Arg | Val |
|---|---|---|---|---|---|---|---|---|---|---|---|---|---|---|---|
| | | | 20 | | | | | 25 | | | | | 30 | | |

| Thr | Ala | Phe | Ile | Gly | Ser | Asn | Ile | Val | Thr | Ser | Gln | Thr | Ile | Trp | Glu |
|---|---|---|---|---|---|---|---|---|---|---|---|---|---|---|---|
| | | | 35 | | | | | 40 | | | | | 45 | | |

| Gly | Leu | Trp | Met | Asn | Cys | Val | Val | Gln | Ser | Thr | Gly | Gln | Met | Gln | Cys |
|---|---|---|---|---|---|---|---|---|---|---|---|---|---|---|---|
| | 50 | | | | | 55 | | | | | 60 | | | | |

| Lys | Val | Tyr | Asp | Ser | Leu | Leu | Ala | Leu | Pro | Gln | Asp | Leu | Gln | Ala | Ala |
|---|---|---|---|---|---|---|---|---|---|---|---|---|---|---|---|
| 65 | | | | | 70 | | | | | 75 | | | | | 80 |

| Arg | Ala | Leu | Cys | Val | Ile | Ala | Leu | Leu | Val | Ala | Leu | Phe | Gly | Leu | Leu |
|---|---|---|---|---|---|---|---|---|---|---|---|---|---|---|---|
| | | | | 85 | | | | | 90 | | | | | 95 | |

| Val | Tyr | Leu | Ala | Gly | Ala | Lys | Cys | Thr | Thr | Cys | Val | Glu | Glu | Lys | Asp |
|---|---|---|---|---|---|---|---|---|---|---|---|---|---|---|---|
| | | | 100 | | | | | 105 | | | | | 110 | | |

| Ser | Lys | Ala | Arg | Leu | Val | Leu | Thr | Ser | Gly | Ile | Val | Phe | Val | Ile | Ser |
|---|---|---|---|---|---|---|---|---|---|---|---|---|---|---|---|
| | | 115 | | | | | 120 | | | | | 125 | | | |

| Gly | Val | Leu | Thr | Leu | Ile | Pro | Val | Cys | Trp | Thr | Ala | His | Ala | Val | Ile |
|---|---|---|---|---|---|---|---|---|---|---|---|---|---|---|---|
| 130 | | | | | 135 | | | | | 140 | | | | | |

| Arg | Asp | Phe | Tyr | Asn | Pro | Leu | Val | Ala | Glu | Ala | Gln | Lys | Arg | Glu | Leu |
|---|---|---|---|---|---|---|---|---|---|---|---|---|---|---|---|
| 145 | | | | | 150 | | | | | 155 | | | | | 160 |

| Gly | Ala | Ser | Leu | Tyr | Leu | Gly | Trp | Ala | Ala | Ser | Gly | Leu | Leu | Leu | Leu |
|---|---|---|---|---|---|---|---|---|---|---|---|---|---|---|---|
| | | | | 165 | | | | | 170 | | | | | 175 | |

| Gly | Gly | Gly | Leu | Leu | Cys | Cys | Thr | Cys | Pro | Ser | Gly | Gly | Ser | Gln | Gly |
|---|---|---|---|---|---|---|---|---|---|---|---|---|---|---|---|
| | | 180 | | | | | 185 | | | | | 190 | | | |

| Pro | Ser | His | Tyr | Met | Ala | Arg | Tyr | Ser | Thr | Ser | Ala | Pro | Ala | Ile | Ser |
|---|---|---|---|---|---|---|---|---|---|---|---|---|---|---|---|
| | | | 195 | | | | | 200 | | | | | 205 | | |

| Arg | Gly | Pro | Ser | Glu | Tyr | Pro | Thr | Lys | Asn | Tyr | Val | Glu | Gln | Lys | Leu |
|---|---|---|---|---|---|---|---|---|---|---|---|---|---|---|---|
| | 210 | | | | | 215 | | | | | 220 | | | | |

| Ile | Ser | Glu | Glu | Asp | Leu | Asn | Met | His | Thr | Gly | His | His | His | His | His |
|---|---|---|---|---|---|---|---|---|---|---|---|---|---|---|---|
| 225 | | | | | 230 | | | | | 235 | | | | | 240 |

His

<210> SEQ ID NO 71
<211> LENGTH: 693
<212> TYPE: DNA
<213> ORGANISM: Artificial sequence
<220> FEATURE:
<221> NAME/KEY: CDS
<222> LOCATION: (1)..(693)
<223> OTHER INFORMATION: Synthetic construct of 6-EL1/4-EL2 DNA sequence

<400> SEQUENCE: 71

| atggcctctg | ccggaatgca | gatcctggga | gtcgtcctga | cactgctggg | ctgggtgaat | 60 |
| ggcctggtct | cctgtgccct | gcccatgtgg | aaggtgaccg | ctttcatcgg | caacagcatc | 120 |
| gtggtggccc | agtggtgtgt | ggagggcctg | tggatgtcct | gcgtggtgca | gagcaccggc | 180 |
| cagatgcagt | gcaaggtgta | cgactcactg | ctggcgctgc | cacaggacct | gcaggcggcc | 240 |
| cgcgccctcg | tcatcatcag | catcatcgtg | gctgctctgg | gcgtgctgct | gtccgtggtg | 300 |
| gggggcaagt | gtaccaactg | cctggaggat | gaaagcgcca | aggccaagac | catgatcgtg | 360 |
| gcgggcgtgt | tgttcctgtt | ggccggcctt | atggtgatag | tgccggtgtc | ctggacggcc | 420 |
| cacaacatca | tccaagactt | ctacaatccg | ctggtggcct | ccgggcagaa | gcgggagatg | 480 |

```
ggtgcctcgc tctacgtcgg ctgggccgcc tccggcctgc tgctccttgg cgggggggctg    540 ctttgctgca actgtccacc ccgcacagac aagccttact ccgccaagta ttctgctgcc    600
cgctctgctg ctgccagcaa ctacgtggaa caaaaactca tctcagaaga ggatctgaat    660
atgcataccg gtcatcatca ccatcaccat tga                                 693
```

<210> SEQ ID NO 72
<211> LENGTH: 230
<212> TYPE: PRT
<213> ORGANISM: Artificial sequence
<220> FEATURE:
<223> OTHER INFORMATION: Synthetic construct of 6-EL1/4-EL2 amino acid
      sequence

<400> SEQUENCE: 72

```
Met Ala Ser Ala Gly Met Gln Ile Leu Gly Val Val Leu Thr Leu Leu
 1               5                  10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
 65                  70                  75                  80

Arg Ala Leu Val Ile Ile Ser Ile Ile Val Ala Ala Leu Gly Val Leu
                 85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ala Ser Asn Tyr
        195                 200                 205

Val Glu Gln Lys Leu Ile Ser Glu Glu Asp Leu Asn Met His Thr Gly
    210                 215                 220

His His His His His His
225                 230
```

<210> SEQ ID NO 73
<211> LENGTH: 423
<212> TYPE: DNA
<213> ORGANISM: Artificial sequence
<220> FEATURE:
<221> NAME/KEY: CDS
<222> LOCATION: (1)..(423)
<223> OTHER INFORMATION: Synthetic construct of anti-CLDN4 humanized
      antibody HV0

<400> SEQUENCE: 73

```
atg aga gtg ctt att tta ttg tgg ctg ttc aca gcc ttt cct ggt att     48
Met Arg Val Leu Ile Leu Leu Trp Leu Phe Thr Ala Phe Pro Gly Ile
```

```
                1               5              10              15
ctt agt gag gtc cag ctg gtg caa tct ggt gcc gag gtg aag aag cct    96
Leu Ser Glu Val Gln Leu Val Gln Ser Gly Ala Glu Val Lys Lys Pro
                20                          25                          30 ggt gct tca gtg aag att tcc tgt aag gct tct ggg tac acg ttc act   144
Gly Ala Ser Val Lys Ile Ser Cys Lys Ala Ser Gly Tyr Thr Phe Thr
            35                          40                          45 gac tac tac atg aat tgg gtg cga cag gct cct ggg cag ggg ctt gag   192
Asp Tyr Tyr Met Asn Trp Val Arg Gln Ala Pro Gly Gln Gly Leu Glu
        50                          55                          60 tgg atg ggt gat gtt gtt cct aac aat ggt gtt cct acc tac aac cag   240
Trp Met Gly Asp Val Val Pro Asn Asn Gly Val Pro Thr Tyr Asn Gln
65                          70                          75                          80 aag ttc aag ggc cga gtg aca att act gct gac aag tcc aca agc aca   288
Lys Phe Lys Gly Arg Val Thr Ile Thr Ala Asp Lys Ser Thr Ser Thr
                    85                          90                          95 gcc tac atg gag ctc cgc agc ctg cga tct gag gac acc gca gtc tat   336
Ala Tyr Met Glu Leu Arg Ser Leu Arg Ser Glu Asp Thr Ala Val Tyr
                100                         105                         110 tac tgt gca cga cct cat tat tac tac gct ggt cgc tcg ggt gct atg   384
Tyr Cys Ala Arg Pro His Tyr Tyr Tyr Ala Gly Arg Ser Gly Ala Met
            115                         120                         125 gac tac tgg ggt caa ggg acc ctg gtc acc gtc tcc tca               423
Asp Tyr Trp Gly Gln Gly Thr Leu Val Thr Val Ser Ser
        130                         135                         140

<210> SEQ ID NO 74
<211> LENGTH: 123
<212> TYPE: PRT
<213> ORGANISM: Artificial sequence
<220> FEATURE:
<223> OTHER INFORMATION: Synthetic construct of anti-CLDN4 humanized
      antibody HV0

<400> SEQUENCE: 74

Glu Val Gln Leu Val Gln Ser Gly Ala Glu Val Lys Lys Pro Gly Ala
 1               5                  10                  15

Ser Val Lys Ile Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Val Val Pro Asn Asn Gly Val Pro Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Pro His Tyr Tyr Tyr Ala Gly Arg Ser Gly Ala Met Asp Tyr
            100                 105                 110

Trp Gly Gln Gly Thr Leu Val Thr Val Ser Ser
        115                 120

<210> SEQ ID NO 75
<211> LENGTH: 390
<212> TYPE: DNA
<213> ORGANISM: Artificial sequence
<220> FEATURE:
<221> NAME/KEY: CDS
<222> LOCATION: (1)..(390)
<223> OTHER INFORMATION: Synthetic construct of anti-CLDN4 humanized
      antibody LV0
```

```
<400> SEQUENCE: 75 atg cat ttt caa gtg cag att ttc agc ttc ctg ctt att tcg gcc tca      48
Met His Phe Gln Val Gln Ile Phe Ser Phe Leu Leu Ile Ser Ala Ser
 1               5                  10                  15 gtc ata atg tcc aga gga gat att cag ctc acc cag tct cca tcg agc      96
Val Ile Met Ser Arg Gly Asp Ile Gln Leu Thr Gln Ser Pro Ser Ser
             20                  25                  30 ctc tct gca tct gta ggg gat cgg gtc acc atc acc tgc act gcc agc     144
Leu Ser Ala Ser Val Gly Asp Arg Val Thr Ile Thr Cys Thr Ala Ser
         35                  40                  45 tca act gta agt tcc act tac tta cac tgg tac cag cag aag cca ggc     192
Ser Thr Val Ser Ser Thr Tyr Leu His Trp Tyr Gln Gln Lys Pro Gly
     50                  55                  60 aaa gct cca aaa ctc ctg att tat agc aca tcc aac ctg gct tct ggc     240
Lys Ala Pro Lys Leu Leu Ile Tyr Ser Thr Ser Asn Leu Ala Ser Gly
 65                  70                  75                  80 gtc cca tca cgc ttc agt ggc agt ggg tct ggg acc gat tac act ctc     288
Val Pro Ser Arg Phe Ser Gly Ser Gly Ser Gly Thr Asp Tyr Thr Leu
                 85                  90                  95 aca atc agc agc ctc cag cca gaa gat ttc gcc act tat tac tgc cac     336
Thr Ile Ser Ser Leu Gln Pro Glu Asp Phe Ala Thr Tyr Tyr Cys His
            100                 105                 110 cag tat cat cgt tcc cca cca acg ttc ggc cag ggc acc aag ctg gaa     384
Gln Tyr His Arg Ser Pro Pro Thr Phe Gly Gln Gly Thr Lys Leu Glu
        115                 120                 125 atc aaa                                                              390
Ile Lys
    130

<210> SEQ ID NO 76
<211> LENGTH: 108
<212> TYPE: PRT
<213> ORGANISM: Artificial sequence
<220> FEATURE:
<223> OTHER INFORMATION: Synthetic construct of anti-CLDN4 humanized
      antibody LV0

<400> SEQUENCE: 76

Asp Ile Gln Leu Thr Gln Ser Pro Ser Ser Leu Ser Ala Ser Val Gly
 1               5                  10                  15

Asp Arg Val Thr Ile Thr Cys Thr Ala Ser Ser Thr Val Ser Ser Thr
             20                  25                  30

Tyr Leu His Trp Tyr Gln Gln Lys Pro Gly Lys Ala Pro Lys Leu Leu
         35                  40                  45

Ile Tyr Ser Thr Ser Asn Leu Ala Ser Gly Val Pro Ser Arg Phe Ser
     50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Tyr His Arg Ser Pro
                 85                  90                  95

Pro Thr Phe Gly Gln Gly Thr Lys Leu Glu Ile Lys
            100                 105

<210> SEQ ID NO 77
<211> LENGTH: 143
<212> TYPE: DNA
<213> ORGANISM: Artificial sequence
<220> FEATURE:
<223> OTHER INFORMATION: Synthetic DNA of HV0

<400> SEQUENCE: 77
```

```
aattaaccct cactaaaggg atccgcggcc gcgacccctc accatgagag tgcttattt    60 attgtggctg ttcacagcct ttcctggtat tcttagtgag gtccagctgg tgcaatctgg   120
tgccgaggtg aagaagcctg ggg                                           143
```

```
<210> SEQ ID NO 78
<211> LENGTH: 143
<212> TYPE: DNA
<213> ORGANISM: Artificial sequence
<220> FEATURE:
<223> OTHER INFORMATION: Synthetic DNA of HV0

<400> SEQUENCE: 78
caccattgtt aggaacaaca tcacccatcc actcaagccc ctgcccagga gcctgtcgca    60
cccaattcat gtagtagtca gtgaacgtgt acccagaagc cttacaggaa atcttcactg   120
aagccccagg cttcttcacc tcg                                           143
```

```
<210> SEQ ID NO 79
<211> LENGTH: 143
<212> TYPE: DNA
<213> ORGANISM: Artificial sequence
<220> FEATURE:
<223> OTHER INFORMATION: Synthetic DNA of HV0

<400> SEQUENCE: 79
tgttgttcct aacaatggtg ttcctaccta caaccagaag ttcaagggcc gagtgacaat    60
tactgctgac aagtccacaa gcacagccta catggagctc cgcagcctgc gatctgagga   120
caccgcagtc tattactgtg cac                                           143
```

```
<210> SEQ ID NO 80
<211> LENGTH: 142
<212> TYPE: DNA
<213> ORGANISM: Artificial sequence
<220> FEATURE:
<223> OTHER INFORMATION: Synthetic DNA of HV0

<400> SEQUENCE: 80
gtaatacgac tcactatagg gcaagcttgg gcccttggtg gaggctgagg agacggtgac    60
cagggtccct tgaccccagt agtccatagc acccgagcga ccagcgtagt aataatgagg   120
tcgtgcacag taatagactg cg                                            142
```

```
<210> SEQ ID NO 81
<211> LENGTH: 132
<212> TYPE: DNA
<213> ORGANISM: Artificial sequence
<220> FEATURE:
<223> OTHER INFORMATION: Synthetic DNA of LV0

<400> SEQUENCE: 81
aattaaccct cactaaaggg ggatccgaat tcgcctcctc aaaatgcatt ttcaagtgca    60
gattttcagc ttcctgctta tttcggcctc agtcataatg tccagaggag atattcagct   120
cacccagtct cc                                                       132
```

```
<210> SEQ ID NO 82
<211> LENGTH: 132
<212> TYPE: DNA
<213> ORGANISM: Artificial sequence
<220> FEATURE:
<223> OTHER INFORMATION: Synthetic DNA of LV0

<400> SEQUENCE: 82
```

```
tggagctttg cctggcttct gctggtacca gtgtaagtaa gtggaactta cagttgagct      60
ggcagtgcag gtgatggtga cccgatcccc tacagatgca gagaggctcg atggagactg     120
ggtgagctga at                                                         132

<210> SEQ ID NO 83
<211> LENGTH: 132
<212> TYPE: DNA
<213> ORGANISM: Artificial sequence
<220> FEATURE:
<223> OTHER INFORMATION: Synthetic DNA of LV0

<400> SEQUENCE: 83
agaagccagg caaagctcca aaactcctga tttatagcac atccaacctg gcttctggcg      60
tcccatcacg cttcagtggc agtgggtctg ggaccgatta cactctcaca atcagcagcc    120
tccagccaga ag                                                         132

<210> SEQ ID NO 84
<211> LENGTH: 131
<212> TYPE: DNA
<213> ORGANISM: Artificial sequence
<220> FEATURE:
<223> OTHER INFORMATION: Synthetic DNA of LV0

<400> SEQUENCE: 84
gtaatacgac tcactatagg gcaagcttcg tacgtttgat ttccagcttg gtgccctggc      60
cgaacgttgg tggggaacga tgatactggt ggcagtaata agtggcgaaa tcttctggct    120
ggaggctgct g                                                          131
```